(12) United States Patent
Zhang et al.

(10) Patent No.: US 7,223,575 B2
(45) Date of Patent: May 29, 2007

(54) *ZYMOMONAS* PENTOSE-SUGAR FERMENTING STRAINS AND USES THEREOF

(75) Inventors: Min Zhang, Lakewood, CO (US);
Yat-Chen Chou, Golden, CO (US);
William Howe, Golden, CO (US);
Christine Eddy, Golden, CO (US);
Kent Evans, Littleton, CO (US); Ali Mohagheghi, Northglenn, CO (US)

(73) Assignee: Midwest Research Institute, Kansas City, MO (US)

( * ) Notice: Subject to any disclaimer, the term of this patent is extended or adjusted under 35 U.S.C. 154(b) by 429 days.

(21) Appl. No.: 10/134,655

(22) Filed: Apr. 27, 2002

(65) Prior Publication Data

US 2003/0162271 A1    Aug. 28, 2003

Related U.S. Application Data

(63) Continuation-in-part of application No. PCT/US01/11334, filed on Apr. 6, 2001, which is a continuation-in-part of application No. 09/565,233, filed on May 1, 2000, which is a continuation of application No. 09/565,233, filed on May 1, 2000.

(51) Int. Cl.
*C12P 7/06* (2006.01)
(52) U.S. Cl. .................. 435/161; 435/41; 435/132; 435/155; 435/157
(58) Field of Classification Search ................. 435/41, 435/132, 155, 157, 161
See application file for complete search history.

(56) References Cited

U.S. PATENT DOCUMENTS

| | | | | |
|---|---|---|---|---|
| 5,514,583 A | * | 5/1996 | Picataggio et al. | 435/252.3 |
| 5,712,133 A | * | 1/1998 | Picataggio et al. | 435/161 |
| 5,843,760 A | * | 12/1998 | Zhang et al. | 435/252.3 |
| 2002/0151034 A1 | * | 10/2002 | Zhang et al. | 435/252.2 |

* cited by examiner

*Primary Examiner*—James Ketter
*Assistant Examiner*—David Lambertson
(74) *Attorney, Agent, or Firm*—Paul J. White

(57) ABSTRACT

Disclosed in the present invention is a *Zymomonas* integrant and derivatives of these integrants that posses the ability to ferment pentose into ethanol. The genetic sequences encoding for the pentose-fermenting enzymes are integrated into the *Zymomonas* in a two-integration event of homologous recombination and transposition. Each operon includes more than one pentose-reducing enzyme encoding sequence. The integrant in some embodiments includes enzyme sequences encoding xylose isomerase, xylulokinase, transketolase and transketolase. The *Zymomonas* integrants are highly stable, and retain activity for producing the pentose-fermenting enzyme for between 80 to 160 generations. The integrants are also resistant to acetate inhibition, as the integrants demonstrate efficient ethanol production even in the presence of 8 up to 16 grams acetate per liter media. These stably integrated sequences provide a unique *Zymomonas* that may then be used for the efficient conversion of pentose sugars (xylose, arabinose) to ethanol. Method of using the *Zymomonas* integrants and derivatives thereof in production of ethanol from cellulosic feedstock is also disclosed. The invention also provides a method for preparing a *Zymomonas* integrant as part of the present invention. The host *Zymomonas* strain found particularly useful in the creation of these compositions and methods is *Zymomonas mobilis* 31821.

9 Claims, 41 Drawing Sheets

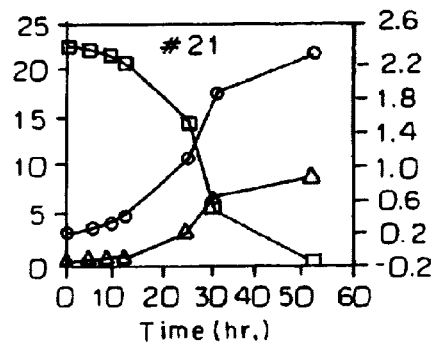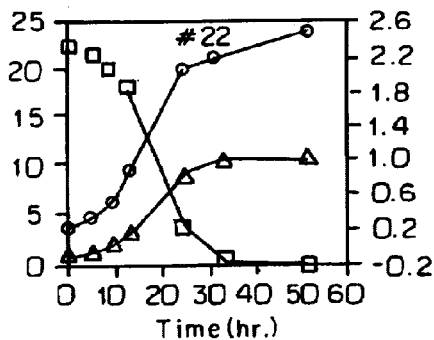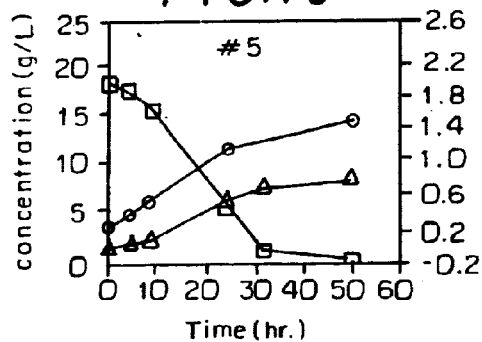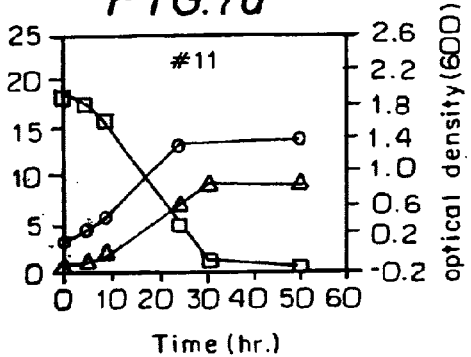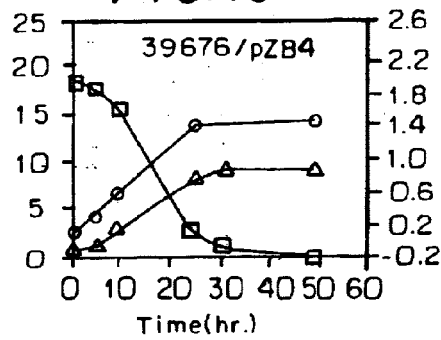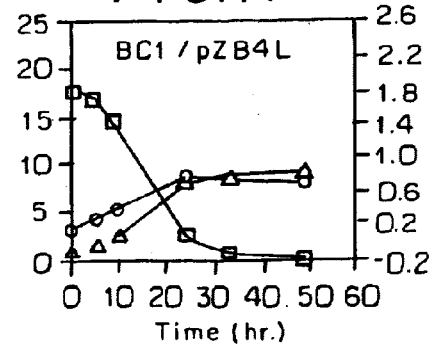

Fig. 12A
Probe: ara
PstI digestion
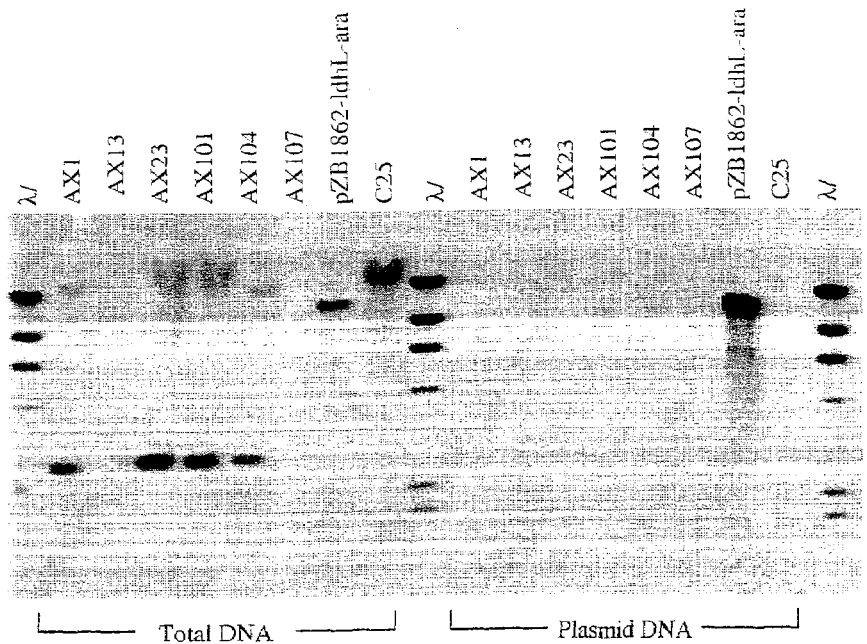
Fig. 12B
Probe: ldh
PstI digestion
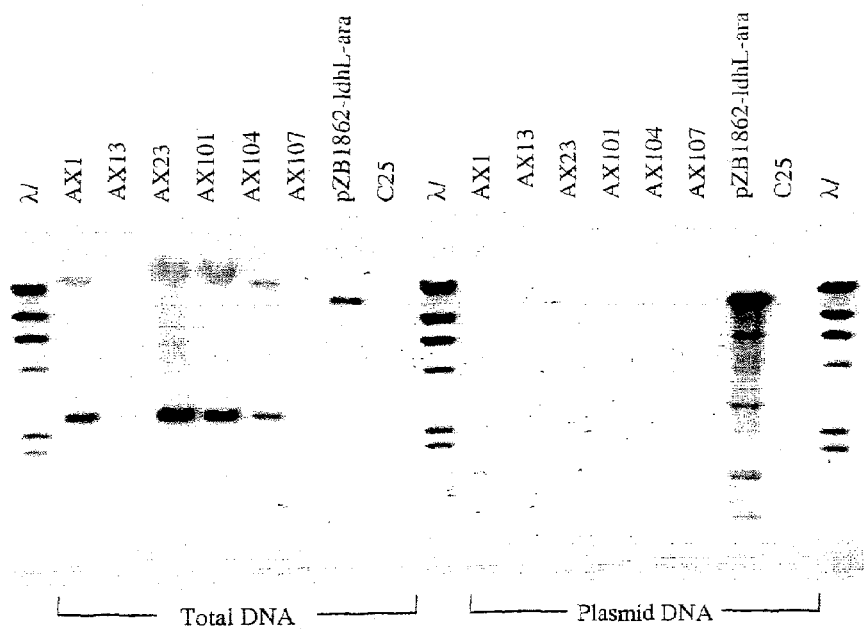
Fig. 12.

Fig. 13A

Probe:tnp
PstI digestion

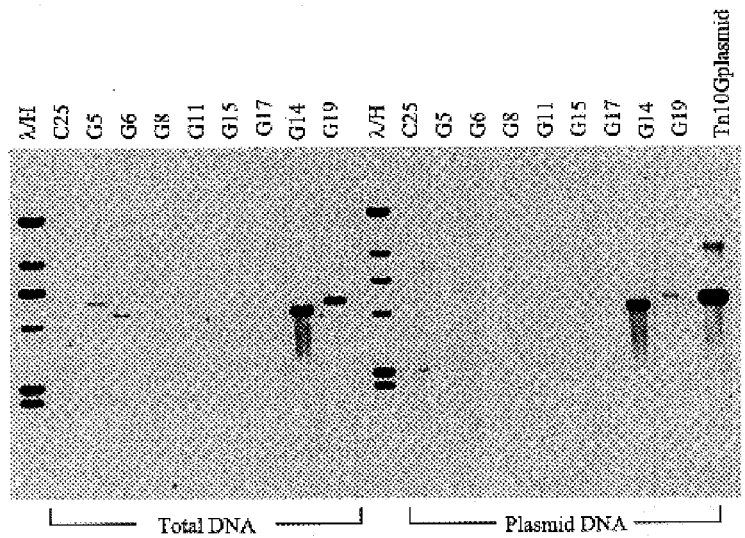

Total DNA — Plasmid DNA

Fig. 13B

Probe:ara
PstI digestion

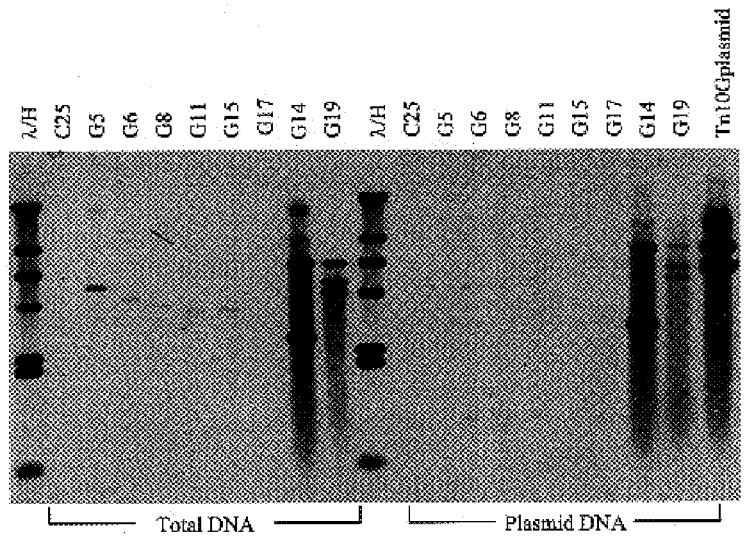

Total DNA — Plasmid DNA

Fig. 13. Southern analysis of the chromosomal integrated xylose/arabinose-fermenting *Zymomonas* strains from transposon integration using DIG-tnp and DIG-ara probes. G5, 6, 11, 15, 17, 14 and 19 are *araBAD* integrants. C25 is the host control. Tn10G is the plasmid control. λ/H is a molecular weight marker: 23, 9.4, 6.6, 4.3, 2.3 and 2.0 kb.

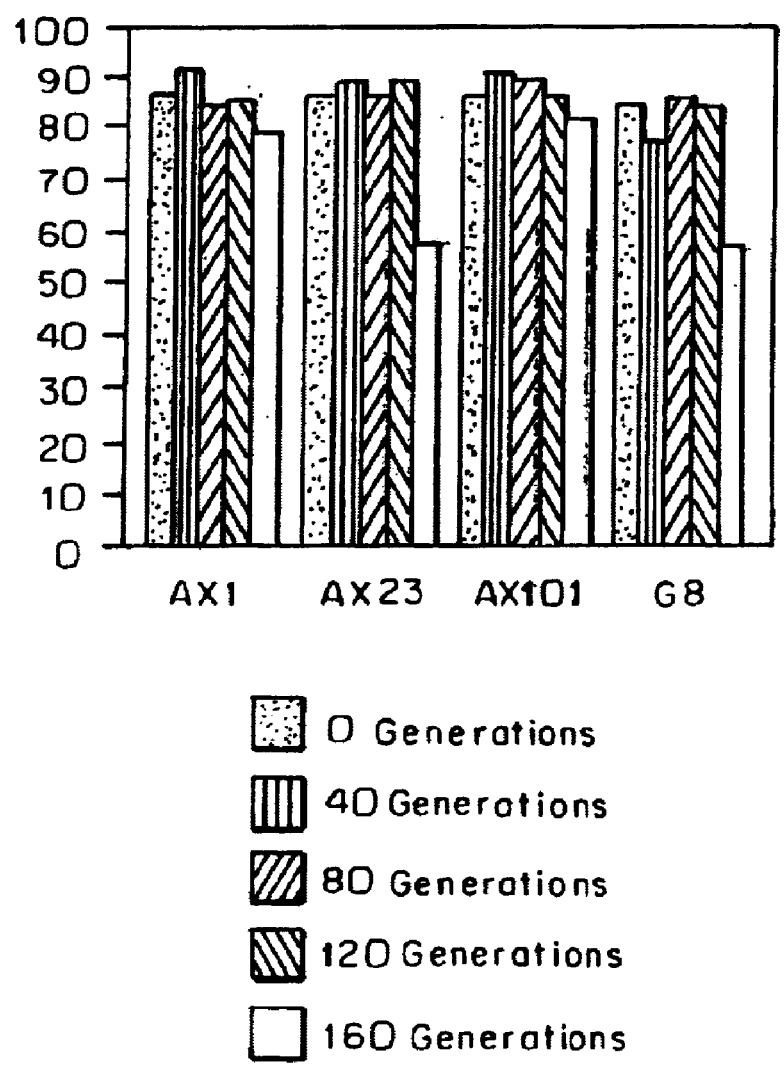

☐ Xylose
○ Glucose
△ Arabinose
✕ Ethanol

Growth of PgapxylABPgaptaltkt integrants (1st transfer)

Growth of PgapxylABPgaptaltkt integrants (6th transfer)

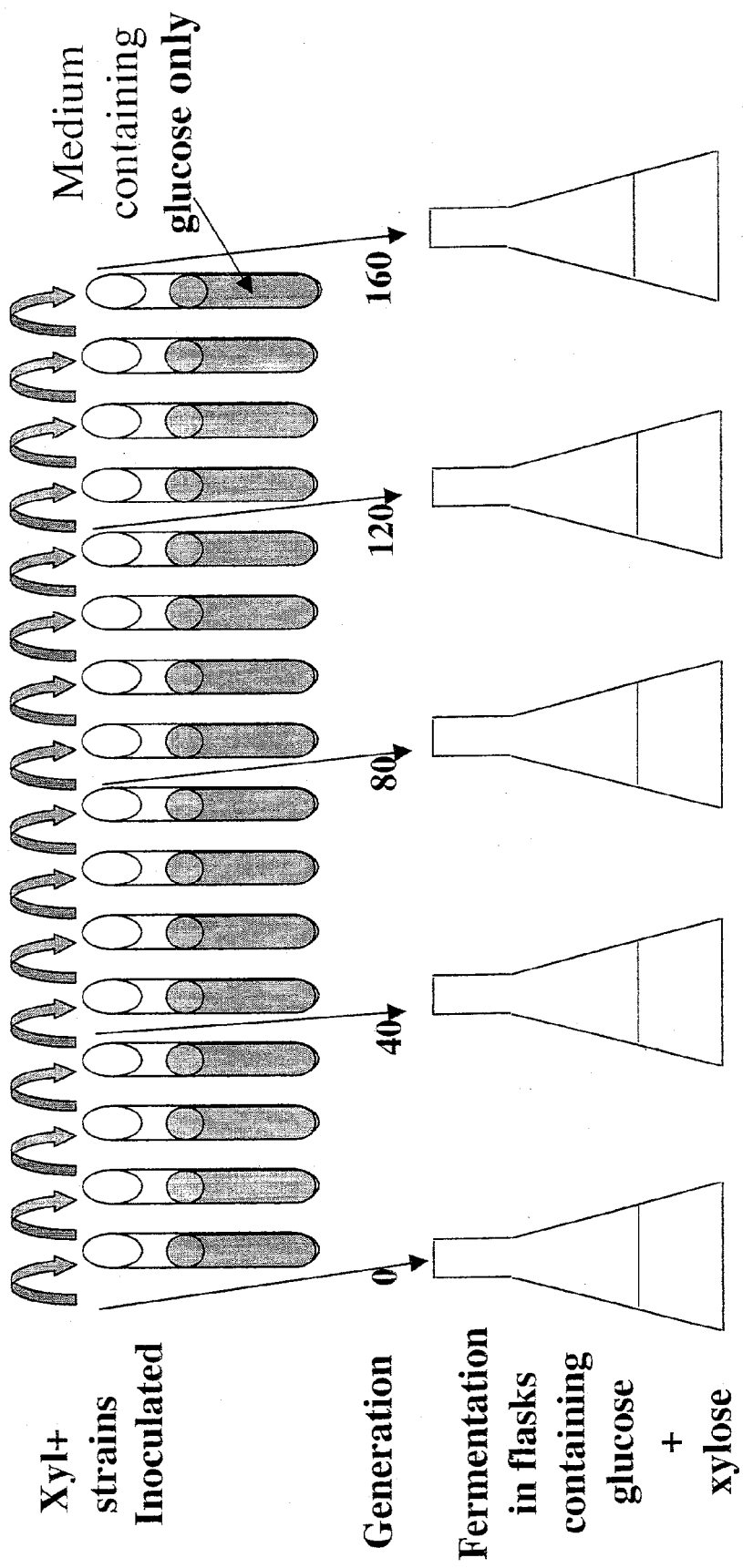
Figure 31. Stability Test

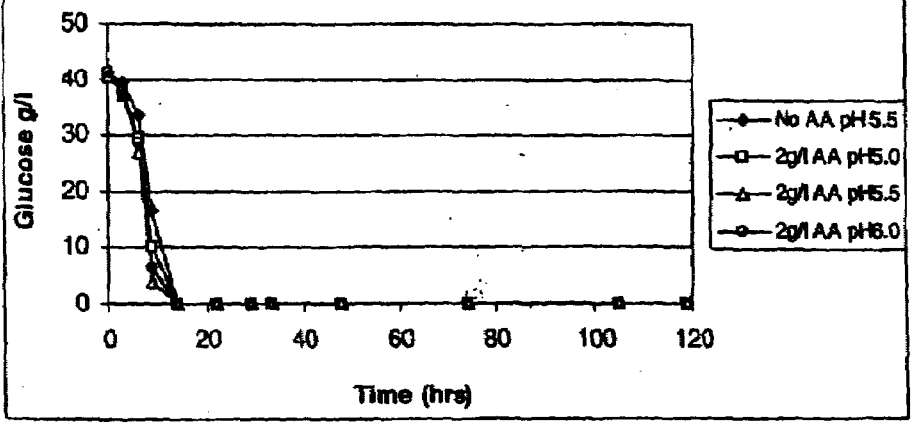
FIG.34a Glucose Profile
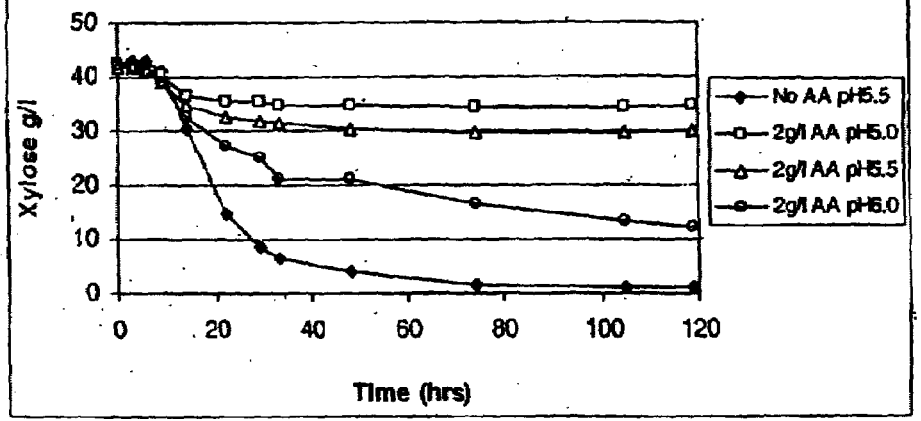
FIG.34b Xylose Profile
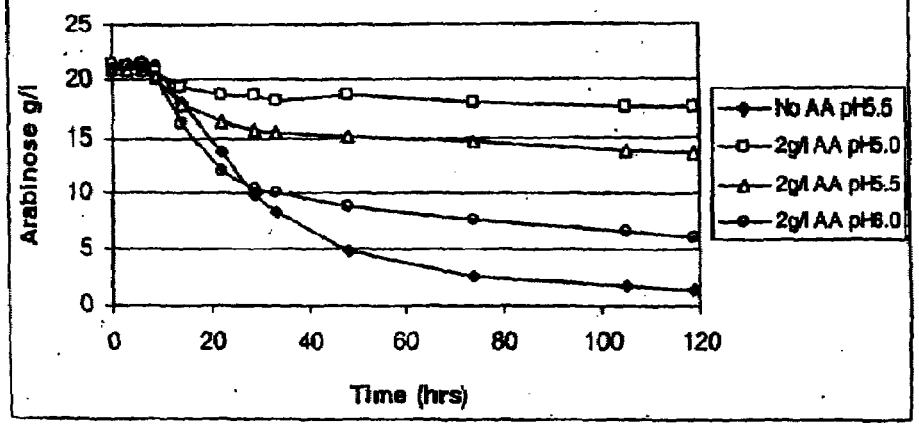
FIG.34c Arabinose Profile

ZYMOMONAS PENTOSE-SUGAR FERMENTING STRAINS AND USES THEREOF

The present application is a continuation-in-part of U.S. patent application Ser. No. 09/565,233, filed May 1, 2000. The present application is a continuation-in-part of PCT application PCT/US01/11334, filed Apr. 6, 2001, which is a continuation of U.S. Ser. No. 09/565,233, filed May 1, 2000.

CONTRACTUAL ORIGIN OF THE INVENTION

The United States Government has rights in this invention pursuant to contract No. DE-AC36-99G010337 between the United States Department of Energy and the Midwest Research Institute.

BACKGROUND OF THE INVENTION

1. Field of the Invention

The present invention relates to the biological conversion of cellulosic substrates into fuels and chemicals, and in particular to recombinant *Zymomonas mobilis* strains which ferment xylose, arabinose, and mannose or all of these into ethanol.

2. Description of the Related Art

Fermentation technology is useful for the conversion renewable biomass cellulose substrates into fuels and chemicals, such as ethanol. A typical substrate is comprised of 35–45% cellulose, 30–40% hemicellulose, and 15% lignin. The hydrolysis fraction contains glucose polymers, and the hemicellulose fraction contains mostly xylose. Arabinose is also a significant fermentable substrate found in biomass materials, such as switchgrass grass and corn fiber. Thus, achieving a high rate of specific product formation and conversion efficiency in the fermentation of the pentose sugars is vital to the commercial production of fuels and chemicals from a renewable substrates.

*Z. mobilis* is widely reported for its ability to rapidly and efficiently convert glucose substrates into ethanol, at a low pH, in an anaerobic culture, and in a medium which contains the inhibitory compounds typically associated with a lignocellulose-hydrolysate. A distinct disadvantage in the use of *Z. mobilis* is, however, that it does not ferment pentose sugars. To overcome this disadvantage, the prior art has focused on recombinant *Z. mobilis* strains which ferment a mixture of glucose, and xylose or arabinose, or both, using exogenous genes which catalyze the metabolism of xylose and arabinose. These strains, and the cloning vectors, are based on the use of multiple-copy plasmids having antibiotic resistance markers.

U.S. Pat. No. 5,514,583 relates to a transformed *Z. mobilis* xylose fermenting strain (CP4/pZB4 and pZB5) having exogenous genes, and plasmid vectors (pZB4 and pZB5) encoding xylose isomerase, xylulokinase, transaldolase and transketolase, and further comprising at least one promoter (Pgap and Peno) recognized by *Zymomonas* which regulates the expression of at least one of said genes. The microorganism is capable of growing on xylose as a sole carbon source, and fermenting xylose to ethanol at about 88% of the maximum theoretic yield. U.S. Pat. Nos. 5,712,133 and 5,726,053 relates to, inter alia, *Z. mobilis* arabinose fermenting transformants (39676/pZB 206), containing exogenous genes that encode L-arabinose isomerase, L-ribulokinase and L-ribulose-5-phosphate-4-epimerase, transaldolase and transketolase which impart arabinose to ethanol fermentation capability. The plasmid vector (pZB 206) and a process of using the transformants of the fermentation of a glucose and arabinose containing substrate is also described. U.S. Pat. No. 5,843,760 discloses a *Z. mobilis* xylose and arabinose fermenting transformant (206C/pZB301) containing exogenous genes encoding xylose isomerase, xylulokinase, L-arabinose isomerase, L-ribulokinase, L-ribulose-5-phosphate 4-epimerase, transaldolase and transketolase, and further comprising at least one promoter recognized by *Zymomonas* which regulates the expression of at least one of said genes, wherein said microorganism is capable of growing on arabinose and/or xylose, alone or in combination, as the carbon source and fermenting said arabinose and xylose to ethanol. The process of using the transformants together with the plasmid vectors (pZB301, pZB401, pZB402, and pZB 403) is also described. Although hybrid plasmids may be readily maintained in *Z. mobilis* when cultivated in a monoculture under controlled conditions, they frequently become unstable when the host organism is grown in the absence of selection pressure for plasmid maintenance, i.e., in the presence of antibiotics. For example, the exogenous genes in the above referenced strains are capable of stable expression for about forty generations. Instability may be exacerbated when *Z. mobilis* has to compete with other organisms in a mixed culture, such as a cellulose simultaneous-saccharification-fermentation process. In addition, antibiotic resistance markers are generally undesirable for industrial application, such as the large-scale production of ethanol. Thus, it is preferable to insert the cloned genes into the *Z. mobilis* genome, where they are maintained at a low, natural copy number, and are thus not over-expressed, and where, they should be as stable as genomic DNA.

In *Escherichia coli*, the classical method for generating genomic inserts of foreign genes involves the use of specialized 1 phage cloning vectors that can exist stable in the lysogenic state. Alternatively, genes can be inserted through homologous recombination, when bracketed with *E. coli* chromosomal sequences, or by transposition if the genes can be cloned in the permissive sites of a transposon. While transposition has been demonstrated in *Z. mobilis*, (Pappas, K. M., et al., (1997) Journal of Applied Microbiology, 82: 379–388), it has been limited to mini Mm or Tn5 multiple transposition of random auxotrophy or antibiotic resistance phenotypes for genetic analysis. In the case of the Tn5 derivatives the insertion is reportedly stable for only 5–15 generations (Pappas, K. M., et seq. P. 383, FIG. 1.) Moreover, site-specific insertion through homologous recombination in *Z. mobilis* was not demonstrated, and no bacteriophage has ever been isolated from *Zymomonas*.

Transposons Tn5 and Tn10 are well known and have been widely used for mutagenesis and insertion of cloned DNA into a variety of gram-negative bacteria. In Herrero, M., et al., (1990) (J. Bacteriol. 172:6557–6567), a procedure is described for cloning and stable insertion of foreign genes into the chromosome of gram-negative eubacteria by combining two sets of plasmids, (i) the transposition features of Tn10 and Tn5, (ii) the resistance to certain compounds, and (iii) the suicide delivery properties of the R6K-based plasmid pGP704. The resulting constructions contain unique NotI or SfiI, sites internal to either the Tn10 or the Tn5 inverted repeats. These sites are used for cloning DNA fragments with the help of two additional specialized cloning plasmids, pUC18Not and pUC18Sfi. The newly derived constructions are maintained only in donor host strains that produce the R6K-specified p protein, which is an essential replication protein for R6K and plasmids derived therefrom. Donor plasmids containing hybrid transposons are transformed into a specialized lpri lysogenic *E. coli* strain, such as *E. coli* Sm10(lpir), with a chromosomally integrated RP4 that provided broad-host range conjugal transfer functions. Delivery of the donor plasmids into selected host bacteria is accomplished through mating with the target strain. Transposition of the hybrid transposon from the delivered suicide plasmid to a replicon in the target is mediated by the cognate transposase encoded on the plasmid at a site external to the transposon. Since the transposase function is not maintained in the target cells, such cells are immune to further transposition rounds. Multiple insertions in the same strain are therefore only limited by the availability of distinct selection markers.

Herrero, M. et al., (1990), (Journal of Bacteriol. 172(11): 6568–6572), relates to the construction of a collection of Tn5-derived minitransposons, such as Tn5Tc. It may be possible to employ the Tn5-derived minitransposons, such as Tn5Tc, to incorporate foreign DNA fragments into the genome of a variety of gram-negative bacteria. The minitransposons consist of genes specifying the resistance to kanamycin, and tetracycline as selection markers and a unique NotI cloning site flanked by 19-base-pair terminal repeat sequences of Tn5. The transposons are located on a R6K-based suicide delivery plasmid that provides the IS50R transposase tnp gene in cis but external to the mobile element and whose conjugal transfer to recipients is mediated by RP4 mobilization functions in the donor. Therefore, insertions produced by these elements are generally more stable because of the absence of transposase-mediated secondary transpositions, deletions, and inversions. See also, Berg et al., (1989) Transposable elements and the genetic engineering of bacteria, p.p. 879–926, in D. E. Berg, Mobile DNA, American Society of Microbiology, Washington, D.C. Stable insertions can in this way be obtained with elements derived, for instance also from Tn10. Way, J. C. et al., (1984) (Gene 32: 369–379).

The structure of mini-Tn5Tc, Herrero, et seq., p. 6569, is described for use for insertion mutagenesis or as a transposon vector for the cloning of DNA fragments flanked by NotI sites (isolated by cloning DNA fragments first into the pUC18 derivatives pUC18Not and pUC18Not). The Mini-Tn5Tc element is constructed, in vitro, using standard recombinant DNA techniques. Maniatis, T., et al., (1989) Molecular cloning: a laboratory manual. Cold Spring Harbor Laboratory, Cold Spring Harbor, N.Y. The determinant for tetracycline (Tc) resistance is obtained as an EcoRI fragment from plasmids bearing them as an interposon. Fellay, R., et al. (1987) Interposon mutagensesis of soil and water bacteria: a family of DNA fragments designed for in vitro insertion mutagenesis of Gram-negative bacteria. Gene 52: 147–154. The fragment is subsequently cloned into a single EcoRI site of pUC18Sfi, excised as an SfiI fragment, and inserted between the Tn5 19-base pair termini in pUT so that the mobile unit is present in all cases as an XbaI-EcoRI (partial) portion of the delivery plasmid. The resulting element is mini-Tn5Tc.

Tn10-based transposon vector delivery systems are described generally in Herrero, M. et seq. 172:6557–6567. Phage 1, a derivative IRP167, carries a 5.1-kb EcoRI insert containing the mini-Tn10 Km element and the transposase gene of IS10R is located outside the inverted repeats of the mobile element and downstream of the PTac promoter. To obtain a transposon delivery plasmid with a host-independent regulation of its transposition, the EcoRI insert fragment is ligated to pBOR8, a derivative of pGP704 containing laclq gene from plasmid pMJR1560. This plasmid is unable to replicate in host strains devoid of the R6K-specified p protein product of the pir gene. pGP704 contains the conjugal transfer origin (oriT sequence) of the RP4 plasmid and can therefore be transferred to gram-negative bacterial when provided in trans with mobilization (Mob) functions. The MluI fragment internal to the inverted repeats containing the original-specified p protein product of the original kanamycin resistance gene of the mini-Tn10 is replaced by a fragment containing a SfiI-Ptt cassette, appropriately modified by the addition of the NotI site and the MluI adapters, which produced the pLODPtt. This construction has unique SfiI, NotI, and XbaI cloning sites between the mini-Tn10 inverted repeats. The Ptt resistance marker (Ptt$^r$) of pLOFPtt is exchanged by kanamycin resistance to produce plasmid pLOFKm.

Difficulty continues to exist in the area in genetic manipulation of *Zymomonas mobilis* to produce genetically stable strains that contain the genetic components necessary for pentose sugar fermentation in ethanol production. The genetic components necessary to permit *Zymomonas* to utilize pentose sugars would encode xylose isomerase, xylulokinase, transaldolase and transketolase.

In view of the foregoing, a need exists for the construction of stable recombinant *Z. mobilis* strains which are capable of fermenting pentose sugars, such as xylose and arabinose, or both, to ethanol. A need therefore exists for the generation of stable genomic inserts that encode the enzymes necessary for pentose sugar catabolism. A need continues to exist for commercially suitable strains of such *Zymomonas*, which means that such strains should also be free of antibiotic resistance, and stable for at least 40 generations or more in non-selection media. Commercially valuable strains must also preferably demonstrate a high specific rate of product formation at close to maximum theoretical product yield. These and other deficiencies in the art of microbial ethanol production are addressed with the present invention.

SUMMARY OF THE INVENTION

It is an object of the present invention to provide a method for preparing a stable *Zymomonas* integrant that includes foreign structural genes encoding enzymes needed to utilize and ferment a pentose sugar. In some embodiments, these enzymes are selected from the group consisting of xylAB, tal/tkt, and araBAD. At least one regulator gene for induction of the structural genes, into the *Z. mobilis* genome is to be included in yet other embodiments of the construct.

It is a further object of the invention to provide improved *Z. mobilis* strains capable of stable expression of structural genes encoding enzymes necessary for pentose sugar utilization, in a non-selection medium (i.e. in the absence of antibiotic or antibiotic resistance markers).

It is yet another object of the invention to provide improved, chromosomally or native plasmid modified *Z. mobilis* strains, having stable expression of the structural genes, and that provide a high rate of specific product formation and conversion efficiency. The stable *Zymomonas* integrants of the present invention demonstrated stability after from 80 to 160 generations. In yet another embodiment, the invention provides an improved biocatalyst for use in a cellulose hydrolysate reaction mixture. These biocatalysts are the recombinant *Zymomonas* described as part of the present invention.

The present invention also provides a transposon that is useful for stable insertion of foreign genes into a bacterial genome. In one embodiment, the transposon comprises: at least one operon having structural genes encoding enzymes selected from the group consisting of xylAxylB, araBAD and tal/tkt, and at least one promoter for expression of the structural genes in the bacterium, a pair of inverted insertion sequences, the operons contained inside the insertion sequences, and a transposase gene located outside of the insertion sequences. In another aspect, the invention provides a plasmid shuttle vector capable of transforming a bacterial Zymomonas genome with pentose-fermenting enzyme encoding genes. In some embodiments, the plasmid shuttle vector comprises at least one operon having structural genes encoding enzymes selected from the group consisting of xylAxylB, araBAD and tal/tkt, at least one promoter for expression of the structural genes in the bacterium, and at least two DNA fragments having homology with a gene in the bacterial genome to be transformed. In yet another embodiment, the present invention provides methods for integrating at least two operons containing pentose sugar fermenting enzyme encoding genes. By way of example, these two operons are PgapxylAB and Penotaltkt or Pgaptaltkt. The complex restriction system of the Zymomonas mobilis ATCC31821 strain may be used to create a stable pentose-fermenting strain in yet another embodiment of the present invention. In another embodiment, the transposon and shuttle vectors are used in constructing improved and stable Zymomonas mobilis strains that ferment pentose sugar-containing substrate to ethanol. A method for converting cellulose derived pentose sugars into fuels and chemicals is also provided using the genetically modified Zymomonas that are stable for expression in a non-selection medium.

The invention in a particular aspect provides for a process for using a genetically modified Zymomonas producing ethanol from a pentose sugar.

In a particular embodiment, the process comprises: preparing an integrant Zymomonas strain comprising stably incorporated genes encoding at least four pentose sugar fermenting enzymes, xylose isomerase, xylulokinase, transaldolase, and transketolase, wherein said integration comprises at least two integration events comprising a first homologous recombination step with a first operon to incorporate genes encoding a first and second pentose sugar fermenting enzymes and a second transposition step with a second operon to incorporate genes encoding a third and fourth pentose sugar fermenting enzymes, adding the integrant Zymomonas strain to a feedstock comprising a pentose sugar, and fermenting the pentose sugar to provide a composition comprising ethanol.

In some embodiments, the pentose sugar comprises xylose, arabinose or a combination. Thereof, the pentose sugar in some embodiments may be further described as being derived from a biomass. Particular aspects of the process is further defined as employing a Zymomonas mobilis strain ATCC31821. The integrant Zymomonas mobilis strain of the invention may be defined as a Z. mobilis ATCC31821 Penotaltkt/PgapxylAB integrant. By way of example, specific integrants are designated int2/321, int2/1821, x9t(enott)Pi#4, x9t(enott)Pi#8, 321(5), 481, 2032, 2122, 8b and 321-a.

In some embodiments, the invention provides Zymomonas integrants and derivatives thereof capable of fermenting pentose sugars (xylsoe, arabinose) to ethanol in the presence of relatively high concentration of acetate or acetic acid. By way of example, the invention provides integrants that successfully produce ethanol in the presence of acetate or acetic acid at a concentration of 2, 4, 8, 10, 12 and even up to 16 g/L.

The invention in another embodiment provides for an integrant Zymomonas capable of fermenting a pentose feedstock to ethanol. Particular examples of the integrant are: int2/321, int2/1821, x9t(enott)Pi#4, x9t(enott)Pi#8, 321(5), 481, 2032, 2122, 8b and 321-a.

In another embodiment, the mannose utilizing gene (manA) is provided on a plasmid and the plasmid is used to transform Zymomonas mobilis ATCC31821 and 39676, generating mannose-fermenting Zymomonas strains. The same transformation method is applied to the integrants mentioned in this invention to generate Zymomonas strains capable of fermenting xylose and mannose, or xylose, arabinose and mannose in a biomass.

In yet another embodiment, the mannose-utilizing gene (manA) and any other genes necessary for mannose utilization is integrated in the genome of Z. mobilis ATCC31821, 39676, derivatives of these and the integrants mentioned herein, generating Z. mobilis integrants strains capable of fermenting xylose and mannose, or xylose, arabinose and mannose in a biomass.

Additional advantages of the present invention will be set forth in part in the description that follows and in part will be obvious for that description or can be learned from practice of the invention. The advantages of the invention can be realized and obtained by the method particularly pointed out in the appended claims.

BRIEF DESCRIPTION OF THE DRAWINGS

The accompanying drawing, which are incorporated in and which constitute a part of the specification, illustrate at least one embodiment of the invention and, together with the description, explain the principles of the invention.

FIG. 6 is a graph of the enzymatic activities for several isolates of the stable xylose fermenting Z. mobilis strain, Wherein

FIG. 7 illustrates graphs of the fermentation profiles for four of the isolates (nos. 21, 22, 5, and 11) of FIG. 6 and their performance in relation to the plasmid bearing strains 39673/pZB4 and BC1/pZB4L.

FIG. 8 is a graphic representation which illustrates the stability of the stable xylose fermenting Z. mobilis strains C25 and D92, wherein

FIG. 12 shows Southern analysis of the genomic integrated xylose/arabinose-fermenting *Z. mobilis* strains from homologous recombination using DIG-ara and DIG-ldh probes. AX1, 13, 23, 101, 104, and 107 are araBAD integrants. C25 is the host control PZB1862-ldhL-ara is the plasmid control isolated form DH5α.λ/H is a molecular weight marker: 23, 9.4, 6.6 4.3, 2.3 and 2.0 kb; wherein 12A uses the probe ara and 12B uses the probe ldh.

FIG. 13 represents a Southern analysis of the genomic integrated xylose/arabinose-fermenting *Zymomonas* strains from transposon integration using DIG-tnp and DIG-ara probes. G5, 6, 11, 15, 17, 14 and 19 area araBAD integrants. C25 is the host control. Tn10G is the plasmid control. λ/H is a molecular weight marker: 23, 9.4, 6.6, 4.3, 2.3 and 2.0 kb; wherein FIG. 13A is the tnp probe and PstI digestion, and FIG. 13B is the ara probe and PstI digestion.

FIG. 16 represents a bar graph result of the ethanol process yields of the genomic integrated xylose and arabinoses-fermenting *Zymomonas* strains on RMGXA (1:2:2%) at T=30° C., without pH control. These strains were inoculated from cultures at various generations on non-selective media.

FIG. 31 is an illustration of stability test.

DETAILED DESCRIPTION

Figure 1:
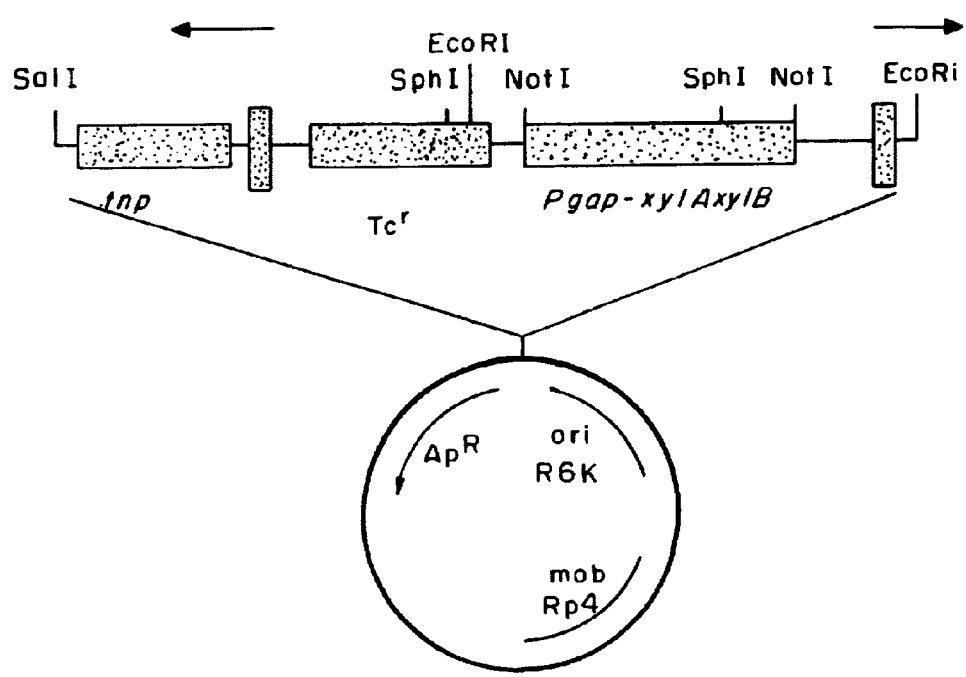
FIG. 1 is a plasmid map of Mini-Tn5 Tc in pGP704 containing the xylose assimilation operon according to the present invention.
Figure 2A:
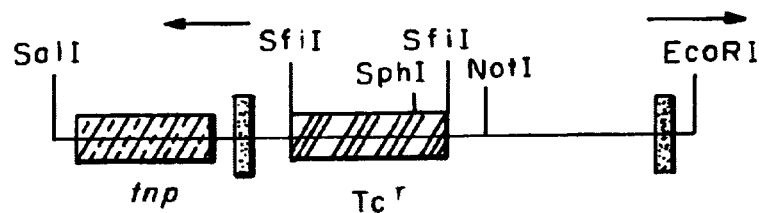
FIG. 2 is a series of plasmid maps illustrating the mini-Tn5 series constructs, wherein 2(a) shows the mini-Tn5-Tc prior to obtaining the Tc$^r$ transconjugates; 2(b) shows Zymomonas Tc$^r$ transconjugates were obtained from both SM10λpir donors containing Mini-Tn5Tc xylAxylB (X4) and Mini-Tn5 xylAxylB (X5) by selection on media containing Tc and nalidixic acid.
FIG. 2(c) shows Mini-tn5-Tc-xylAxylB was partially and completely digested with Sfi I and ligated to the Peno-talB/tktAsfi fragment.
FIG. 2(d) shows complete digestion yielded a plasmid without the Tc$^r$ gene, designated as miniTn5-tal/tkt-xylAxylB.
Figure 2B:
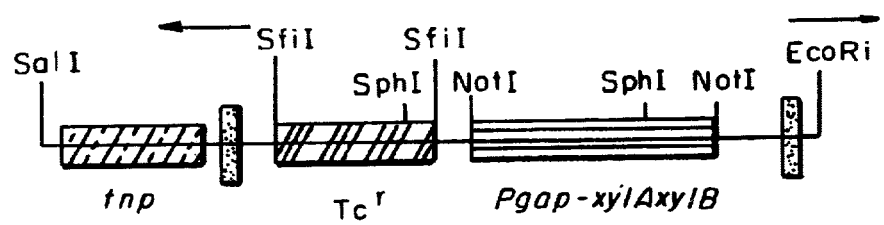
Figure 2C:
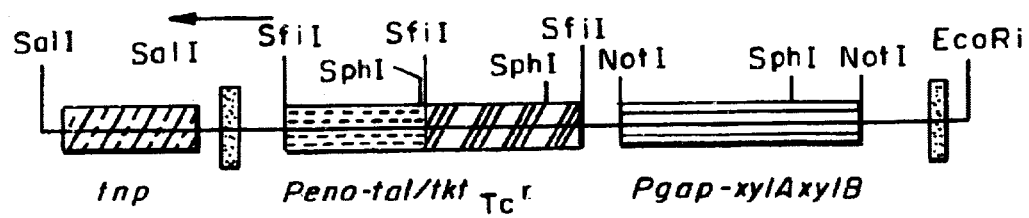
Figure 2D:
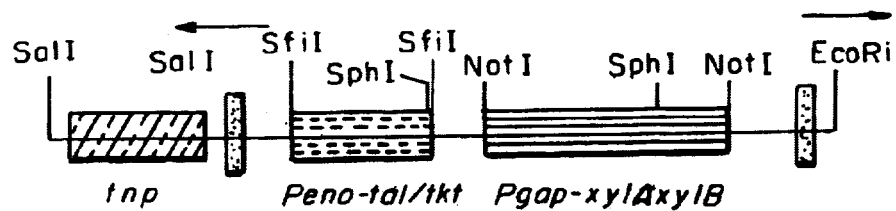

Unless specifically defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All US patents are incorporated by reference as though fully set forth herein.

With respect to the construction of a genetically stable Z. mobilis ATCC31821 for pentose utilization, two integration methods were developed which include homologous recombination and transposition. Two operons, PgapxylAB and Penotaltkt (or Pgaptaltkt), were constructed so that each could be integrated as a single cassette. Preferably, each operon includes an antibiotic resistance gene for the selection of the integrants.

With regard to homologous recombination, integration of the $P_{gap}$xylAB operon in ldh of strain 31821 used in a 4 kb DNA fragment as homology target having a 1-kb ldh region flanked by pgm and adhI genes. This homologous DNA fragment is designated as ldhL4. Fragment ldhL4 was amplified as two DNA fragments (5'ldhLR and 3'idhL4) using Pfu polymerase using 31821 DNA as temperate and re-assembled through cloning in vector pZB1861. NotI and SfiI sites were introduced during PCR for the subsequent cloning of $P_{gap}$xylAB and Tc$^r$ (See Examples below). The primers were designated based on the DNA sequence of Z. mobilis CP4 (Yamano et al (1993) J. Bact. 175:3926–3933).

With regard to transposition, strain 31821 was found to have restriction system(s), which degrades methylated DNA introduced into the host cells. Transposition using MiniTn5Tc via E. coli Sm10(λpir) as donor host was not successful. As such, integration of $P_{eno}$taltkt or Pgaptaltkt operon was accomplished using EZ::TN™ Insertion Kit (Epicentre, Wisconsin), in which an efficient transposase (Tn5-based) and a vector (pMOD) carrying genetically improved insertion sequences (Mosaic ends) was provided. Using the kit, host cells were transformed using transposomes (transposase-bound $P_{eno}$taltkt or Pgaptaltkt) where DNA were prepared from a methylation-deficient host or native Z. mobilis 31821 plasmids integrated with $P_{eno}$taltkt.

Although the description and Examples below are specific to integration of two operons into the genome of Z. mobilis, the methods of the present invention may be modified to independently integrate each of the four pentose utilization genes, where each gene is under the control of its own promoter. In addition, any number of promoters can be used in the context of the present invention for expression of the target genes, as long as the promoter directs expression of the xylose utilization genes in Z. mobilis.

Reference now will be made in detail to the presently preferred embodiments of the invention, examples of which are illustrated in the accompanying drawings. For the examples described below, "plasmid-bearing strains" refers or relates to those strains and vectors described in the US patents identified in the Description of the Related Art. "Z mobilis genome, or genomic" means the genes which, in toto, specify all the expressed and potentially expressible with a given Z. mobilis.

EXAMPLES

Strains, Plasmids, and Media

E. coli bacterial strains C118λ(pir), CC118(pir) (mini-tn5Tc), SM/0λ(pir), and plasmids pUC19, pLOF/Km, pUC18sfi, pUT/Tc containing minitransposon Tn5, Tn 10 and pUC18 were obtained from Dr. K. Timmis, GBF—Gesellschaft Fur Biotechnololgische Forschung mbH, Mascheroder weg 1 D-38124 Braunschweig, Federal Republic of Germany. E. coli DH5α (Life Technologies) was used as a host for the construction of the plasmids. E. coli SM10λpir was used as donor strain in mating experiments. Strains of Z. mobilis ATCC 39676 and its derivative, 206C (U.S. Pat. No. 5,843,760) were used s recipients in accordance with the invention. Tn10-based plasmids were constructed and maintained in E. coli CC118. Integrative plasmids were used to transform methylation-deficient E. coli hosts such as JM110 and DM1 before the transformation in Z. mobilis ATCC 31821 host or its derivetive 5C, which was obtained by curing the plasmid from 31821/pZB5.

E. coli strains were cultured in LB medium at 37° C. with shaking (200 rpm). Z. mobilis strains were maintained anaerobically in RM (10 g/L yeast extract, 2 g/L KH$_2$PO$_4$) supplemented with 20 g/L glucose, D-xylose or L-arabinose, unless otherwise specified. All strains containing plasmids were grown in the presence of the appropriate antibiotic, tetracycline (Tc), 10 μg/ml in liquid for Z. mobilis and E. coli, 20 μg/ml in agar for Z. mobilis and 15 μg/ml in agar for E. coli; ampicillin (Ap), 100 μg/ml for E. coli; chloramphenicol (Cm), 120 μg/ml for Z. mobilis and 100 μg/ml for E. coli. For regeneration and selection of Z. mobilis transformants or transconjugates, mating plates ((MMG or MMX; 10 g/L yeast extract, 5 g/L tryptone, 2.5 g/L (NH$_4$)$_2$SO$_4$, 0.2 g/L K$_2$HPO$_4$ and 50 g/L sugar)) supplemented with tetracycline or nalidixic acid (20 μg/ml) were used. All agar plates were made with 15 g/L agar.

In some cases, integrants containing all four genes (xylA, xylB, tal and tkt) were grown in xylose medium. Integrants were transferred from RMGTcCm into RMX (1:50) and cultured at 30° C. For adaptation in RMX, xylose-grown cultures were transferred into fresh RXM whenever the estimated exponential stage was reached. The growth was monitored routinely by OD600 measurement in a Spectronic 601 (Milton Roy).

Plasmid pZB701 was constructed by cloning a DNA fragment containing PpdcmanA in a shuttle vector pZB 188. The Ppdc and structural gene of ManA were amplified using PCR individually and combined by a third PCR (overlap extension PCR) to precisely fuse the 5' transcriptional and translational regulation region including promoter RBS and the start codon of the PDC gene to the manA structural gene.

Recombinant DNA Techniques

Plasmid DNA isolation, restriction endonuclease digestion, ligation and transformation, agarose electrophoresis and other recombinant DNA techniques were carried out in accordance with published protocols, Sambrook et al., (1989), *Molecular cloning: a laboratory manual*, Cold Spring Harbor laboratory press, Cold Spring Harbor, N.Y., or the respective reagent manufacture's instructions, were specified, and are well known in the art. Genomic DNA of *Z. mobilis* was extracted using three-milliliters of overnight cells resuspended in 250 ml of 50 mM Tris-50 mM EDTA buffer. The cells were treated with lysosome at 37° C. for 30 min 100 ml of 5% SDS solution and RNAase (final concentration equal to 20 ng/ml) were then added and incubated for an additional 30 min. A phenol-chloroform extraction was performed twice, to remove the proteins. Genomic DNA was recovered by ethanol precipitation. Alternatively, genomic total DNA of *Z. mobilis* was extracted using Puregen kits (Gentra System, MN). Plasmid DNA extraction was carried out using Qiaprep Spin Miniprep kits (Qiagen, Calif.).

Conjugation, Transposition and Transformation

Plasmids were transferred from donor strains *E. coli* SM10λpir or S17-1 into *Z. mobilis* strains by conjugation with a filter mating technique (Conway et al., 1987).

In some cases a commercially available kit, EZ::TN™ Insertion Kit was used to generate transposomes for the transposition. Plasmid pMODP$_{eno}$talktktCm was treated with transposase according to the manufacturer's protocols with minor modifications. For in vitro transposition, integrative plasmids were treated with transposase at 37° C. for 2 hours in the presence of native plasmids (target DNA) of *Z. mobilis* 31821. The reaction was then heated at 70° C. for 10 minutes in the presence of 0.1% SDS and dialyzed against 5% glycerol and 5 mM Tris (pH 7.6) before transformation in *Z. molilis* 31821. For in vivo transposition, integrative plasmids were treated with transposase at room temperature for one hour followed by electroporation (Bio-Rad Gene Pulser, 0.1-cm gap cuvettes, 1.6 kV, 200 ohms, 25 µFD). Electrocompompetent *Z. mobilis* or *E. coli* cells were prepared by collecting cells at OD600=0.4 to 0.6. Cells were washed once in ice-cold sterile water followed by 10% glycerol and concentrated for approximately 1000-fold. Competent cells were aliquoted and stored at −80° C.

Plasmid DNAs were also transformed into either *Z. mobilis* 39676 or *E. coli* cells by electroporation as described in Zhang et al., (1995) *Science* 267:240–243.

Southern Blot Analysis

DNA was transferred onto a nylon membrane using a Stratagene Posi Blot pressure blotter. DNA probes Tc, xylB, Tnp, and Tal were digoxigenin-UTP labeled by Polymerase Chain Reactions (PCR). The following primers were used for DNA labeling:

```
                                        (SEQ ID NO:1)
Tc:  5'-TTGCTAACGCAGTCAGGC-3'

(SEQ ID NO:2)
     5'-GAATCCGTTAGCGAGGTG-3'

(SEQ ID NO:3)
xylB 5'-TATGGGTTCAGCGGCATGAG-3'

(SEQ ID NO:4)
     5'-ATGGGCATGAGATCCATAGCC-3'

(SEQ ID NO:5)
Tnp  5'-TCCTAACATGGTAACGTTC-3'

(SEQ ID NO:6)
     5'-CCAACCTTACCAGAGGGC-3'

(SEQ ID NO:7)
Tal: 5'-CGTCTAAAAGATTTTAAGAAAGGTTTCGATATGACGGACAAA
     TTGACC-3'

(SEQ ID NO:8)
     5'-CATTTTGACTCCAGATCTAGATTACAGCAGATCGCCGATCAT
     TTTTTCC-3'
```

Prehybridization and hybridization were performed according to established protocols described in the Boehringer Mannheim hybridization kit.

Amplification Using Polymerase Chain Reaction (PCR)

For construction of various integrative plasmids for gene integration, the following fragments were amplified by PCR using Pfu polymerase (Stratagene, La Jolla, Calif.) and their appropriate primer pairs:

```
1. 5'IdhL4 (1.9 kb)
   Template: Z. mobilis 31821 DNA
   Primers:                             (SEQ ID NO:9)
   P16(F) 5'CCATCGATTCTAGAATCTCGCGTAATAAAACTATCAG
          GCGCAATCG3'
                                        (SEQ ID NO:10)
   P17(R) 5'CGCGGATCCAGATCTGGCCTAGGCGGCCTCATAATAT
          GGGCAAAGACACTCCCG3'

2. 3'IdhL4 (2.4 kb)
   Template: Z. mobilis 31821 DNA
   Primers:                             (SEQ ID NO:11)
   P18(F) 5'GAAGATCTGCGGCCGCGTTTTGGTGCCAATGTTATCG
          CC3'
                                        (SEQ ID NO:12)
   P19(R) 5'GAAGATCTAAGCTTGGATAGCGGCTTATAGCAACGAG
          TGC3'

3. Tc$^r$ (1.5 kb)
   Template: pBR322
   Primers:                             (SEQ ID NO:13)
   Tc(F) 5'AAAGGCCGCCTAGGCC3'
                                        (SEQ ID NO:14)
   Tc(R) 5'AAAGGCCTAGGCGGCC3'

4. Cm$^r$ (1 kb)
   Template: pZB186
   Primers:                             (SEQ ID NO:15)
   Cm(F, Eag) 5'CCGAATAAATACGGC-
   CGCCTGTGACGGAAGATC
            ACTTC3'
                                        (SEQ ID NO:16)
   Cm(R, Eag) 5'TAACGACCCTGCCGGCCGCCTGAACCGACGACC
              GGGTCG3'
```

Construction of pZB512XTc and pZB510xTc for Homologous Recombination

Figure 19A:
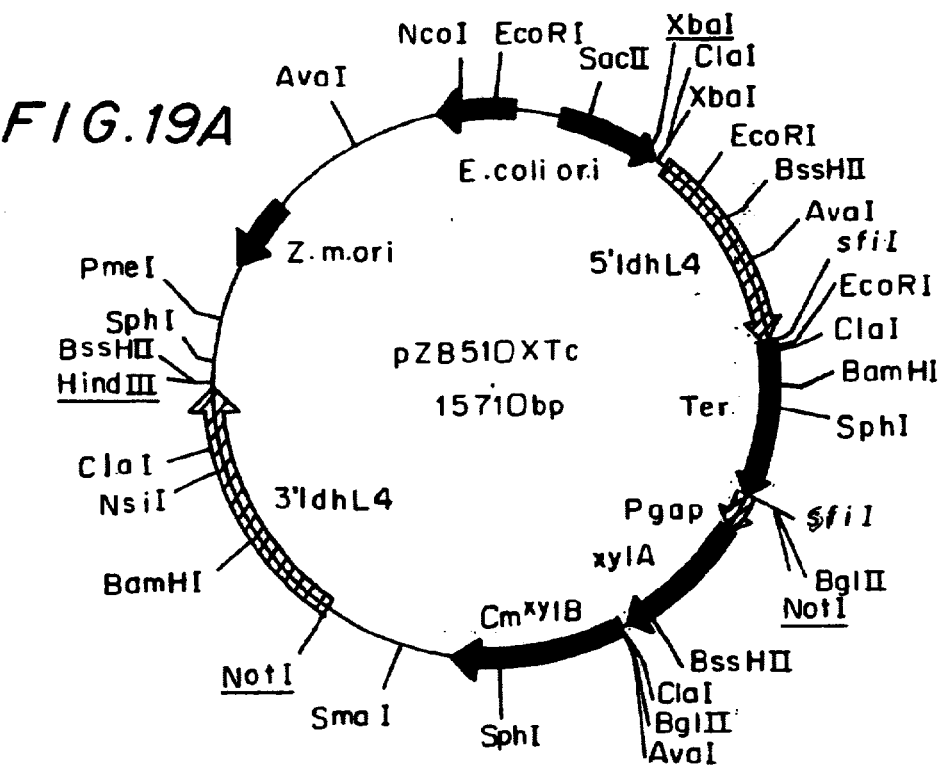
FIG. 19 shows plasmid maps for pZB510XTc (FIG. 19A) and pZB512XTc (FIG. 19B) for homologous recombination into *Z. mobilis* strain 31821.
Figure 19B:
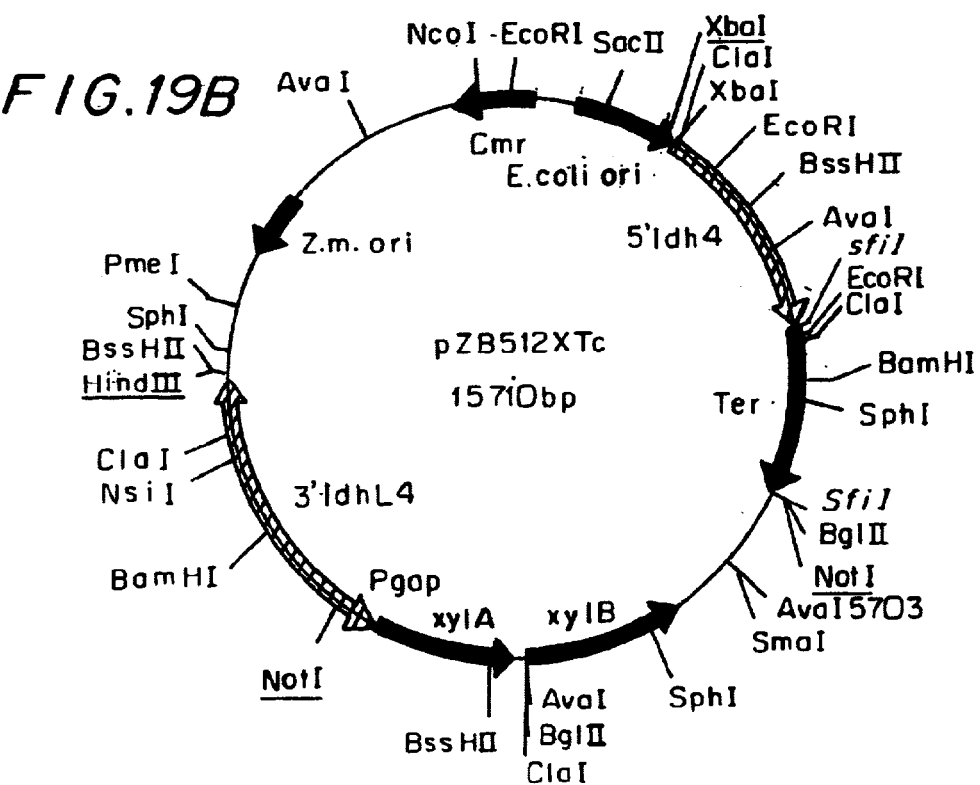

PCR-generated fragments 5'IdhL4 (1.9 kb) and 3'IdhL4 (2.4 kb) were sequentially inserted into BamHI-XbaI site and BamHI site of shuttle vector, pZB1861. The integrative plasmid pZB510xTc (see FIG. 19(A)) was then constructed by inserting $P_{gap}$xylAB (from pZB4) and $Tc^r$ (PCR product) in NotI and SfiI sites between 5'IdhL4 (1.9 kb) and 3'IdhL4 (2.4 kb) fragments. Plasmid pZB512XTc (see FIG. 19(B)) was constructed in a similar fashion except the orientation of the $P_{gap}$xylAB was opposite to that in pZB510XTc.

Construction of pMODP$_{eno}$taltktCm for Transposition

Figure 20:
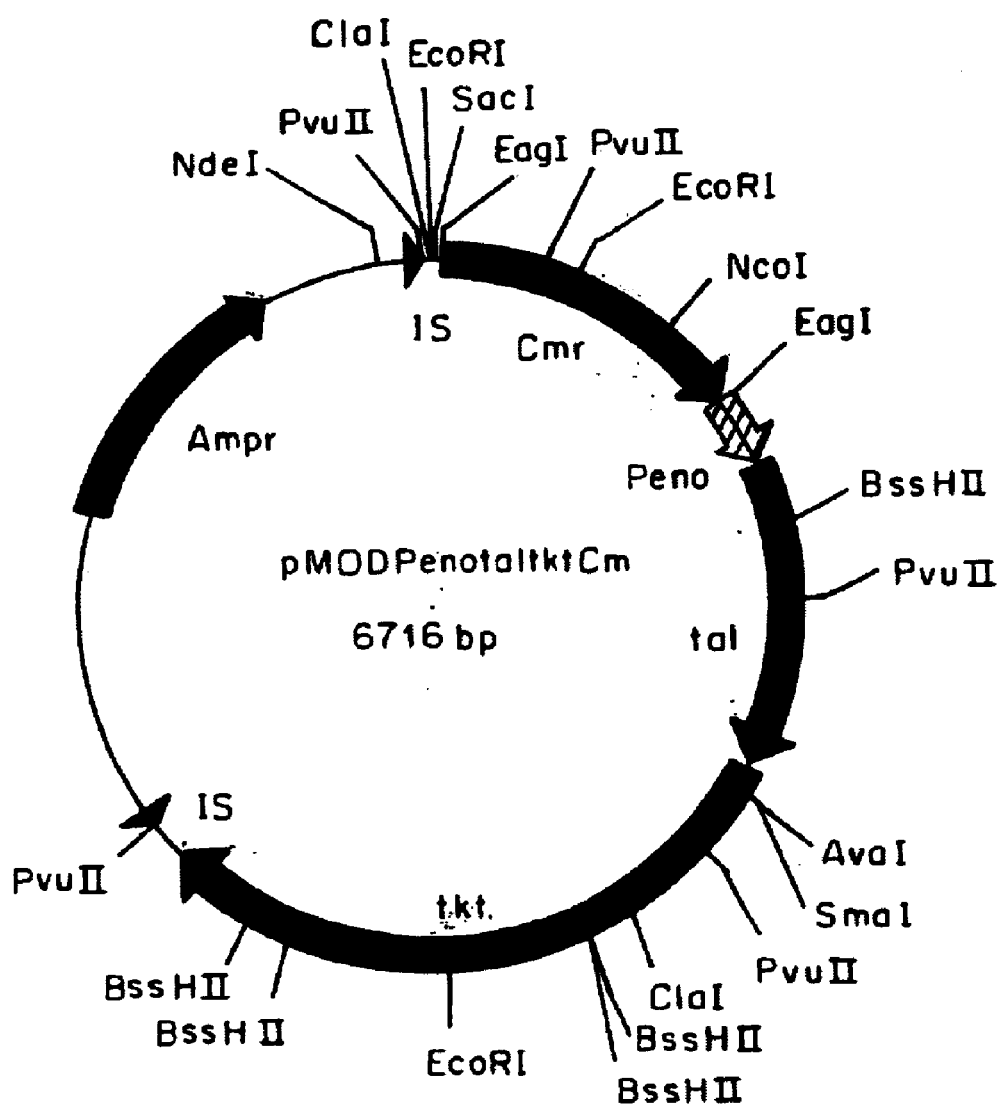
FIG. 20 is the plasmid map for $pMODP_{eno}taltktCm$ for integrative transposition into *Z. mobilis* 31821.

A PCR-generated $Cm^r$ fragment was cloned in the SmaI site of vector pMOD (Epicentre, WI) resulting in pMODCm. A BglII fragment from pUCtaltk (Zhang et al (1995) *Science* 267:240–243) was then cloned into pMODCm at BamHI site to form pMODP$_{eno}$taltktCm (see FIG. 20). The fragments cloned into pMOD are flanked by the two 19 bp Mosaic ends (IS), which can be recognized by transposase for transposition.

Plasmid Curing to Obtain xylAB Integrants from Homologous Recombination

Overnight cultures of *Z. mobilis* 5C/pZB512XTc grown in RMGTcCm (30° C.) were sub-cultured (1:100) daily in 5 ml RMG tubes at 37° C. for up to 10 transfers. At each transfer, cultures were plated and monitored for the loss of plasmid by comparing the colony numbers on RMG and RMGCm plates. When the population of plasmid-bearing cells is less than 10% of the total, cultures were inoculated (1:100) in RMGTc to enrich the growth of potential PgapxylABTc integrants. RMGTc enriched cultures were plated onto RMGTc plates and replica-plated onto RMGTc and RMGCm plates. Colonies with $Tc^rCm^s$ phenotype would be further analyzed to confirm the integration.

Enzymatic Assays

Xylose isomerase (XI), xylulokinase (XK), transketolase (TKT) and transaldolase (TAL) were assayed, in some cases, using cell-free extracts of *Z. mobilis* integrants and control strains according to Zhang et al., (1995) *Science* 267: 240–243 with modification. Cell-free extracts of *Z. mobilis* were prepared by collecting the cultures at late-log phase (30°, OD600 approx. 1.2) washed once with sonication buffer (10 mM Tris-Cl, pH 7.6, 10 mM $MgCl_2$) followed by sonication. Cell debris was removed by centrifugation (14,000 rpm, 45 min, 4° C.).

Example 1

The following example illustrates the construction of Mini-Tn5Tc containing genes encoding the xylose assimilation enzymes and the conjugal transfer of this construct into *Z. mobilis* 206C and ATCC 39676. Mini-Tn5Tc containing genes encoding the xylose assimilation enzymes was constructed by inserting a Pgap-xylAxylB operon into the unique NotI site of Mini-Tn5Tc contained in plasmid pGP704. See, FIG. 1. The Pgap-xylAxylB operons, were taken from plasmid pZB4 or pZB5, U.S. Pat. Nos. 5,712,133 and 5,726,053. The resulting plasmids, designated Mini-Tn5Tc xylAxylB (X4) and Mini-Tn5Tc xylAxylB (X5) were transformed into the donor strain *E. coli* SM10λpir by electroporation and mated with either *Z. mobilis* ATCC 39676 or 206C strains. *Z mobilis* 206C is disclosed in U.S. Pat. No. 5,843,760 which is incorporated herein by reference. Nine *Zymomonas* $Tc^r$ transconjugates were obtained from both SM10λpir donors containing Mini-Tn5Tc xyl-AxylB (X4) and Mini-Tn5 Tc xylAxylB (X5) by selection on media containing Tc and nalidixic acid. See, FIG. 2(*b*).

Genomic and plasmid DNA from the nine *Z. mobilis* $Tc^r$ transconjugates was then subjected to Southern blot analyses. Genomic and plasmid DNA from the transconjugates was digested with SphI, which cuts in the hybrid transposon and in the xylose operon, and the blots were then hybridized to either a Tc probe, a XylB probe, or a transposase Tnp probe. From the autoradiograph it was determined that (1) the xylose operon Pgap-xylAxylB had been inserted into the *Zymomonas* genome, along with $Tc^r$ gene; (2) only a single insertion had occurred for each of the transconjugates; (3) the insertions were each at a distinct location in the genome; (4) the $Tc^r$ gene and XylB were not present in the plasmid fraction; and (5) the tnp transposase gene was not present in transconjugates.

Enzymatic analysis of the *Zymomonas* $Tc^r$ Pgap-xyl-AxylB Transconjugates was made in order to confirm the expression of xylose isomerase (XI) and xylulokinase (XK) in the *Zymomonas* Tc Pgap-xylAxylB transconjugates. This analysis revealed that the enzymatic levels of xylose isomerase for all the transconjugates was about one-half that of their plasmid counterparts. Similarly, about one-half of the xylulokinase activities of the plasmid-bearing strains was observed in the integrants. Both XI and XK activities, expressed from a single copy of the genes, in the *Zymomonas* genome, were considerably higher than was expected, when compared to that of the 10 copies per cell found in a plasmid-bearing strains.

Example II (C25)

This example demonstrates the utility of a integration event method to create a *Zymomonas* integrant that express four pentose fermenting genes. A *Zymomonas* integrant with improved genetic stability in the absence of antibiotic selection is created by this proess. The xylose assimilation genes xylA and xylB, encoding xylose isomerase and xyluloki-nase, and pentose phosphate pathway genes, talB and tktA, encoding transaldolase and transketolase, need to be introduced into the *Z. mobilis* genome using mini-Tn5 in order to accomplish the creation of pentose-fermenting strains. Two operons containing Pgap-xylA/xylB and Peno-talB/tktA were assembled in mini-Tn5 and the resulting plasmid was conjugated into *Z. mobilis*. With the help of the transposase located outside of the mini-Tn5 cassette, single copies of the Pgap-xylAxylB and Peno-talB/tktA were inserted into the *Z. mobilis* genome, as shown by Southern hybridization. Enzymatic analysis of xylose isomerase, xylulokinase, transaldolase and transaldolase indicated that all the genes were coordinately expressed, and that the integrated strains produced about 30–70% of the enzymatic activities of the plasmid-bearing strains. These enzymatic levels were sufficient for the organism to grow and ferment a particular pentose, xylose, to ethanol.

Figure 3:
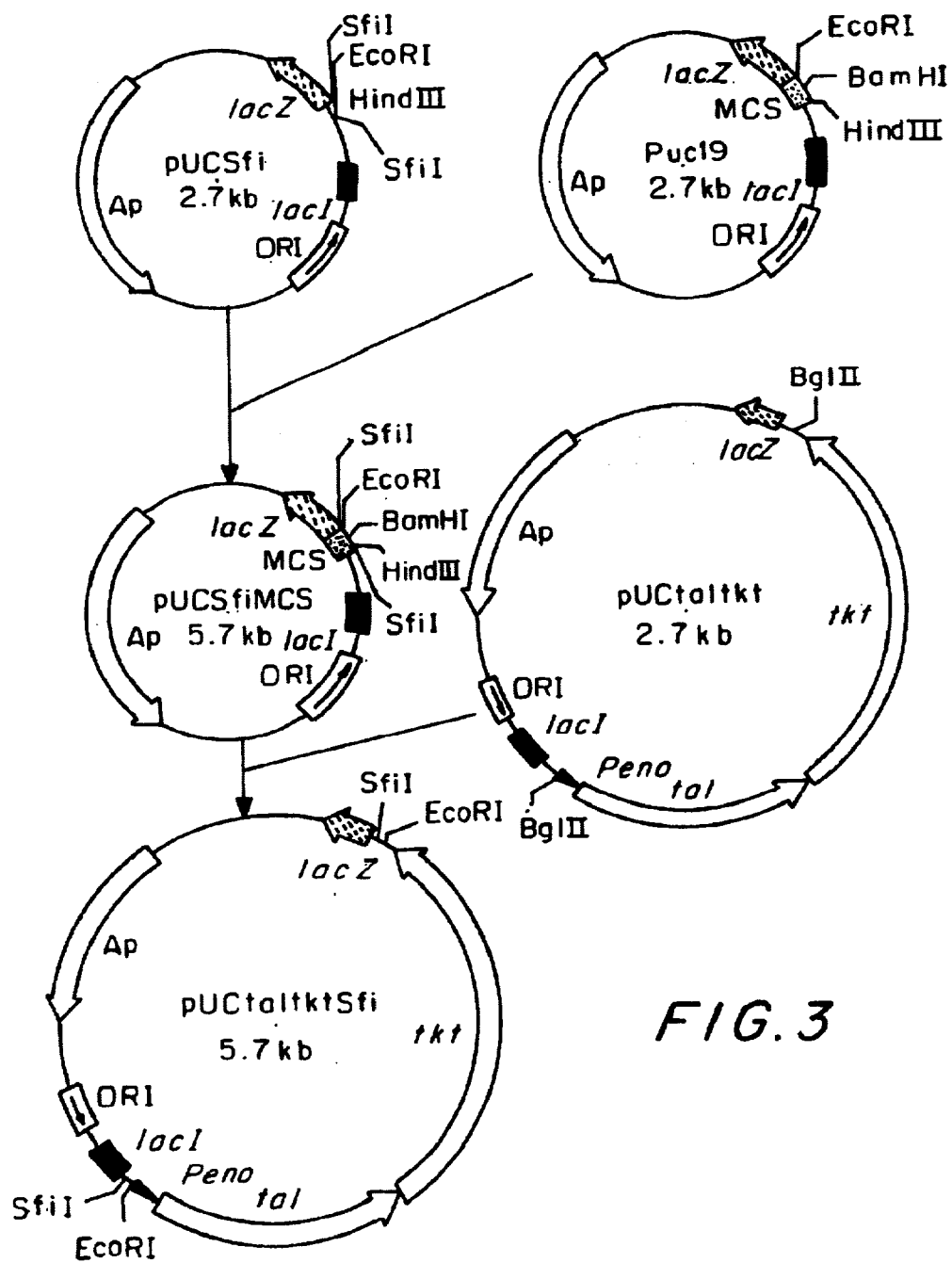
FIG. 3 is an illustration of the series of constructs resulting in the plasmid map of pUCtaltktSfi.

To facilitate the cloning process, the Bg/II fragment containing the operon Peno-talB/tktA was inserted into the BamHI site of a newly constructed auxiliary plasmid, pUS-CfiMCS as shown in FIG. 3. The auxiliary plasmid, pUS-CfiMCS, was constructed by inserting a EcoR I-Hind III fragment containing the multicloning sites from pUC19 into pUCSfi. PUCtaltkt was then constructed from pUCpfiMCS and pUCtaltktSfi, as shown in the FIG. 3.

Referring now to FIG. 2, the Peno-talB/tktA was then excised, from pUCtaltktSfi, as a SfiI fragment and was used to clone into mini-tn5-Tc-xylAxylB. As shown in the Figure, the $Tc^r$ gene is flanked by SfiI sites on the Tn5-Tc-xylAxylB cassette. Mini-tn5-Tc-xylAxylB was partially and completely digested with Sfi I and ligated to the Peno-talB/tktAsfi fragment, as shown in FIG. 2(c). The partial digestion yielded a plasmid containing the Tc$^r$ gene, designated as mini-tn5-Tc tal/tkt-xylAxylB ((FIG. 2(c)), while complete digestion yielded a plasmid, according to the invention herein, without the Tcr gene, designated as miniTn5-tal/tkt-xylAxylB. See FIG. 2(d).

Both plasmids were transformed into the donor strain E. coli, S17-1 and mated with Z. mobilis 206C. The resulting transconjugates were selected on mating media containing glucose, Tc, and nalidixic acid for miniTn5-tal/tkt-xyl-AxylB-Tc. For mini-tn5-tal/tkt-xylA/xylB, the transconjugates were directly selected on mating media, containing xylose and nalidixic acid. A number of Tc$^r$ transconjugates (glucose-grown) were obtained for mini-tn5-tal/tkt-xyl-AxylB-Tc. Several xylose-grown transconjugates were obtained for mini-tn5-tal/tkt-xylAxylB.

Preliminary batch cultures were tested statically, at 30° C. without pH control in bottles with 80 ml RM containing 2% xylose for their fermentation dynamics. Colonies, taken from RM+2% xylose plates, were cultured in an RM 2% xylose medium overnight at 30° C. until the culture had reached the stationary growth phase (optical density$_{600}$=0.1 at 500 nm). These were used as the inoculum. Xylose and ethanol were analyzed using a Hewlett-Packard 1090L HPLC equipped with an P 1047. A refractive index detector and a Biorad HPX-87H organic acid analysis column operating at 65° C., with a 0.01 N sulfuric acid mobile phase flow rate of 0.6 nm/min. The ethanol yield was calculated using either the weight of sugar fermented or the total available sugar in the medium. The maximum theoretical yield was based on 0.51 g ethanol/g xylose.

Figure 4:
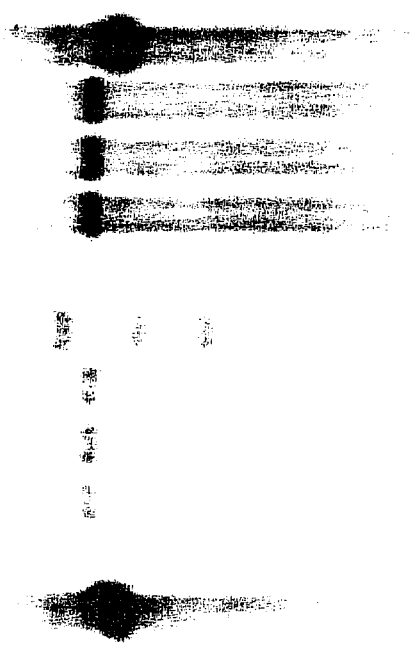
FIG. 4 is the results of the Southern analysis tal/tkt-xylAxylB Z. mobilis transconjugates with Tal probe. C is the control plasmid Tn5 tal/tkt-xylAxylB. λH is the DNA size marker.
Figure 5:
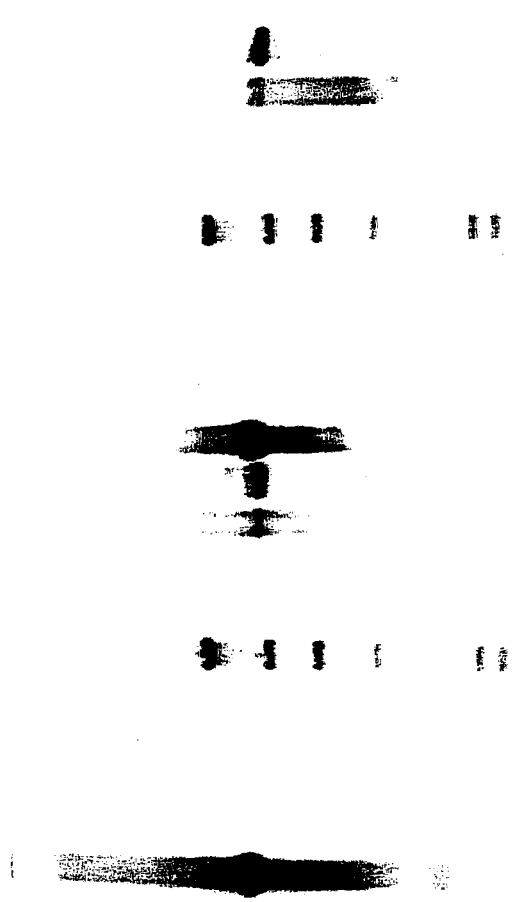
FIG. 5 is the results of the Southern analysis of tal/tkt-xylAxylB Z. mobilis transconjugates with Tnp probe. C is the control plasmid mini-Tn5 tal/tkt-xylAxylB. λ/H is the DNA size marker.

Southern hybridization analysis of genomic and plasmid DNA samples from the Z. mobilis transconjugates was done in order to dertermine whether transposition of the mini-tn5 tal/tkt-xylAxylB cassette had occurred. Genomic and plasmid DNA's prepared from four transconjugates of mini-tn5 tal/tkt-xylAxylB were digested with SphI. SphI cuts twice within the cassette yielding one fragment with Tal probe homology. The blots were then hybridized to either Tal probe or Tnp probe. The autoradiograph in FIG. 4 shows that one unique band greater than 4 kb (the size of Peno-talB/tktA), which is adjacent to Z. mobilis DNA, was detected from all the genomic DNA preparations when hybridized with Tal probe. Three of the samples (nos. 22, 23, and 24 possibly siblings) also showed a band in the plasmid fraction, suggesting that the integration had occurred in the native plasmid. Integration had occurred in the Z. mobilis genome for sample no. 21, and only one copy was inserted. Hybridization of genomic and plasmid DNA samples form these transconjugates with a Tnp probe (FIG. 5) revealed a lack of homology between the same DNA's and Tnp probe. These results suggested that the xylose assimilation and pentose phosphate pathway genes, along with Tc$^r$ gene, had been transposed into the Z. mobilis genome, and that only a singly insertion occurred in each of the transconjugates, and the insertions were at distinct locations in the genome.

Figure 6A:
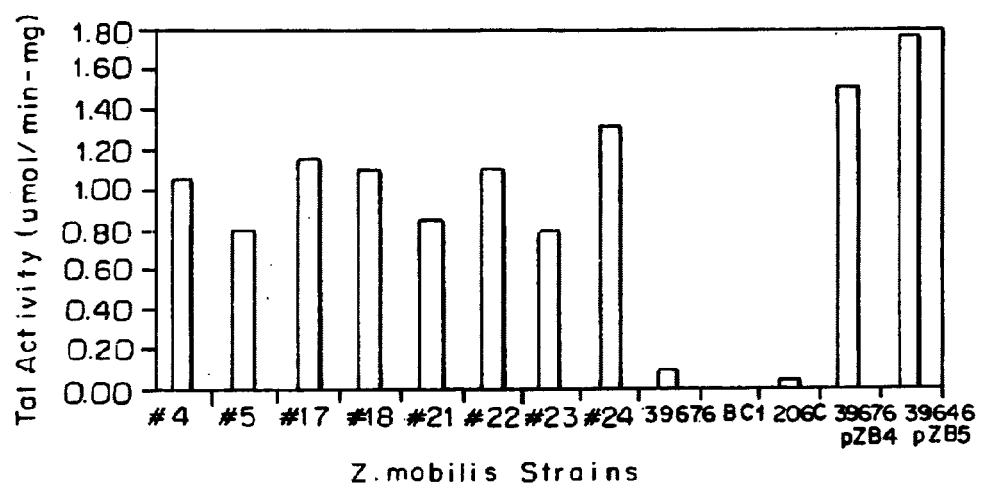
FIG. 6A shows that the enzymatic levels of TAL, for the transconjugates (nos. 4, 5, 17, 18, 21, 23 and 24), was about 50–70% that of their plasmid counterparts.
Figure 6B:
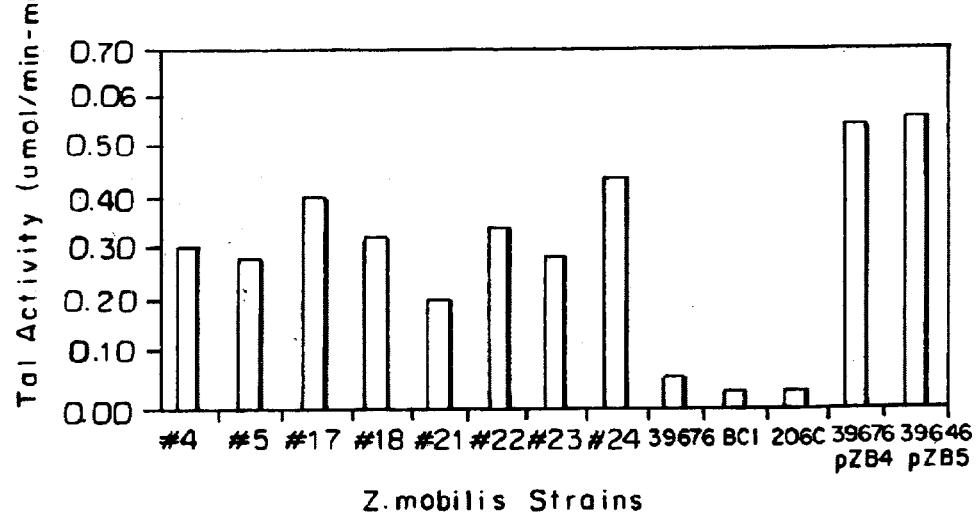
FIG. 6B shows that about 30–70% of the TKT activity of the plasmid-bearing strains was observed in the integrants.

Xylose isomerase, xylulokinase, transaldolase and transketolase activities were measured as previously described in (Zhang et al., 1995), for the Z. mobilis transconjugates. As set forth above, it had been observed that expression of a single Pgap-xylAxylB copy on the genome was about one-half that of the XI and XK enzymatic yield for the plasmid-bearing strains. However, when enzymatic analysis was done to confirm whether transaldolase (TAL) and transketolase (TKT) had been expressed in the Zymomonas tal/tkt-xylAxylB-Tc and tal/tkt-xylAxylB transconjugates, as shown in FIG. 6, it was revealed that the enzymatic levels of TAL, for the all the transconjugates (nos. 4, 5, 17, 18, 21, 23, and 24), was about 50–70% that of their plasmid counterparts. About 30–70% of the TKT activity of the plasmid-bearing strains was observed in the integrants. While the plasmid integrants had slightly elevated TAL and TKT activity both TAL and TKT activity, expressed from a single copy of the genes in the Zymomonas genome, were considerably higher than was expected when compared to that of the 10 copies per cell found on a plasmid-bearing strain.

All four of the tal/tkt-xylAxylB Zymomonas integrants (nos. 21, 22, 5, and 11) were able to grow on xylose. Preliminary fermentation studies for these integrants was then made using a 2% xylose substrate, at 30° C. The fermentation profiles, for these integrants, is shown in FIG. 7. In the Figure, the growth and sugar utilization rates of Z. mobilis integrant no. 21 was slower than that of the plasmid bearing strain 39676/pZB4. However, most of the Z. mobilis integrants (nos. 22, 5, and 11) were comparable to the plasmid-bearing strains. All the integrants produced ethanol from xylose, at 92% of the maximum theoretical product yield.

Figure 8A:
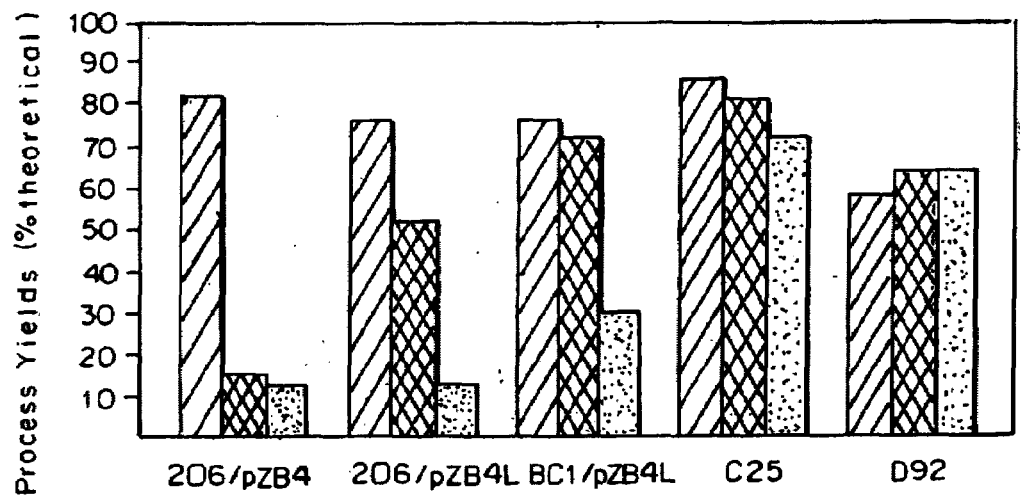
FIG. 8A shows the stability of the plasmid-bearing and genomic integrated xylose-fermenting strains, using the ethanol process yield and xylose utilization parameters as indicators; and that FIG. 8B shows Strains C25 and D92 remained stable for more than 90 generations.
Figure 8B:
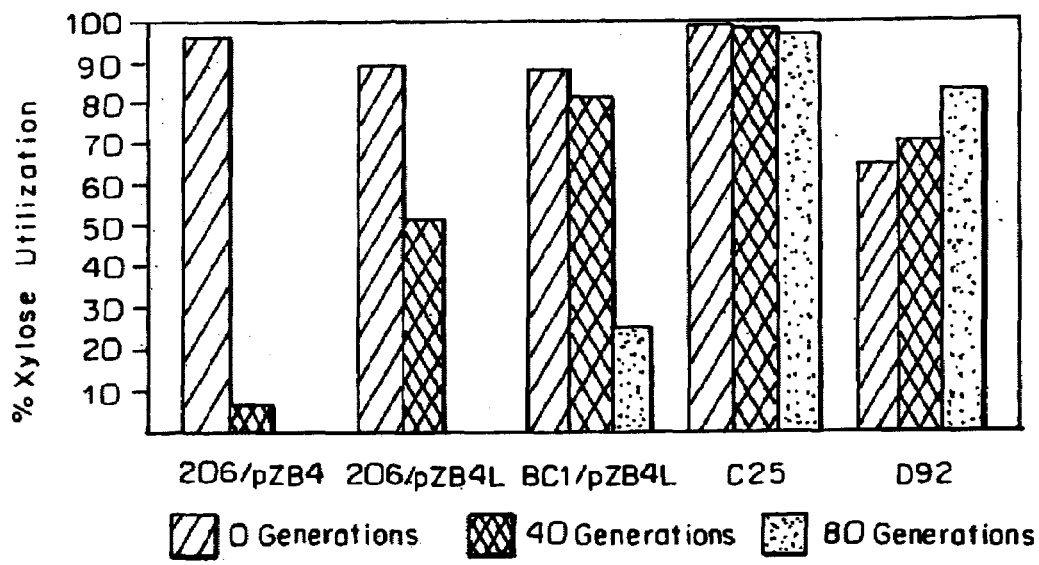

Stability of these genomic integrated strains and three plasmid bearing strains was measured in a non-selective medium. All strains were cultured in an RMG medium, and serially transferred about every 10 generations daily. At every 40 generations, the cells were used to inoculate a flask of RM media containing 1% glucose, and 5% xylose in order to measure their ability to ferment xylose to ethanol. Ethanol process yields and xylose utilization rates were used as the milestones for stability. Two of the genomic integrated strains demonstrated stability for more than 90 (C25 and D92) generations, while the plasmid-bearing strains (206/pZB4, 206/pZB4L and Bc1pZB4L) were stable for about 40 generations. See, FIG. 8.

Figure 9:
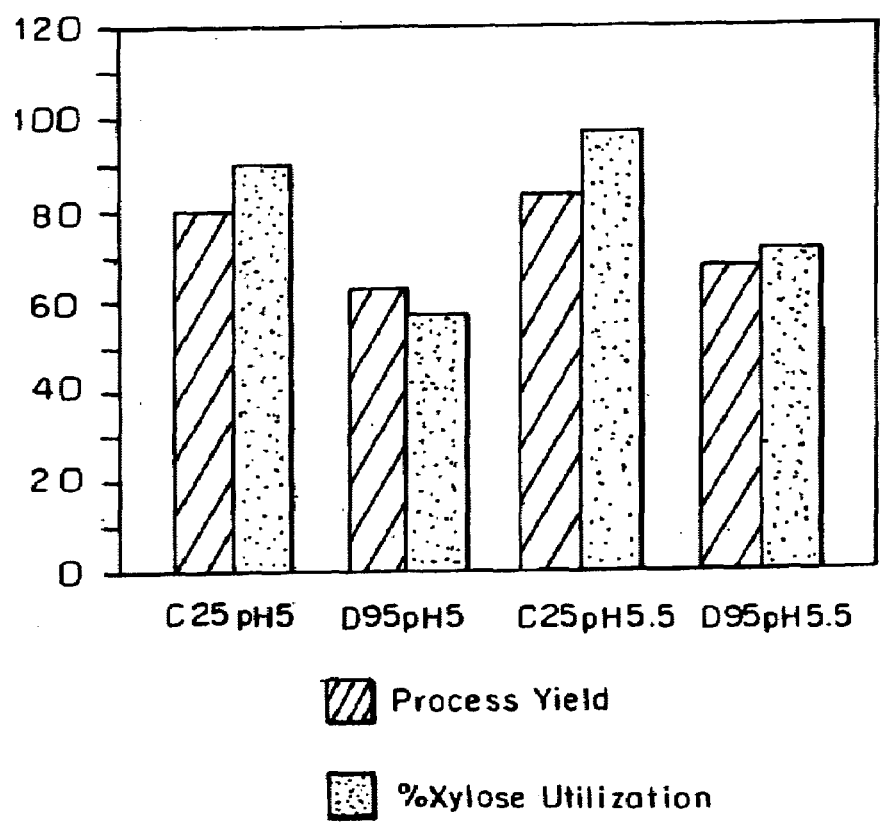
FIG. 9 illustrates the biomass concentration (a), ethanol concentration (b), xylose utilization (c), and process yield compared to % xylose utilization results for batch fermentation of the genomic integrated xylose-fermenting strains, C25 and D92, in a RM medium containing 4.5% glucose, and % xylose at pH 5.0 and pH 5.5 at 30° C., according to the present invention.

The fermentation performance of strains C25 and D95 analyzed in an RM medium contained a different concentrations of total glucose and xylose (1% glucose and 5% xylose; 3% glucose and 3% xylose; and 4.5% glucose and 4.5% xylose) under pH controlled conditions. As shown in the FIG. 9, strain C25 demonstrated greater xylose utilization and ethanol process yields at both pH 5, and pH 5.5 in RM containing 4.5% glucose and 4.5% xylose better than D92. In the subsequent examples the three arabinose assimilating genes (araBAD) were integrated into the C25 genome.

Example III (AX)

The following example demonstrates the introduction of the arabinose assimilation enzymes into the genome of C25 through homologous recombination via ldh and transposition using minitransposon Tn10. Plasmid pZB1862-ldhL-ara, described below, was used to transform Z. mobilis or E. coli by electroporation. Transformants were selected on mating plates supplemented with glucose and tetracycline. Tc$^r$ colonies were further confirmed to be Ara$^+$Xyl$^+$ by growth on RM supplemented with xylose or arabinose (RMX and RMA). Plasmid Tn10G, also described below, was transferred from an E. coli SM10λpir donor to Z. mobilis C25 by conjugation with a filter mating technique (Conway et al., 1987). The resulting transconjugates were selected on mating plates containing arabinose.

A. Construction of pZB1862-IdhL-ara and Integration in C25 using homologous Recombination.

Previous attempts to integrate araBAD in the Zymomonas genome, using a 1-kb ldh fragment as the homologous region, did not succeed. In order to increase the recombination frequency, a larger homology region was used. A 2.5-kb DNA fragment, which includes ldh and the flanking region was amplified using Pfu PCR. The primers were designed based on the DNA sequence of Z. mobilis CP4, published in Yamano I., (1993) *Journal of Bacteriology*, Vol. 175, 3926–3933. Although a 2.5-kb fragment was expected from PCR, a 3.4-kb fragment was obtained instead. After digesting the 3.4-kb fragment with BamHI, two fragments (2.5 and 0.9 kb) were obtained. Both fragments were tested by PCR, using primers designed to anneal to only the ldh. The 2.5-kb fragment produced a PCR product of the correct size, whereas the 0.9-kb fragment did not, indicating that the former contained the ldh sequence. Therefore, the 2.5-kb BamHI fragment (designated ldhL) was cloned and used as the homologous region for gene integration into C25.

The ldhL fragment was amplified by PCR using Pfu (Stratagene, La Jolla, Calif.) DNA polymerase (Qiagen, Valencia, Calif.). PCR product for ldhL is 2.5 kb. The following primer sequences were used:

```
ldhL:                                      (SEQ ID NO:17)
5'-TCGCGGATCCTCTATCCCTTTATTTTTCTATCCCCATCACCTCGG-
                                                                    3'

(SEQ ID NO:18)
5'-TCGCGGATCCGCGGCTGACATACATCTTGCGAATATAGGG-3'
```

Figure 10:
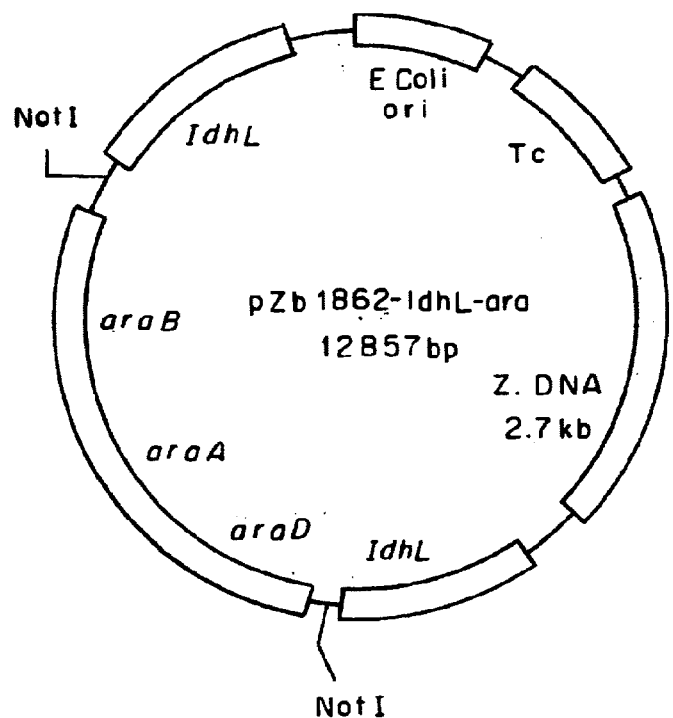
FIG. 10 is a map of the integrative plasmid pZB 1862-ldhL-ara. The araBAD is inserted in the NotI site of ldhL disrupting ldh. The construction is based on the replicative plasmid pZB 1862 of *Z. mobilis*.

For cloning purposes, a Not I site was introduced in ldhL by insertion of an oligonucleotide 5'-CATGCGCGGC-CGCC-3' (SEQ ID NO: 19) at NcoI site, which is located in the middle of the ldh gene. The new NotI site was approximately 1.4 and 1.1 kb from either end of the ldhL. A BamHI fragment of ldhL (2.5 kb) containing the NotI site was ligated into pZB1862 at a BclI site. Finally, a 4.4-kb Pgap-araBAD, isolated from pZB206 (U.S. Pat. Nos. 5,712,133 and 5,726,053), was cloned into the NotI site of ldhL, to form the integrative plasmid, pZB1862-ldhL-ara. See, FIG. 10.

The Pgap-araBAD operon, containing the three arabinose-assimilating genes, was integrated into the ldh site in the C25 genome through homologous recombination. To integrate the araBAD genes into the genome of C25, pZB1862-ldhL-ara was constructed in *E. coli* DH5α. The plasmid pZB1862-ldhL-ara was transferred into C25 by electroporation. The Tc resistant transformants were selected and tested for growth on arabinose. During propagation of the transformants, Pgap-ara-BAD could be integrated in the genome of C25 by the replacement of ldhL with the ldhL'-araBAD-ldhL' cassette (from the plasmid) through homologous recombination.

To enrich and isolate the integrants, plasmid curing was conducted for the transformants. Plasmid pZB1862-ldhL-ara will replicate in Z. mobilis. However, Z. mobilis tends to lose foreign plasmids at sub-optimal growth conditions (e.g., 37° C.). Using this characteristic, curing of pZB1862-ldhL-ara was achieved by subculturing C25 transformants at 37° C. in the absence of Tc for several transfers. Cultures from each transfer were constantly monitored for the loss of the plasmid. By the third transfer, 100% of the cells became $Tc^s$, indicating a loss of the plasmid. Cultures from the $3^{rd}$, $4^{th}$, $5^{th}$ and $6^{th}$ transfers were inoculated in RM containing arabinose (RMA), at 30° C., to enrich the growth of potential Pgap-araBAD integrants. The enriched cells were transferred to RMG plates and replica-picked onto RMA, RMX, and RMGTc plates. Several integrants (AX) with the phenotype of $Xyl^+Ara^+Tc^s$ were subjected to further analysis, as described below. These integrants were able to use xylose and arabinose as a sole carbon source.

B. Construction of Tn10G and Conjugation into C25.

Figure 11:
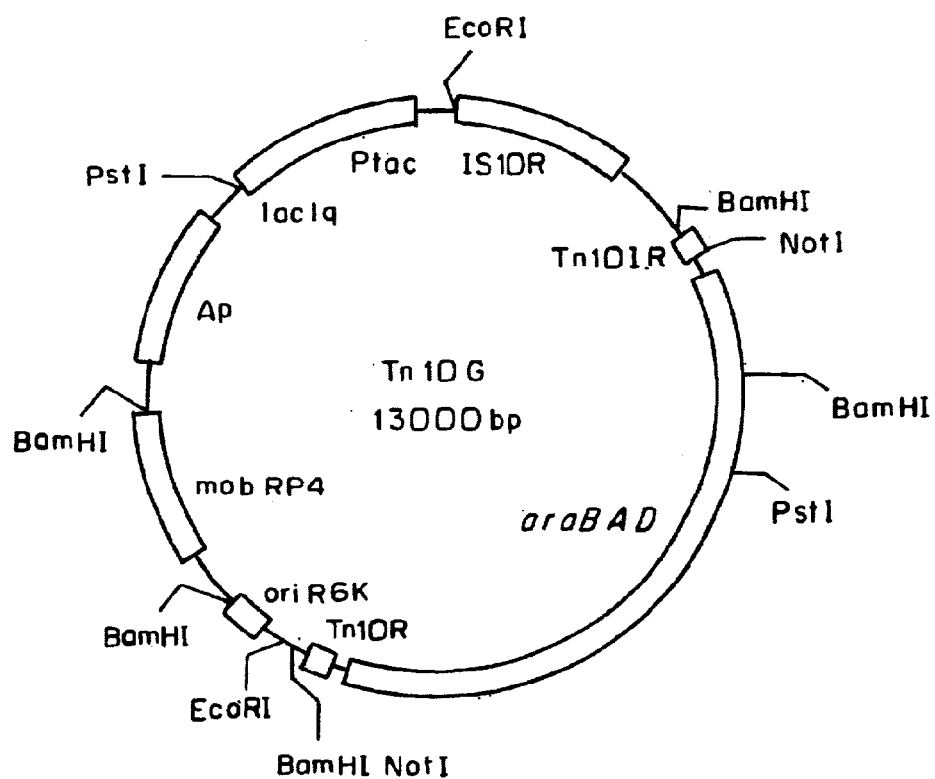
FIG. 11 is the plasmid map of Tn10G. $IS10_R$ is the transposase gene. IR is the inverted repeat sequence of the transposon. AraBAD was inserted between the two inverted repeats at the NotI sites.

Mini-Tn5 was used for constructing C25 with Peno-tal/tkt and Pgap-xylAB operons. Although the transposase gene did not exist in C25, mini Tn10 was used for the subsequent integration of Pgap-araBAD to avoid any possible incompatibility between the same transposons. Plasmid Tn10G (FIG. 11) was constructed based on the Tn10-based delivery plasmid, pLOFKm. The $Km^r$ gene was replaced by a NotI fragment of Pgap-araBAD, isolated from pZB206. Tn10G was constructed and maintained in *E. coli* C118. The plasmid was then transferred into the mating donor, *E. coli* SM10λpir for conjugation with Z. mobilis. Since Tn10G is a suicide plasmid in Z. mobilis, only transconjugates with araBAD integration were able to grow on mating plates, supplemented with arabinose. The *E. coli* SM10λpir donor was inhibited, in the plates, by the presence of nalidixic acid. Transconjugates appeared on mating/ara plates in 7 days. Colonies were replica-picked onto RMA and RMX to confirm their phenotypes. Eighty-six percent of the colonies picked were $Xyl^+Ara^+$. Twenty colonies from the pick-plates were cross-transferred to different plates (from xylose plates to arabinose plates or vice versa). Sixty percent of those colonies remained $Xyl^+Ara^+$. Twenty colonies were analyzed in a preliminary Southern hybridization. Using the tnp probe, about 50% of the strains contained the transposase gene in the genome. Eight integrants were then subjected to detailed analysis by Southern hybridization.

Integration of Pgap-araBAD in ldh of C25 was confirmed by Southern hybridization, for the pZB1862-ldhL-ara integrants DNA using the DIG-labeled ara and ldh probes. See, FIGS. 12(*a*) and (*b*). Digoxygenin (DIG)-labeled ldh, ara, and tnp probes were amplified by PCR using Taq DNA polymerase (Qiagen, Valencia, Calif.). DIG-UTP was purchased from Boehringer Mannheim, Indianapolis, Ind. A tnp probe was used to probe for $IS10_R$, the transposase gene of Tn10. PCR products for ldh, ara, and tnp are 1, 1.4 and 0.8 kb, respectively. The following primer sequences were used:

```
DIG-ldh:                                   (SEQ ID NO:20)
5'-TCGCGGATCCGTCTATGCGCGCGTCGCAATATTCAGTTCC-3'

(SEQ ID NO:21)
5'-TCGCGGATCCGTCGCTTGTCTATTAAACAAGCGCATCCGGC-3'

DIG-ara:                                   (SEQ ID NO:22)
5'-CTAACATGTTGACTCCTTCTCTAGACTTAGCG-3'

(SEQ ID NO:23)
5'-GTTGAAACCGCTGGGCACCACGC-3'

DIG-tnp:                                   (SEQ ID NO:24)
5'-CGCACTACACGGTCGTTCTGTTAC-3'

(SEQ ID NO:25)
5'-GGTTGCAGCCACGAGTAAGTCTTC-3'
```

In the blots, there is only one PstI site on pZB1862-ldhL-ara and it is located in Pgap-araBAD. Therefore, one hybridization band (12.9 kb) from the PstI-digested plasmid was expected, using the ara probe. With Pgap-araBAD integrated in the genome two bands generated by the PstI site in Pgap-araBAD and the adjunct PstI sites on the genome located outside the Pgap-araBAD were expected. The results from FIG. 13(*a*) clearly showed that two bands form the total DNA preparation hybridized with the ara probe and demonstrated integration of Pgap-araBAD. The lack of hybridization bands from plasmid DNA of *Zymomonas* integrants indicated that integration had occurred on the genome, rather than on native plasmids. To shown that the ldh was disrupted by the Pgap-araBAD integration, the same DNA was transferred and hybrizied with the ldh probe. As expected, the hybridization patterns for the integrants were the same on both blots, except for C25, as shown in FIG. 12(b). The total DNA from the host strain, C25, used for Pgap-araBAD integration, which has an intact ldh, showed only one band. The results confirmed that araBAD was I integrated in ldh of C25.

FIGS. 13(a) and (b) show the Southern hybridization results using DIG-labeled Tnp and ara probes, respectively, for the eight Pgap-araBAD transposon integrants generated by Tn10 transposition. DNA was digested with a PstI restriction enzyme. PstI cuts Tn10G into two fragments, which hybridized with an ara probe. According to the blots, only G8, G11, G15 and GH17 were ara-positive and tnp-negative. Different band patterns indicated that Pgap-araBAD was integrated at different loci in the genome. Although the transposase gene was not expected to remain in the genome of the integrants, four strains (G5, G6, G14 and G19), out of the eight, contained the transposase gene. Furthermore, G14, and G19 contained the transposase gene on the plasmid. With an ara probe, two bands from the integrants were expected. However, only single bands were observed. To solve this ambiguity, PCR was conducted, for the integrants, using ara primers and it was confirmed that all eight integrants contained Pgap-araBAD in the genome.

Xylose isomerase (XI), xylulokinase (XK), L-arabinose isomerase (L-AI), L-ribulokinase (L-RK), L-ribulose-5-P-4-epimerase (L-Repi), transketolase (TKT) and transaldolase (TAL) were assayed, using cell-free extracts of the Z. mobilis integrants and control strains, according to Zhang, et al., 1995; and Deanda et al., 1996, with minor modifications. Cell-free extracts were prepared by collecting the cultures at late-log phase (30° C., $OD_{600}$ approximately 1.2), washing once with sonication buffer (10 mM Tris-HCl, pH 7.6. 10 mM $MgCl_2$) and sonicating. The cell debris was removed by centrifugation (14,000 rpm, 45 min 4° C.). In the L-AI assay, the volumes of timed samples were scaled down by half (50 µl), 70% $H_2SO_4$ (1.5 ml) and 0.12% carbazole (50 µl). All of the tubes were maintained in a 25° C. water bath, both before and after the addition of 70% $H_2SO_4$, until reading the absorbency. The samples were taken at 0, 5, 10, and 20 min during the reaction.

Figure 14:
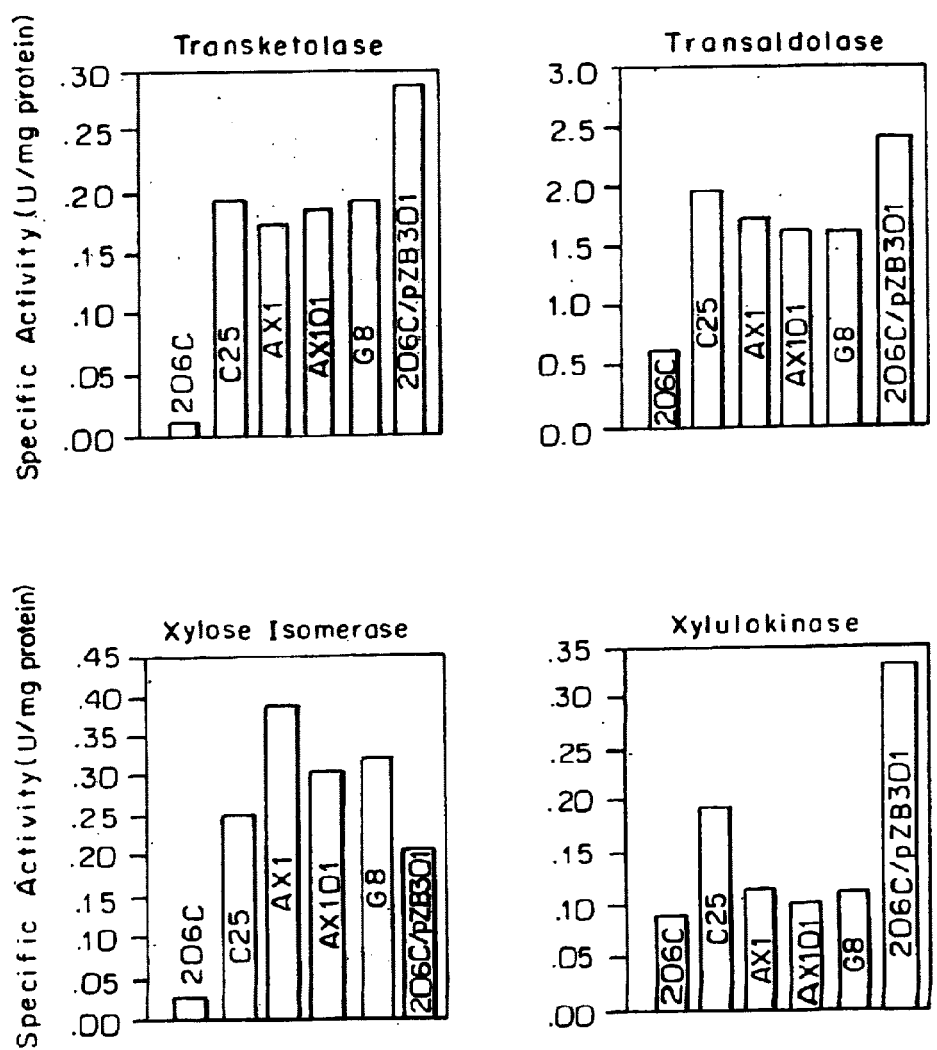
FIG. 14 represents bar graphs of the enzymatic activities of the transketolase, transaldolase, xylose isomerase and xylulokinase of the genomic integrated strains. 206C/pZB301 is a plasmid control. 206C is a host control. C25 is the xylose-fermenting integrant. G8 is the xylose/arabinose fermenting integrant from Tn10 transposition. AX1 and AX101 are the xylose/arabinose-fermenting integrants from homologous recombination.
Figure 15A:
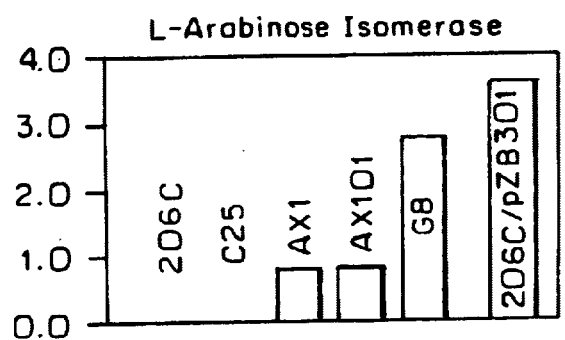
FIG. 15 represents bar graph results of the enzymatic activities of L-arabinose isomerase 15A, L-ribulokinase 15B, and L-ribulose-5 phosphate-4 epimerase 15C, of genomic integrated strains. 206C/pZB301 is a plasmid control. 206C is a host control. C25 is the xylose-fermenting integrant. G8 is the xylose/arabinose-fermenting integrant form Tn10 transposition. AX1 and AX101 are the xylose/arabinose-fermenting integrants from homologous recombination.
Figure 15B:
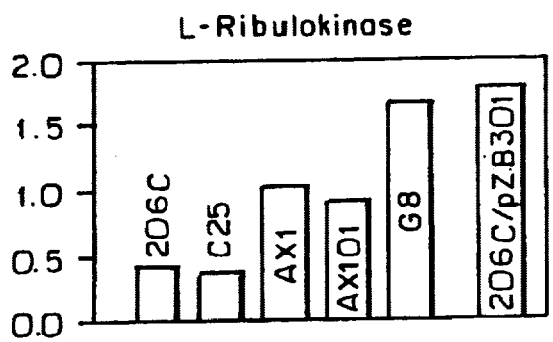
Figure 15C:
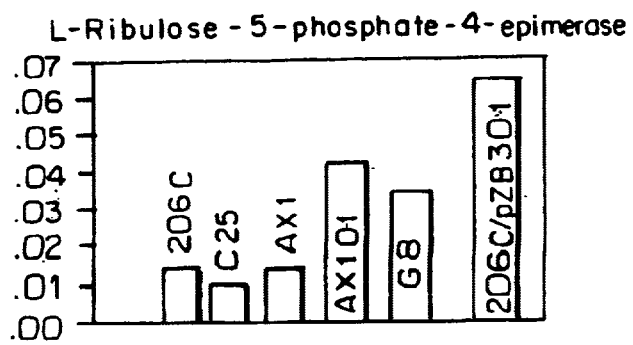

The integrants, from both homologous recombination and transposon integration, were able to grow on D-xylose and L-arabinose. The expression level of the integrated genes was determined by measuring enzymatic activity. Isolates C25/AX1, C25/AX101, and C25/G8 were chosen for the enzymatic assays because they were the most stable integrants, as determined in the stability studies described below. The results of the enzymatic assays are summarized in FIGS. 14 and 15. For all assays (with and exception of xylulokinase), integrants showed positive activities as compared to the controls (C25 and/or 206C). In most assays, (excluding L-ribulokinase and xylose isomerase), the integrants showed lower activities than the plasmid-bearing strain (206C/pZB301). This is presumably related to the copy number of the genes.

For stability studies, the cultures were inoculated into test tubes containing RMG, incubated overnight at 30° C., and transferred daily to RMG tubes. The inoculum was controlled to allow transfer every 10 generations. At every 40 generations, the cells were used to inoculate flasks, containing a mixture of sugars, to test the fermentation capabilities on the sugars without pH control at 30° C. Batch fermentation studies were performed at 30° C. with pH control in Bio-Stat$Q^R$ chemostats, using 500 ml as the working volume. The pH was automatically controlled with 2N KOH. Initial sugar concentration and pH varied between each batch, depending on the culture conditions. All the sugars used were reagent grade. Samples were taken periodically throughout the fermentation, and analyzed for sugars, ethanol and by-products with HPLC, as described previously (Zhang 1995). Optical density, at 600 nm (OD600), was measured in order to monitor cell growth. Ethanol yield was based on the amount of total available sugar.

Figure 17A:
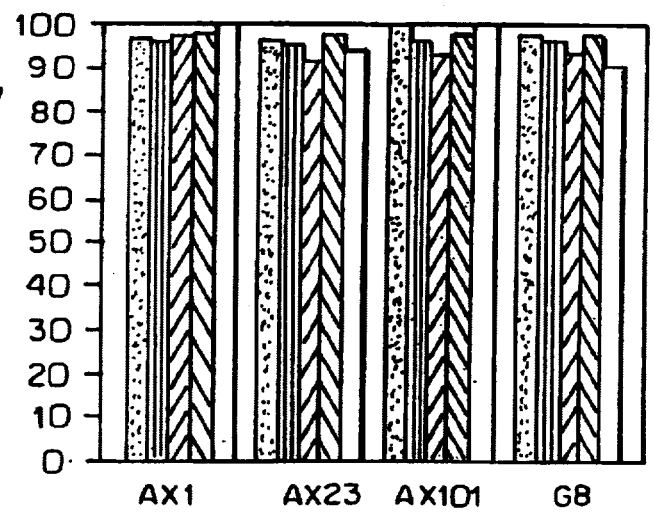
FIG. 17 represents bar graph results of the xylose and arabinose utilization of the genomic integrated xylose and arabinose-fermenting *Zymomonas* strains on RM containing 1% glucose, 2% xylose and 2% arabinose at 30_C with pH control; as shown by FIGS. 17A and 17B.
Figure 17B:
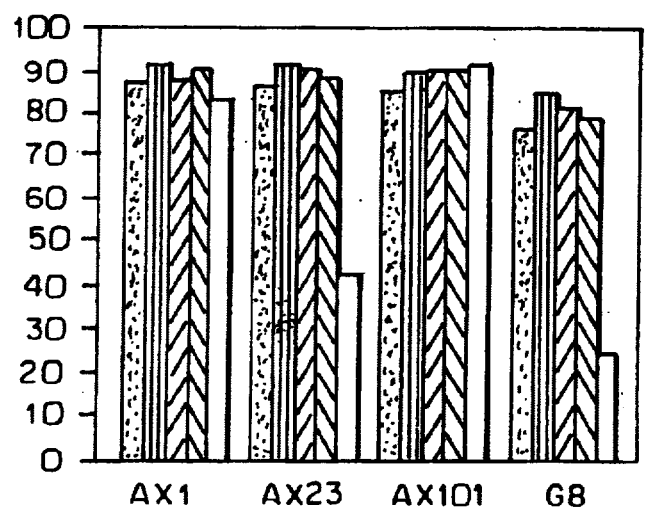
Figure 18A:
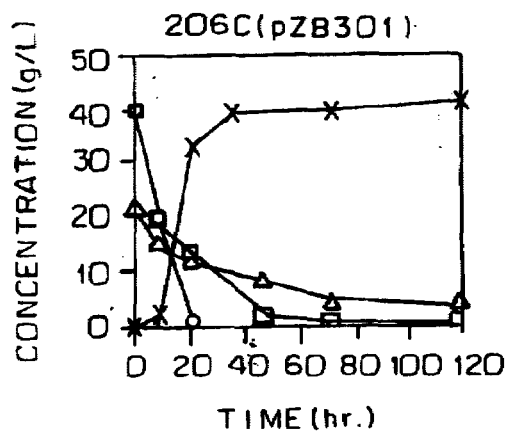
FIG. 18 is a line graphic representation of the fermentation performance of the genomic integrated xylose and arabinose-fermenting *Zymomonas* strains in RM containing 4% glucose, 4% xylose and 2% arabinose at pH5.5 and 30° C.
Figure 18B:
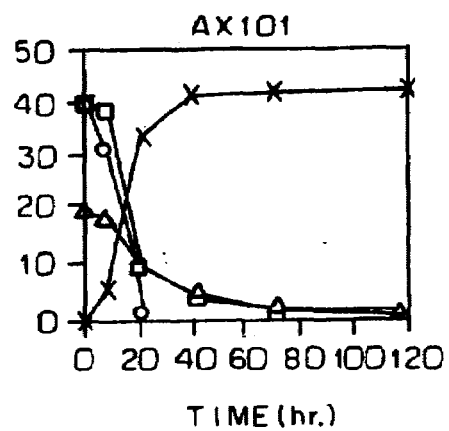
Figure 18C:
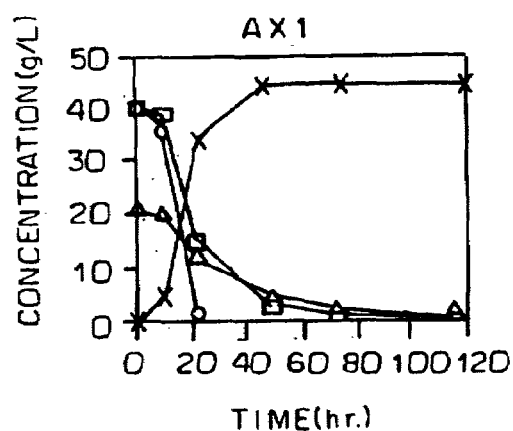
Figure 18D:
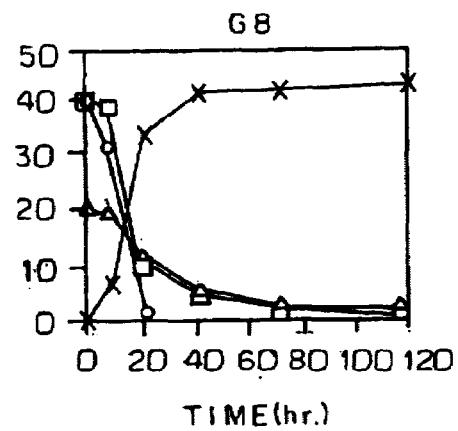

Several genomic integrated xylose and arabinose fermenting Z. mobilis strains developed through both homologous recombination and transposition, were studied for their stability in a non-selective medium (RMG). These strains were cultured in RMG medium and serially transferred, daily, after about 10 generations. After every 40 generations, the cells were used to inoculate a flask containing 1% glucose and 2% xylose and 2% arabinose for examination of their ability to ferment xylose and arabinose to ethanol. Ethanol process yields, and xylose and arabinose utilization rates, were used as the stability trait. Two of the isolates remained stable for 160 generations. See, FIGS. 16 and 17. Three integrated strains and a plasmid-bearing strain were further tested for fermentation performance, in a media containing a mixture of 4% glucose, 4% xylose, and 2% arabinose at pH 5.5 and 30° C. A shown in FIG. 18, all three strains utilized glucose, xylose and arabinose in 72 hours, while the plasmid-bearing strains still had 6 g/L residual arabinose. However, the integrated strains produced more xylitol (4 g/l) than the plasmid bearing strain (1 g/L). The two homologous recombination AX1 and AX101 strains did not produce lactate because the lactate dehydrogenase gene was inactivated through the gene integration. The process yields (about 83% of theoretical) of the integrated strains were very similar to the plasmid bearing strain. Moreover, the integrated strains grew to greater cell densities, which reflects to a lesser metabolic burden associated with having only a singly copy of the seven genes.

Example IV

The following example illustrates the integration of PgapxylAB into ldh of Z. mobilis 31821-5C through homologous recombination. Z. mobilis 31821 has been shown previously to have increased tolerance to high sugar feed streams, high temperatures and acetic acid. As such, Z. mobilis 31821 is an excellent target for integrating the four genes for xylose utilization (tal, tkt, xylA and xylB). However, strain 31821 was found to be very difficult to transform using DNA from a normal E. coli host. It was found that the strain appears to have a unique genetic background which restricts DNA from a methylation host. The existing method using minTn5Tc via transconjugation using E. coli Sm10 (λpir) as donor host did not work in 31821-5C. Different integration techniques were attempted. The mini-Tn5 and mini-Tn10 systems are not applicable due to the lack of a methylation-deficient E. coli donor host which may be needed for conjugation in the 31821 strain for the transposon plasmid. Two trials were made to conjugate a miniTn5 (which contains a $Tc^r$ gene between the insertion sequences) into 31821-5C, and no transconjugates were obtained. Considering a small fragment such as $Tc^r$ (1.5 kb) can not be conjugated and integrated in the genome of 31821-5C by mini-Tn5 transposition, integration of any larger fragment such as PgapxylABTc or PenotaltktCm may not be feasible. A transposition method based on transformation instead of conjugation into the host was developed (using EZ::TN insertion kit see below) and an enlarged homology region for homologous recombination has been developed due to strain 31821's low recombination efficiency.

Several attempts made to integrate all four genes (arranged in two operons—PgapxylAB and Penotaltkt) in the genome of 31821-5C using EZ::TN insertion kit were not successful. This could be due to two potential problems. First, the size of the insert might be too large for integration to occur in the genome. Secondly, the direct selection on xylose medium may not allow the genes to be expressed in time for the integrants to grow. To overcome the potential problems, it was necessary to device a different approach for gene integration in 31821. Instead of the integration of all four genes, two genes (one operon-PgapxylAB or Penotaltkt) would be integrated at one time. Two operons would be integrated sequentially in the same host. Each operon would be connected to an antibiotic marker ($Tc^r$ or $Cm^r$) for the initial selection of integrants. This way, integrants can be selected by antibiotic resistance. Two integration methods were used for xylose utilization genes into 31821-5C (homologous recombination and transposition). A $Tc^r$ gene was integrated in the ldh of 31821-5C using a 2-kb homology region including ldh (namely ldhL). In the two out of several attempts to integrate a PenotaltktTc fragment in 2-kb ldh locus, it took a very long time to obtain the integrants due to the lengthy curing and enrichment process (at least 14 days). However, the integrants were not able to grow on xylose when a plasmid containing PgapxylAB was transformed into the integrants. A PCR fragment using ldh-specific primers and the integrant genomic DNA as template was made and analyzed by DNA sequencing. The result indicated no mutation was introduced in the Penotaltkt operon. Two potential problems were examined. First, the orientation of taltkt genes was opposite to that of a gene, pgm, which is immediately upstream to. ldh in the genome. There are strong promoters in the pgm gene, which might counteract the expression of taltkt. Secondly, the Peno is a relatively weak promoter in *Zymomonas*. Single copy of Penotaltkt in the integrant may not be enough for the gene expression. Integration of Penotaltkt was then attempted by transposition (since ldh site could present a problem of upstream strong promoter) and PgapxylAB by homologous recombination. More importantly, the homology region for integration needed to be expanded beyond the 2-kb ldhL region in order to increase the recombination efficiency. The new homology region was extended and included the flanking regions of ldh (pgm and adhI genes). The total homology size was approximately 4 kb (designated ldhL4).

A strategy was developed for integration of the PgapxylAB operon into the 31821 genome by constructing pZB510XTc and pZB512XTc (see FIGS. 19A and 19B) and two more similar plasmids (pZB511XTc and pZB513XTc) with different organization of the genes in the cassette based on replicative plasmid, pZB1861. The homology fragment ldhL4 was generated by two PCR reactions, resulting in 5'- and 3'-fragments. PCR-generated fragments 5'dhL4 (1.9 kb) and 3'ldhL4 (2.4 kb) were sequentially inserted into BamHI-XbaI site and BamHI site of shuttle vector, pZB1861. NotI and SfiI restriction sites were introduced in between 5'ldhL4 and 3'ldhL4 during PCR. The integrative plasmid pZB510xTc was then constructed by inserting $P_{gap}$xylAB (from pZB4) and $Tc^r$ (PCR product) in NotI and SfiI sites. Plasmid pZB512XTc was constructed in a similar fashion except the orientation of the $P_{gap}$lAB was opposite to that in pZB510XTc.

The plasmids were introduced in strain 31821-5C by electroporation. Plasmids pZB510XTc, pZB512XTc, pZB511XTc and pZB513XTc were used to transform 31821-5C. After several attempts, transformants with pZB510XTc and pZB512XTc were obtained. No transformants with pZB511XTc and pZB513XTc were obtained.

$Tc^r$ marker was included in the integration cassette and used for the selection of integrants. $Cm^r$ marker however was located outside the cassette on the vector background. $Tc^rCm^r$ transformants were selected and cultured in the presence of Tc for 2 to 4 daily transfers. During propagation of the transformants, PgapxylABTc was integrated in the ldh of the host through homologous recombination. To enrich and isolate the integrants, plasmid curing was conducted. Curing of plasmids can be achieved by sub-culturing the transformants at 37° C. in the absence of antibiotics for several daily transfers for about 7 to 14 days. Constant monitoring of the loss of plasmids was performed for the cultures from each transfer. By the third transfer, >99% of the cells became $Cm^s$ indicating the loss of plasmids. Cultures from the $3^{rd}$, $4^{th}$, $5^{th}$ and $6^{th}$ transfers were inoculated in RMGTc at 30° C. to enrich the growth of potential PgapxylAB integrants. Enriched cultures were plated on RMGTc plates and replica-picked onto RMGCm and RMGTc plates. The integrants ($Tc^rCm^s$) were distinguished from the wild type ($Tc^sCm^s$) and plasmid-bearing ($Tc^rCm^r$) cells by the antibiotic resistance phenotypes. Several potential PgapxylAB integrants were isolated and subjected to further analysis. Back transformation in *E. coli* DH5a with the plasmid DNA extracted from the integrants was conducted to exclude the plasmid-bearing strains. PCR analysis for the colonies was performed to examine the genotype of the integrants using Tc, xylAB and $Cm^r$ primer pairs individually. Four isolates, x4i, x6i, x9i and x10i were indicated to be integrants because no transformants were obtained in back transformation, and PCR results showed xylAB and $Tc^r$ bands but not a $Cm^r$ band.

The PgapxylAB integrants (x4i, x6i, x91 and x10i) were transformed with a *Zymomonas* replicative plasmid pZB192, which carries Penotaltkt, but not PgapxylAB. The transformants were able to grow in RMX, indicating single copy of integrated PgapxylAB provided sufficient xylose isomerase and xylulokinase activities for xylose utilization when tal and tkt genes were supplied on a plasmid (multiple copies). The results also ensured that we could further integrate Penotaltkt in the PgapxylAB integrants to construct a fully integrated xylose-fermenting 31821 strain (see Example VI).

Example V

The following example illustrates the integration of Penotaltkt into the genome of *Z. mobilis* 31821-5C through transposition. Mini-Tn5 or mini-Tn10 transposition was not applicable for 31821 because of the lack of a methylation-deficient donor host for conjugation. A new transposition method (EZ::TN insertion kit) was adopted. The nature of the method requires the transposases to bind to the Mosaic ends flanking PenotaltktCm and cleave the fragment out while remaining bound to the ends when electroporated into the cells. Inside the cells, the transposases trigger the transposition of the DNA fragment into the genome of the host. Integrative plasmid pMODPenotaltktCm (see FIG. 20) is a non-replicative plasmid in *Zymomonas* prepared from a methylation—deficient *E. coli* host. Electroporated cells were plated on MMGCm plates. The $Cm^r$ transformants should be integrants. Three $Cm^r$ integrants resulted using this transposition method, referred to herein as int1, int2 and int3. Integrants were confirmed by PCR screening using primers for tal or Cm. Also, confirmation was acquired by back-transformation of plasmid from integrants into *E. coli* to make sure the PenotaltktCm$^r$ was not carried on the pMOD plasmid.

The integrants were transformed with a plasmid pZB188-xyl, which carries PgapxylAB (but not Penotaltkt). Electroporated cells were plated directly on MMX plates. No transformants were obtained in this complementation experiment. A single copy of Penotaltkt may not provide enough transaldolase and transketolase activity for initial growth on xylose plates. A stronger *Zymomonas* promoter, such as Ppdc (of pyruvate decarboxylase gene) and Pgap (of glyceraldehydes phosphate dehydrogenase gene) may be able to compensate the low-copy-number effect to the taltkt expression.

Example VI

The following example illustrates the construction of Penotaltkt/PgapxylAB integrants. Attempts to integrate the four xylose utilization genes was not successful using either transposition or homologous recombination. Since single copy of Penotaltkt into the 31821-5C genome did not support strain growth on xylose when providing xylose assimilation genes on a plasmid. The applicants tried to increase the copy number of integrated Penotaltkt by in vitro transposition of pMODPenotaltktCm into strain 31821 native plasmids. The transposed native plasmids were then electroporated into a PgapxylAB integrant, x9i. The final integrants selected by Tc$^r$Cm$^r$ were designated x9t(enott)Pi. Plasmids isolated from integrants were used to back transform *Z. mobilis* 31821-5C and *E. coli* DH5a. Back transformants were obtained for *Z. mobilis*, but not for *E. coli*, indicating the genes were integrated in the native plasmids of x9i. In another approach, integrative plasmids, pZB510XTc and pZB512XTc containing PgapxylABTc$^r$ were prepared from *E. coli* DM1 and transformed to int2. Tc$^r$Cm$^r$ transformants were obtained after many attempts of electroporation. The transformants were then used to go through a prolonged curing and enrichment process as described above. Integrants obtained by both approaches were tested in growth in medium containing xylose (RMX). Growth on the RMX of some of the integrants was observed, but was very minimal. After a serial of adaptation in RMX (see examples below) two integrants from each integration (x9t(enott)Pi #4 and #8; int2/321 and int2/1821) performed relatively better in RMX and were further analyzed. The resultant potential Penotaltkt/PgapxylAB integrants were subjected to Southern hybridiztion analysis to confirm the presence of the target DNA. Hybridization was performed using a xylB probe digested with SphI (FIG. 21A) using total DNA and plasmid DNA prepared from these integrants. Plasmid pZB512XTc (as a control) was expected to have two bands, 5.4 and 2.5 kb, of which the 2.5 kb band is common to total DNA of integrants x9t(enott)Pi#4, #8 and int2/321. Plasmid pZB510XTc, however, was expected to have two bands, 4.2 and 3.7 kb, of which the 3.7 kb is common to total DNA of integrant int2/1821. All the integrants were based on x9i, in which PgapxylAB was integrated in the LDH locus in the genome.

Figure 21:
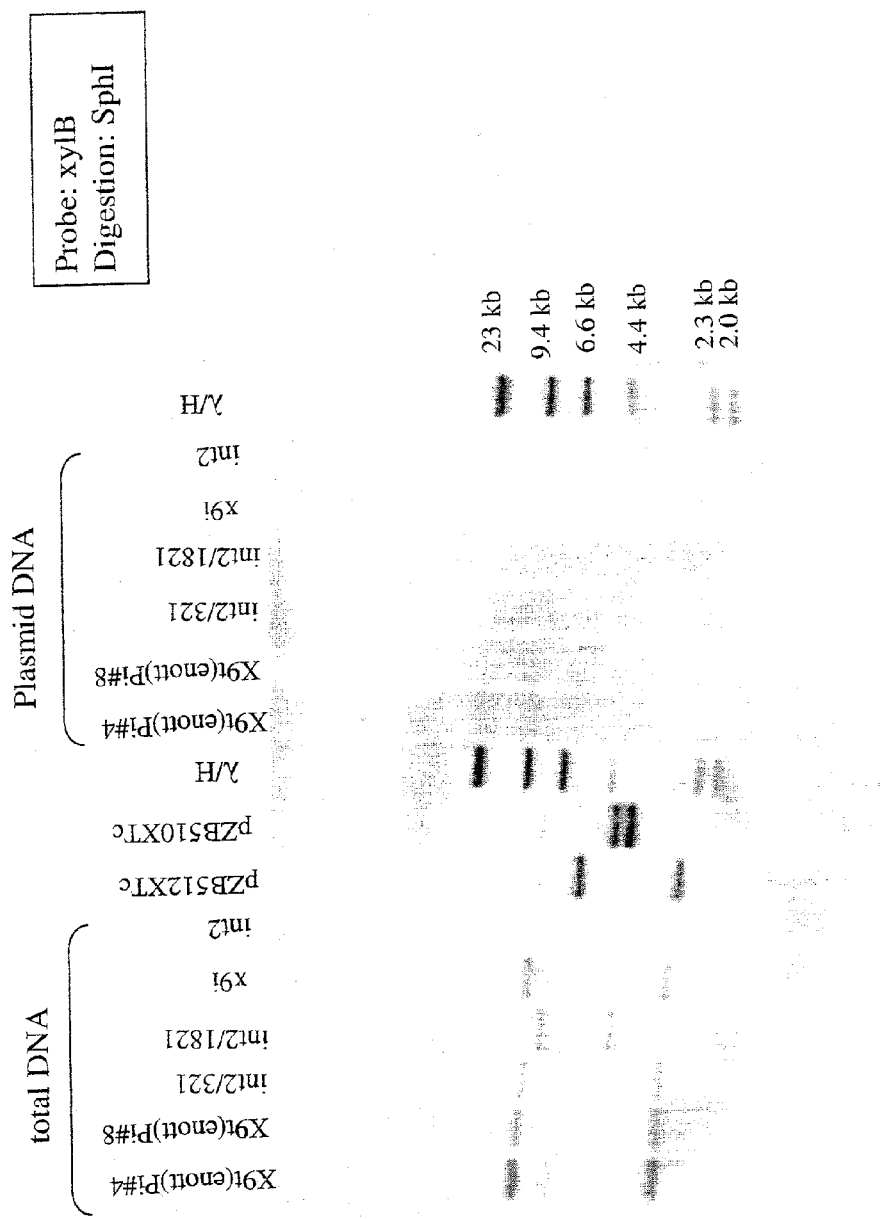
FIGS. 21 A and B represent Southern hybridization blots for integrants of *Z. mobilis* 31821. Probes xylB (21A) and tkt (21B) were used in the experiment. Plasmid controls included $pMODP_{eno}taltktCmPZB510XTc$ and pZB512XTc, and note that $P_{gap}xylAB$ in int 2/321 was from pZB512XTc. $P_{gap}xylAB$ in int2/1821 was from pZB510XTc. λ/H was used as a molecular weight marker.
Figure 21:
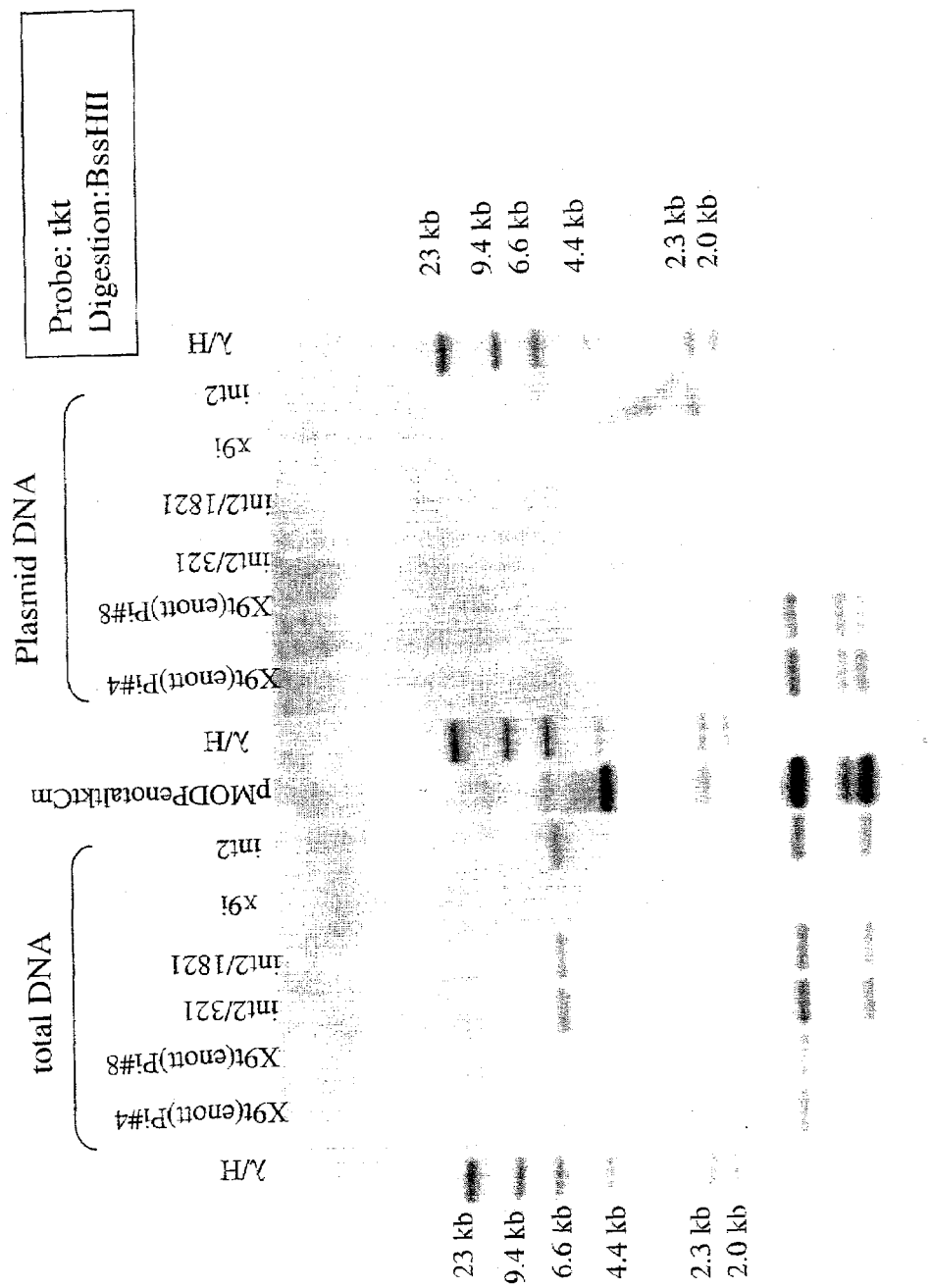

All of the integrants have one band common to their respective integrative plasmids as well as a second band, which is different from the bands generated from the plasmids as expected. All the integrants contained bands in the total DNA preps but not in the plasmid DNA preps, indicating the PgapxylAB was integrated in the chromosome instead of in the native plasmids of ATCC31821. In hybridization with tkt probe, total DNA and plasmid DNA prepared from these integrants were digested with BssHII (FIG. 21B). Plasmid pMODP$_{eno}$taltktCm (as a control) was expected to have 4 bands including 4.2, 1.5, 0.9 and 0.1 k, of which 1.5 and 0.9 kb bands are common to the total DNA of all the integrants. The 0.1 kb band was too small to be retained on the gel. As shown in FIG. 21B, x9t(enott)Pi#4, #8 contained the 1.5 and 0.9 kb bands in both the total and plasmid DNA preps, confirming that the P$_{eno}$taltkt was integrated in the native plasmid. The third band, which is missing from the #4 and #8 on the blot might be to small to be on the gel. According to the map (see FIG. 20), this band could be as small as 0.4 kb. In addition to two common bands, int2/321 and int2/1821 possessed a 6.4 kb band, which is different from that of the plasmid, indicating that P$_{eno}$taltkt was integrated in the chromosome of these two integrants.

Example VII

Figure 22:
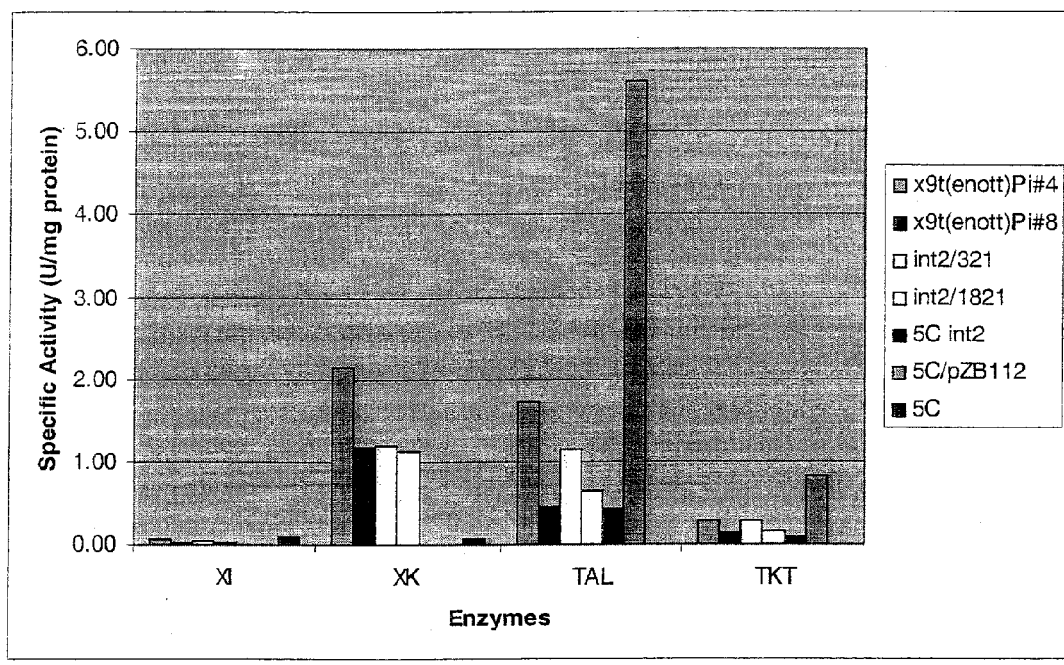
FIG. 22 represents a bar graph showing the enzymatic activities of x9t(enott)Pi#4, x9t(enott)Pi#8, int2/321 and int2/1821 and control strains.
Figure 23A:
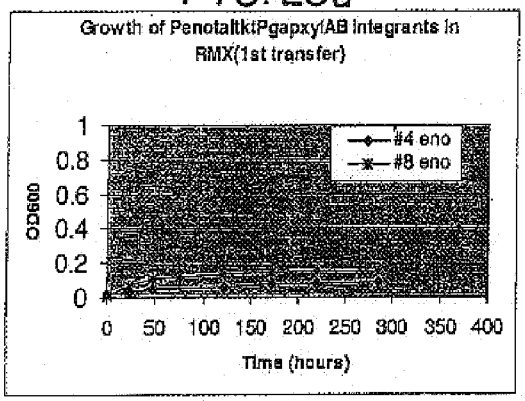
FIG. 23 is a graphical representation of the growth adaptation of x9t(enott)Pi#4, x9t(enott)Pi#8, int2/321 and int2/1821 in RMX media.
Figure 23B:
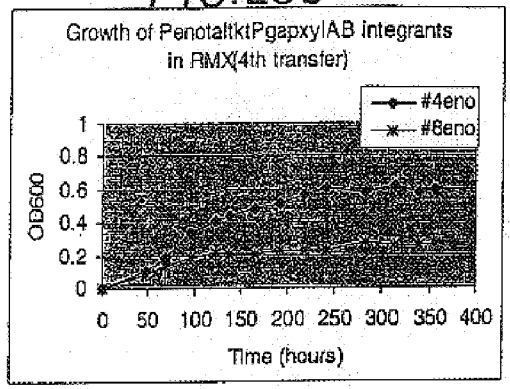
Figure 23C:
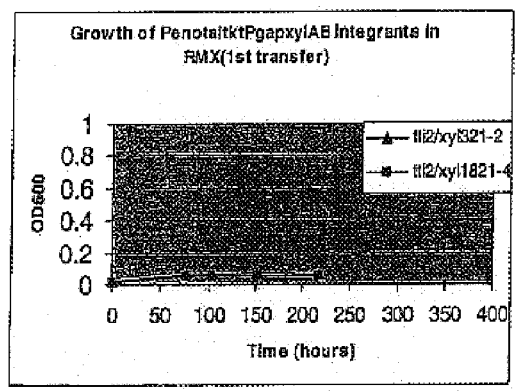
Figure 23D:
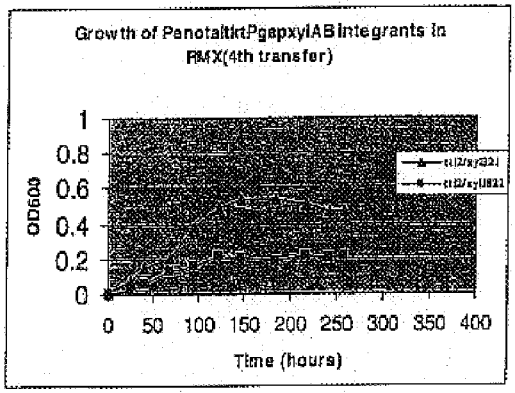

The following example illustrates the enzymatic activity of the integrant *Zymomonas*. Cultures were inoculated from the 5th (for x9(enott)Pi#4 and #8) and 4th (for int2/321 and int2/1821) transfers of RMX into RMG and grown for 16 hours before inoculation into fresh RMG. Cells were harvested at OD600=1.0 grown on RMG for assays. The results are shown in FIG. 22.

Strain int2 based on 31821-5C, a chromosomally integrated P$_{eno}$taltkt strain, and 31821-5C/pZB112, a plasmid-bearing strain containing P$_{eno}$taltkt on a shuttle plasmid (pZB1861-derivative) as well as the host strain 31821-5C, were included in TAL and TKT assays as controls. Enzymatic assays on xylose isomerase, xylulokinase, transaldolase and transketolase were performed on all the integrants and control strains. Strain 31821-5C/pZB112 showed high activities for transaldolase and transketolase as expected. Different enzymatic levels were observed from the integrants. Furthermore, different enzymatic levels were observed even among the integrants obtained using a similar integration method. Strains x9t(enott)Pi#4 generated the highest and int2/321 the second highest activities in all assays. These strains also grew better in RMX (see FIG. 23). It should be noted that the native plasmid-integrated strains (x9t(enott)Pi#4 and #8) did not necessarily have a higher TAL, TKT activities.

Example VIII

The following example illustrates that the *Z. mobilis* 38121-5C P$_{eno}$taltkt/P$_{gap}$lAB integrants are able to ferment D-xylose to ethanol after a series of adaptation on RMX. Integrants were inoculated in RMX (containing 2% of xylose) tubes sealed with parafilm to prevent evaporation. The growth was monitored routinely by OD600 measurements. Cultures from exponential stage were transferred to fresh RMX. As shown in FIG. 23, a comparison was made of growth curves between the 1st and 4th transfers.

The growth rate and final OD600 reading were improved over the period of adaptation. The final OD was increased from 0.08 (first transfer) to 0.6 (fourth transfer). The growth rates and maximal OD600 readings were stabilized after the fifth transfer. It is believed that mutation of the cultures occurred during the process of adaptation. RMX provided the natural selection of mutants with more effective utilization. Among the four integrants analyzed, two showed the highest rates of growth and ODs, the x9t(enott)Pi#4 and int2/321. Samples from the cultures of the fourth/third transfers were taken at 140-hour time point for HPLC analysis. As shown in Table 1, xylose was consumed from 20 g/L from the initial concentration to 4–14 g/L and significant levels of ethanol formed, indicating that the Z. mobilis 31821-5C $P_{eno}$taltkt/$P_{gap}$xylAB integrants were able to ferment D-xylose to ethanol.

1) The accession number for the Z. mobilis 31821 $P_{eno}$taltkt/$P_{gap}$xylAB is: ATCC 31821-5C $P_{eno}$taltkt/$P_{gap}$xylAB (8b)
2) The date of deposit is Sep. 15, 2005;
3) The description of the deposit is: Integrant of the Zymomonas mobilis strain 31821-5C $P_{eno}$taltkt/$P_{gap}$xylAB; and
4) The depository is the American Type Culture Collection at 10801 University Boulevard, Manassas, Va. 20110-2209 USA.

TABLE 1

HPLC analysis for Z. mobilis 31821 $P_{eno}$taltkt/$P_{gap}$xylAB integrants in RMX at 140 hours

| STRAINS | OD 600 nm | Xylose g/L | Ethanol g/L | Consume Sugar Yield % |
|---|---|---|---|---|
| x9t(enott)Pi#4- 4th transfer | 0.441 | 4.24 | 7.70 | 86.08 |
| x9t(enott)Pi#8- 4th transfer | 0.206 | 12.46 | 3.53 | 74.27 |
| int2/xyl321- 3rd transfer | 0.506 | 4.90 | 7.42 | 86.19 |
| int2/xyl1821- 3rd transfer | 0.208 | 14.76 | 2.59 | 72.34 |
| RMX alone (control with no strain) | 0.000 | 21.78 | 0.00 | |

Example IX

Figure 24:
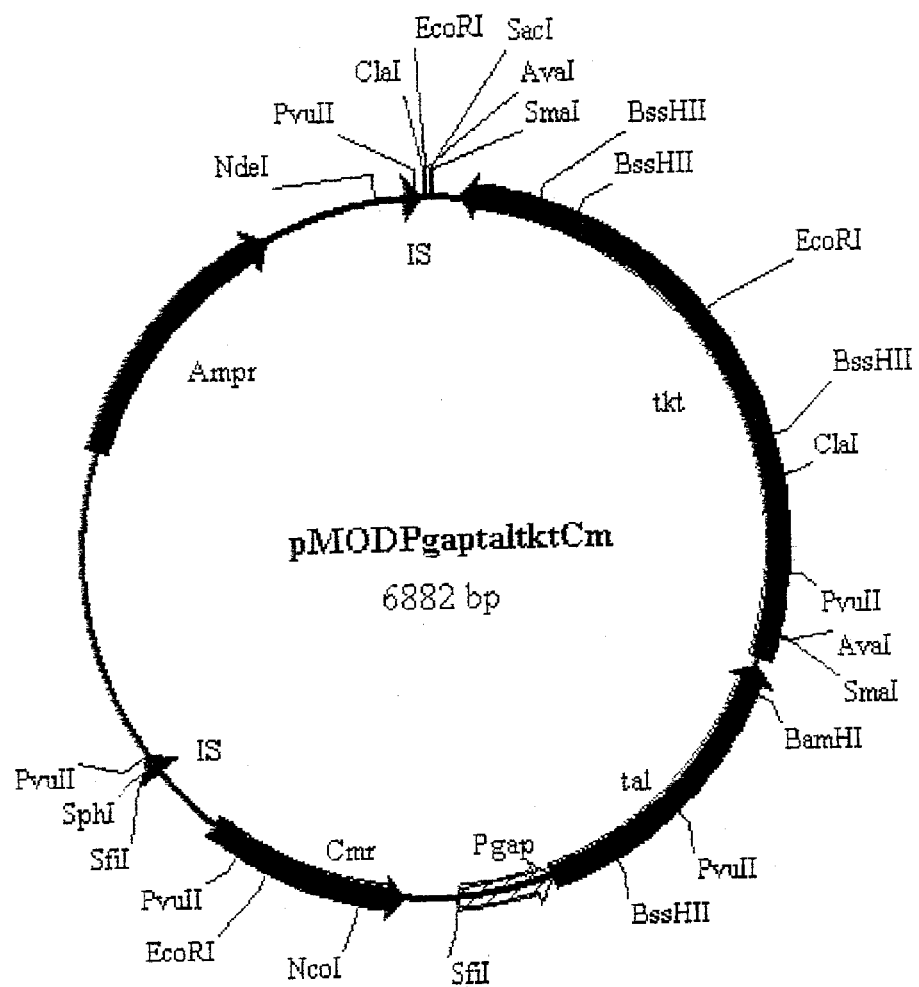
FIGS. 24 the plasmid map for $pMODP_{gap}taltktCm$ for integrative transposition into *Z. mobilis* 31821.

The present example illustrates the construction of pMODPgaptaltktCm for transposition in Z. mobilis. A similar approach to construct pMODPenotaltktCm was used except two loxP sites was introduced. A 2.2-kb tkt fragment was isolated from pUCtaltkt by BglII/XbaI digestion and cloned in pMOD vector digested with BamHI/XbaI, resulting pMODtkt. A PCR fragment Pgaptal was generated by fusing a Zymomonas promoter region of GAP (glyceraldehydes-3-phosphate dehydrogenase gene) to the structural gene of tal. This fragment was digested with XbaI and cloned in the plasmid pMODtkt. Finally, the PCR fragment containing two loxP sequences (Palmeros et al., 2000, Gene 247:255–264) flanking the Cm$^r$ (CmloxP) was inserted in the SfiI site of the plasmid to form the integrative plasmid pMODPgaptaltktCm (FIG. 24). The loxP sequences flanking the Cm$^r$ can be used as the binding target for a phage Cre recombinase, which then will remove the Cm$^r$ from the integrant genome if needed. Similarly, this approach can also be used to loop out the Tc resistance gene. It is advantageous to have the ability to remove the antibiotic resistance genes. The applicants introduced a loxP/cre system for this purpose. The oligo sequences for the PCR for the above construction are as follow:

```
1. Pgap (0.3 kb)
Template: pZB4
Primers:
PgapXbSfi(F)                                    (SEQ ID NO:26)
5'CAGTCTAGAGGCCGCCTAGGCCGTTCGATCAACAACCCGAATCC3'

3'Pgap5'tal(R)                                  (SEQ ID NO:27)
5'CAATTTGTCCGTCATGTTTATTCTCCTAAC3'

2. tal (1 kb)
Template: pZB4
Primers:
3'Pgap5'tal(F)                                  (SEQ ID NO:28)
5'GTTAGGAGAATAAACATGACGGACAAATTG3' talXb(R)                                        (SEQ ID NO:29)
5'CCAGATCGTCTAGATTACAGCAGATCGCC3'

3. Pgaptal (1.3 kb)
Template: Pgap and tal
Primers:
PgapXbSfi(F)                                    (SEQ ID NO:30)
5'CAGTCTAGAGGCCGCCTAGGCCGTTCGATCAACAACCCGAATCC3' talXb(R)                                        (SEQ ID NO:31)
5'CCAGATCGTCTAGATTACAGCAGATCGCC3'

4. CmloxP (1.1 kb)
Template: pZB186
Cmlox(F,sfi)                                    (SEQ ID NO:32)
5'CAGGGCCGCCTAGGCCATAACTTCGTATAGCATACATTATACGAAGTT
ATCCTGTGACGGAAGATCACTTCGC3'

Cmlox(R,sfi)                                    (SEQ ID NO:33)
5'CAGGGCCTAGGCGGCCATAACTTCGTATAATGTATGCTATACGAAGTT
ATCCTGAACCGACGACCGGGTCG3'
```

Example X

Figure 25A:
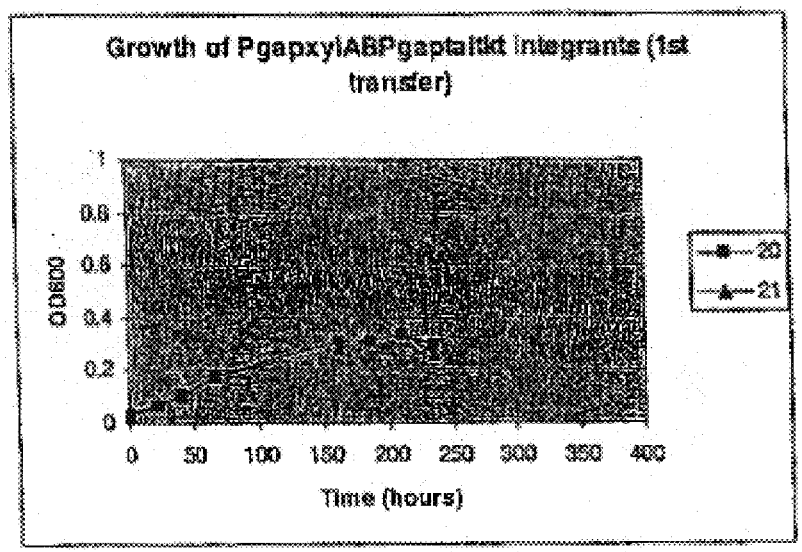
FIG. 25 is a graphical representation of the growth adaptation of #20 and #21, in RMX media.
Figure 25B:
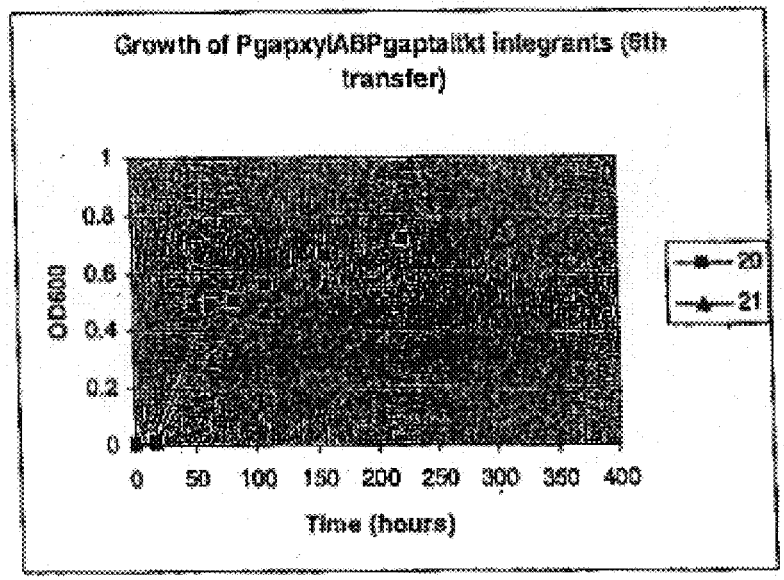

The following example illustrates the construction of Pgaptaltkt/PgapxylAB integrants based on Z. mobilis 31821-5C. Plasmid pMODPgaptaltktCm prepared from E. coli DM1 or JM110 was treated with the EZ::TN transposase to make transposome. The transposome mixture was electroporated into a PgapxylAB integrant, x9i. The Pgaptaltkt/PgapxylAB integrants were obtained by selection on RMGTcCm (the Tc resistance gene was already integrated in the x9i genome). Initial analysis such as back transformation in E. coli, using the plasmid DNA from the integrants was carried out to identify the true integrants vs. plasmid-bearing strains. Several integrants plasmid DNA gave E. coli back transformants and these false integrants were eliminated. Potential Tc$^r$Cm$^r$ integrants were inoculated in RM containing xylose as the sole carbon source and incubated at 30° C. Growth was monitored by measurement at OD600. All strains were able to grow in RMX initially to OD of 0.3 at slow rates. However, the growth rates and final ODs improved after the 6th transfer in RMX. Growth curves for the two better growers (#20, #21) are shown in FIG. 25.

1) The accession number for Zymomonas mobilis 31821-5C $P_{gap}$taltkt/$P_{gap}$xylAB is ATCC 31821-5C $P_{gap}$taltkt/$P_{gap}$xylAB (2032).
2) The date of deposit is Sep. 15, 2005;
3) The description of the integrant of Zymomonas mobilis strain deposit material is: 31821-5C $P_{gap}$taltkt/$P_{gap}$xylAB
4) The depository is the American Type Culture Collection at 10801 University Boulevard, Manassas, Va. 20110-2209 USA.

Example XI

Figure 26A:
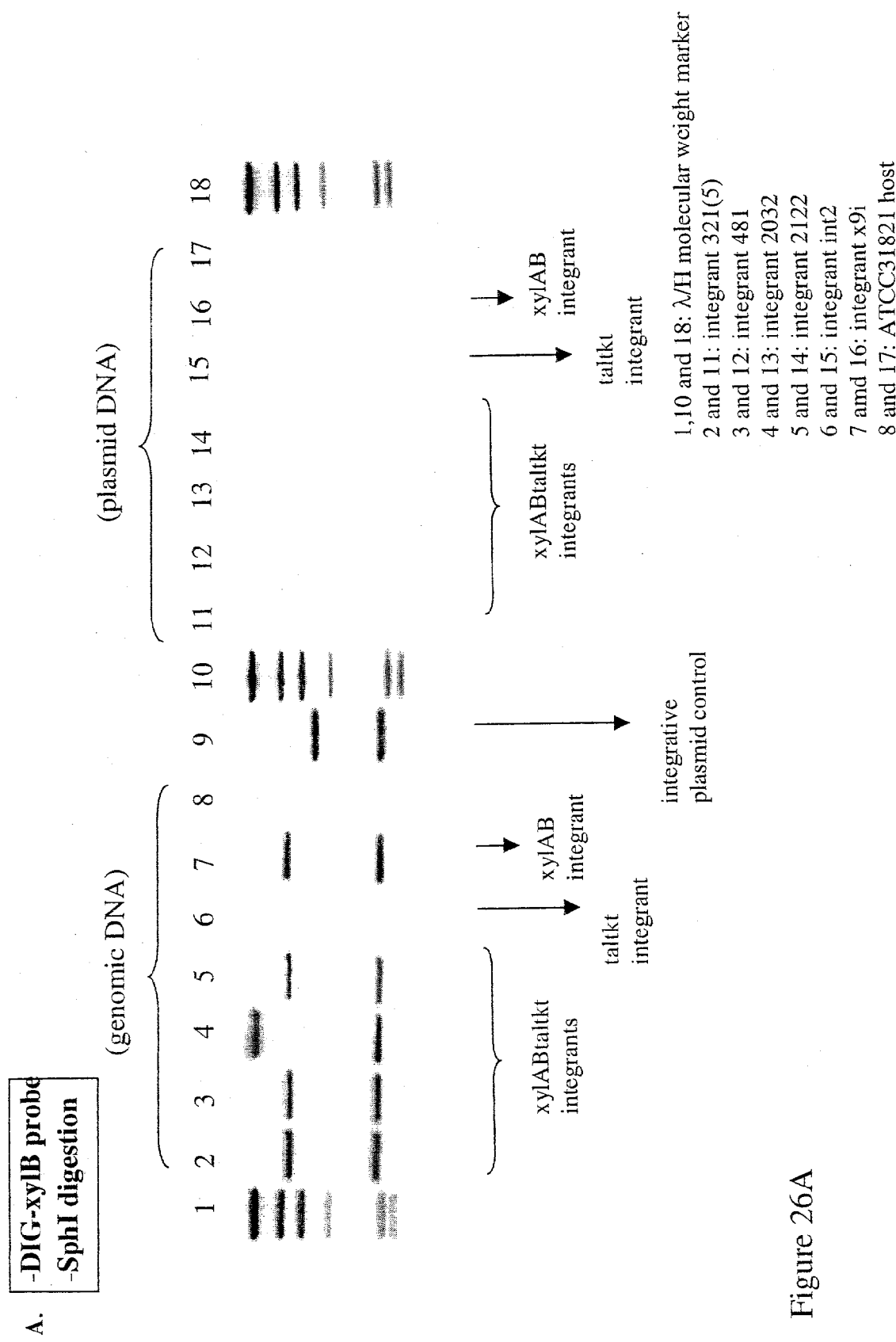
FIGS. 26 A and B represent Southern hybridization blots for integrants of *Z. mobilis* 31821. Probes xylB (26A) and tkt (26B) were used in the experiment. Plasmid controls included $pMODP_{eno}taltktCm$, $pMODP_{gap}taltktCm$ and pZB512XTc, and note that $P_{gap}xylAB$ in 321(5) was from pZB512XTc. λ/H was used as a molecular weight marker.
Figure 26B:
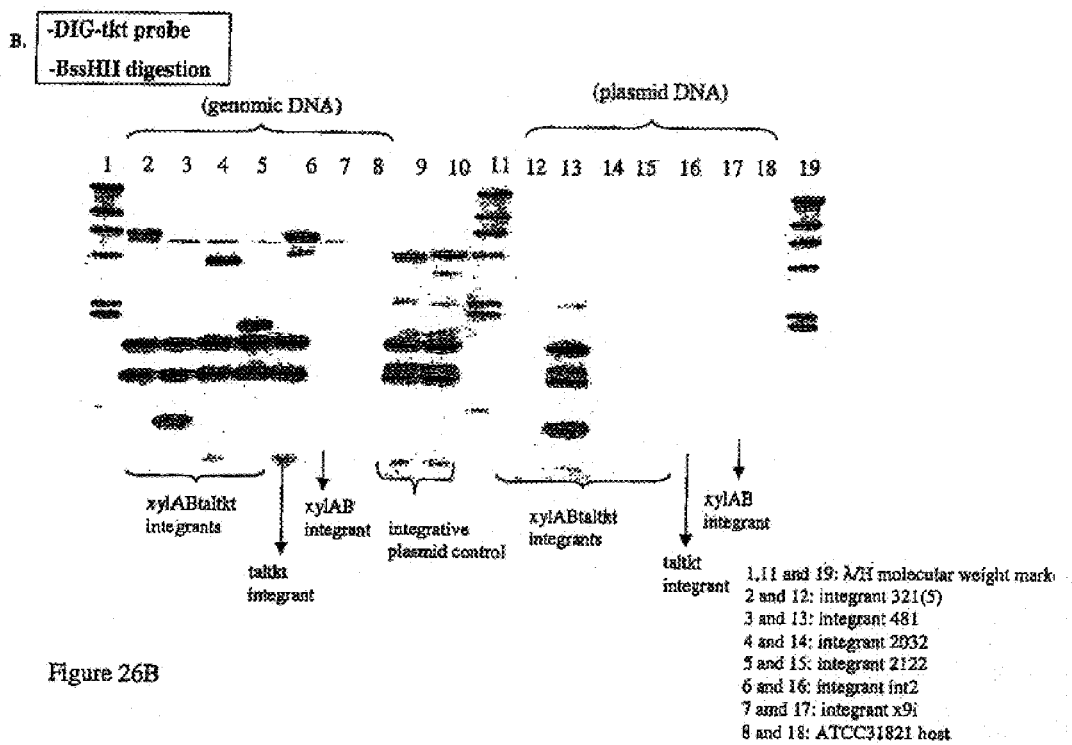

The following example illustrates the process of isolating the Penotaltkt/PgapxylAB and Pgaptaltkt/PgapxylAB Zymomonas integrants. To isolate the better growers in the mixed population, the cells were streaked out on RMX plates. Strains x9t(enott)Pi#4 and x9t(enott)Pi#8 were streaked out after the 4th transfer, int2/xyl321 and int2/xyl1821 were streaked out after the 3rd transfer, and #20 and #21 were streaked out after the 6th transfer. This round of isolation was called 1st isolation. Different sizes of colonies were observed on RMX plates. The large colonies were picked and further streaked out on RMX plates (2nd isolation). Several distinctively large colonies were picked and inoculated in RMX liquid medium for growth analysis. Four strains, which showed promising growth in RMX, were chosen for further analyses including Southern hybridization, fermentation and enzymatic assays. The four strains are designated 321(5) (derived from int2/xyl321), 481 (derived from x9tPenott)Pi#4), 2032 (derived from #20) and 2122 (derived from #21). Southern hybridization was performed using the same method discussed in Example VI. As shown in FIGS. 26A (using xylB as probe) and 26B (using tkt as probe), integration was confirmed by the absence of hybridization bands in the plasmid preps, except for strain 481 (derived from x9t(enott)Pi#4) in FIG. 26B, which was knowingly constructed by integration of Penotaltkt in the native plasmid of Z. mobilis 31821. The difference in the band pattern between 481 and control pMODPenotaltktCm indicated that bands were not of the integrative plasmid. Instead, they were from integration of the PentaltktCm in the native plasmid. In FIG. 26A, an expected common band of 2.5 kb was observed in pZB512xTc and all four integrants. The second band, however, was different between pZB512xTc and integrants, indicating the integration of xylAB in the chromosome (supposedly ldh gene). The higher molecular weight band in 2032 was possibly due to a spontaneous change in the SphI site in genome where it is close to the ldhL4 region. In FIG. 26B, common bands of 1.5, 0.9 and 0.1 kb were expected between pMODPenotaltktCm or pMODPgaptaltkt and all integrants. The different band confirmed the integration of PenotaltktCm or PgaptaltktCm in the genome of 31821-5C.

Figure 27A:
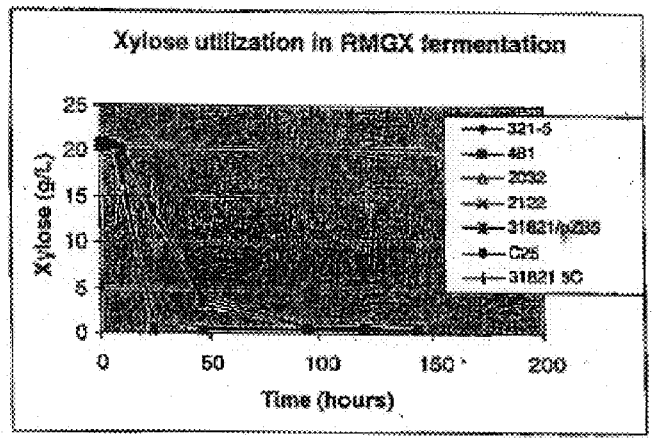
FIGS. 27 A through C are demonstration of xylose (27A) and glucose (27B) utilization and ethanol production (27C) in RMGX for *Zymomonas* integrants.
Figure 27B:
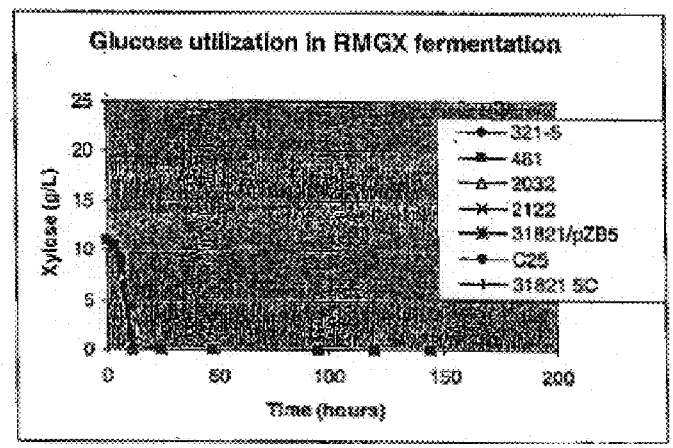
Figure 27C:
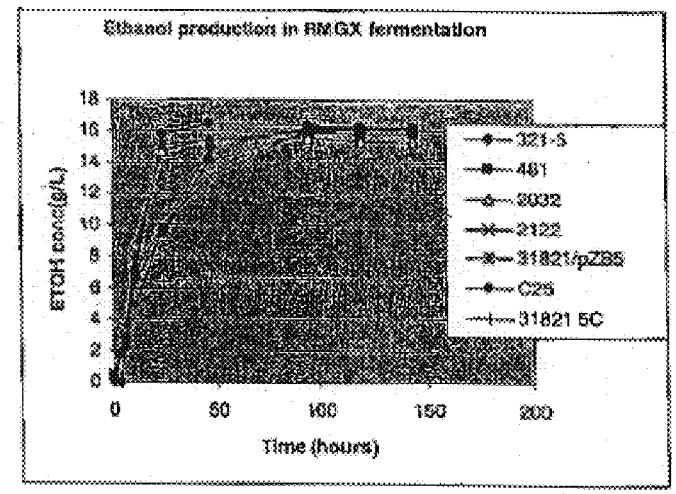
Figure 28A:
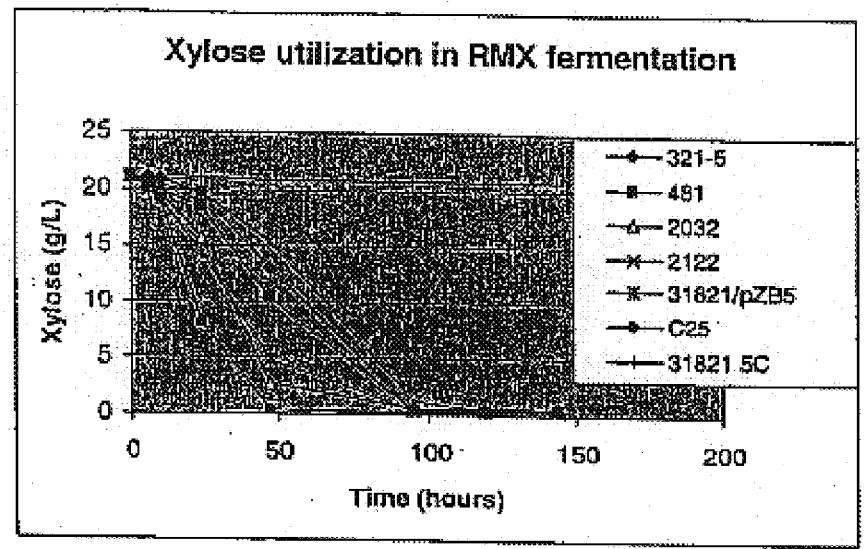
FIGS. 28 A and B are demonstration of xylose (28A) utilization and ethanol production (28B) in RMX for *Zymomonas* integrants.
Figure 28B:
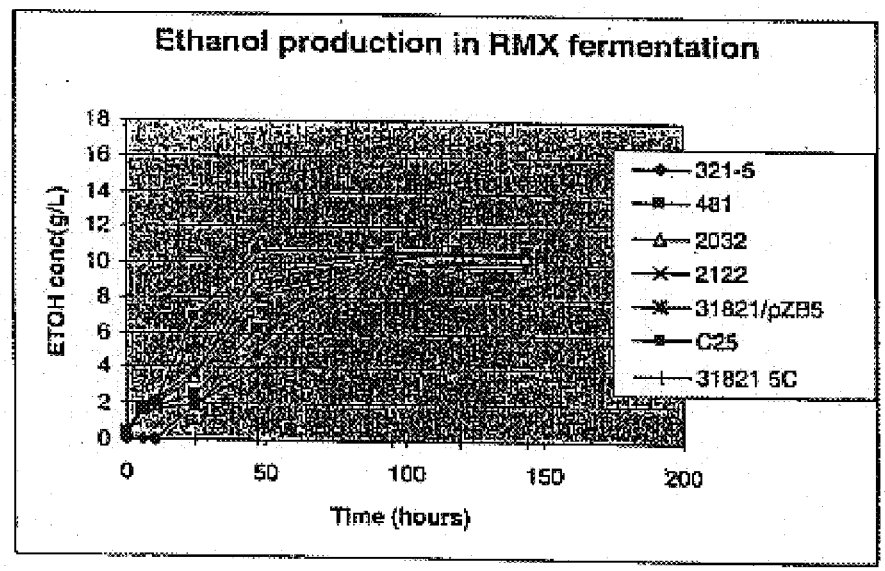

Preliminary fermentation was performed for the four integrants, 321(5), 481, 2032 and 2122 as well as the control strains, 31821/pZB5 (plasmid-bearing strain), C25 (39676-based xylose-fermenting integrant) and 31821-5C (host). The fermentation condition was: 80-ml RMX (2% xylose) or RMGX (1% glucose and 2% xylose) in bottles, no pH control, 30° C. static. Fermentation was monitored by the HPLC analysis of the supernatants of the fermentation broths. All integrants were able to grow in RMGX and ferment both xylose and glucose to ethanol at maximal yields (FIGS. 27A, B and C). All integrants were able to grow in RMX and ferment xylose to ethanol at maximal yields (FIGS. 28A and B). The ethanol production profile is similar between the integrants and the plasmid-bearing control strain (31821/pZB5) and C25 integrant (39676 based xylose integrant) in both media (FIGS. 27C and 28B). As expected, the host strain only fermented glucose to ethanol (FIG. 27B) in RMGX medium.

Enzymatic assays were also performed for the four integrants and the control strains, 31821/pZB5 (plasmid-bearing strain), C25 (39676-based xylose-fermenting integrant) and 31821-5C (host). The data is shown in Table 2 below. All integrants showed lower activities than 31821/pZB5 and C25.

TABLE 2

Enzymatic activities of integrants.

| | Specific Activity (μmol/min-mg protein) | | | |
|---|---|---|---|---|
| | XI | XK | TAL | TKT |
| 321(5) | 0.06 | 0.17 | 2.10 | 0.91 |
| 481 | 0.04 | 0.23 | 2.27 | 0.74 |
| 2032 | 0.15 | 0.23 | 1.76 | 1.05 |
| 2122 | 0.04 | 0.19 | 1.56 | 0.51 |
| int2 | 0.02 | 0.02 | 1.19 | 0.31 |
| X9i | 0.04 | 0.06 | ND | 0.03 |
| 31821/pZB5 | 0.06 | 0.55 | 2.52 | 1.78 |
| C25 | 0.20 | 0.81 | 3.78 | 1.99 |
| 31821-5C | 0.08 | 0.07 | 0.01 | 0.01 |

ND: not detected.

Example XII

Chemical Mutation

The following example illustrates the process of mutagenesis of the Zymomonas integrants in an attempt to improve growth in xylose medium. Single colonies of integrants int2/xyl321 and x9t(Penott)Pi#8 were inoculated in RMG and incubated at 30° C. overnight. The grown cultures were used to inoculate Mating Medium supplemented with 5% glucose (OD=0.15~0.2) and incubated at 30° C. until OD=0.5~0.6. Cells were harvested and treated with a chemical mutagen 1-Methyl-3-nitro-1-nitrosoguanidine (MNNG or NTG) at 25 μg/ml concentration. The NTG-treated cells were collected, washed in RMG twice and resuspended in RMGX (0.5% glucose and 1.5% xylose) for growth. The grown cultures were sub-cultured twice in the same medium followed by streaking on RMX plates. The larger colonies were re-streaked on RMX plates. Largest colonies were picked and inoculated in RMX liquid medium. The grown cultures were again streaked out on RMX plates. Finally, the largest colonies were picked and grown in RMX. Two of the best growers are designated 8b and 2/321–2. One of the strains, 8b, were further evaluated further. Generally, the mutant has improved xylose utilization in the mixture of glucose and xylose as well as in the presence acetate as described in the following examples.

Example XIII

The following example illustrates fermentation evaluation of the several integrants constructed based on Z. mobilis ATCC31821-5C host. Strain C25 and the plasmid-bearing strain 31821/pZB5 were used as control for fermentation evaluation.

Fermentation evaluation was done in BioStat-Q fermentors with 500 mL working volume under pH and temperature control conditions. The pH was controlled at 5.5 using KOH (2N) for titration and temperature was controlled at 30° C. The fermentation media RM contained a mixture of glucose and xylose (RMGX (1%:6%) and RMGX (3.5%:3.5%)). All components of the growth media were prepared separately as filter sterilized stock solutions as RM (10×), glucose (50%), and xylose (50%). The fermentors were autoclaved and the growth media was added under sterile condition into fermentors. Inoculum was prepared in 250 mL flask containing 200 mL media RMGX (2%:2%). After overnight growth the culture was centrifuged and concentrated in 10 mL media similar to fermentation media. The volume of the inoculum needed to start the fermentation with OD of 0.1 at 600 nm was calculated and used to inoculate the fermentors. Fermentors were sampled frequently as required. Samples were analyzed by HPLC for sugars, ethanol, and by products.

Figure 29A:
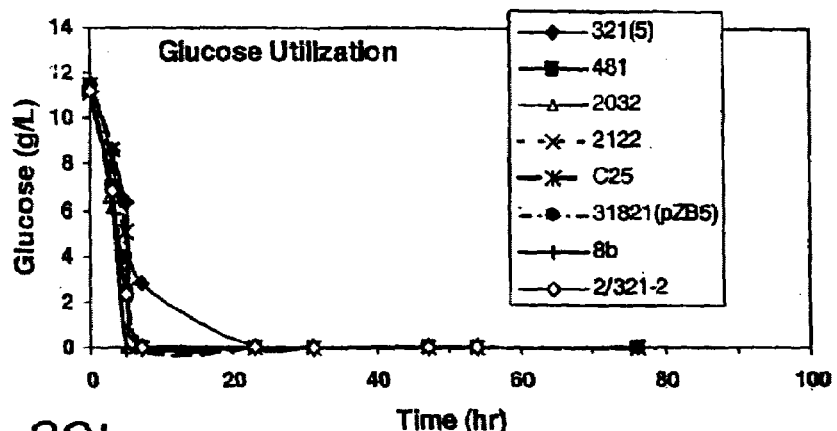
FIGS. 29 A through C are demonstration of glucose (29A) and xylose (29B) utilization and ethanol production (29C) in RMGX (1%:6%) for *Zymomonas* integrants in pH controlled fermentation.
Figure 29B:
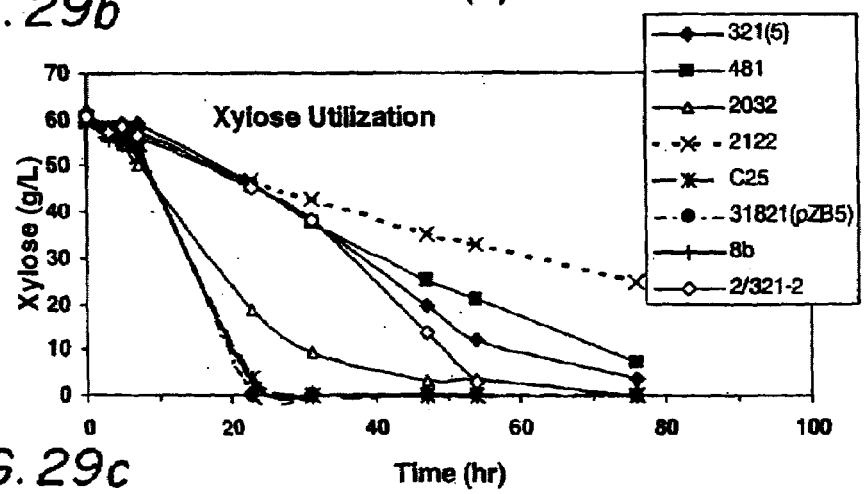
Figure 29C:
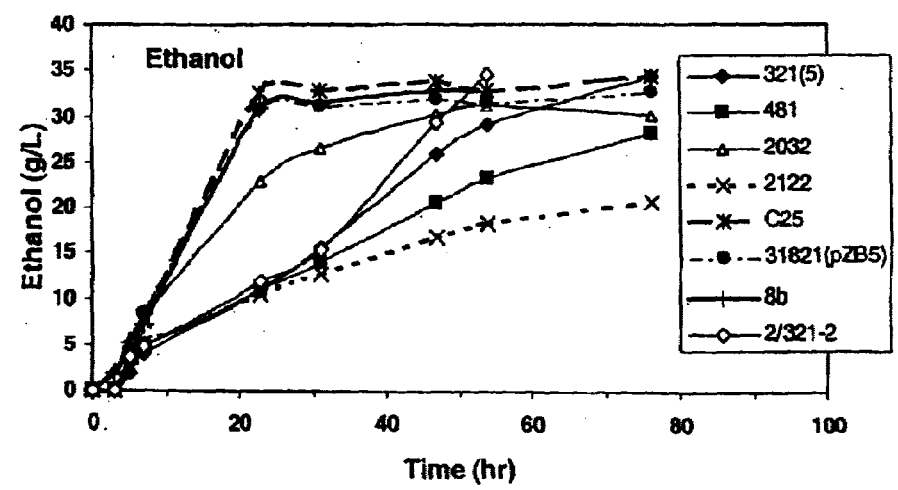
Figure 30A:
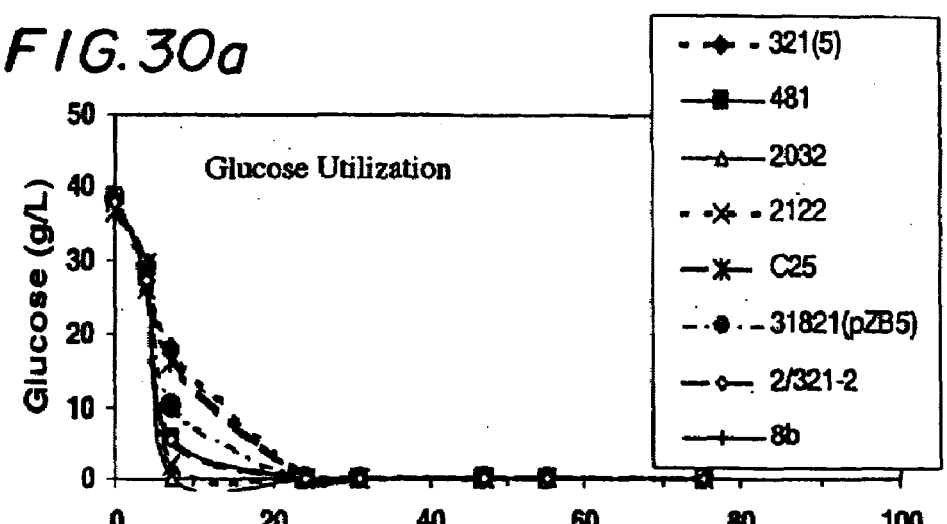
FIGS. 30 A through C are demonstration of glucose (30A) and xylose (30B) utilization and ethanol production (30C) in RMGX (3.5%:3.5%) for *Zymomonas* integrants in pH controlled fermentation.
Figure 30B:
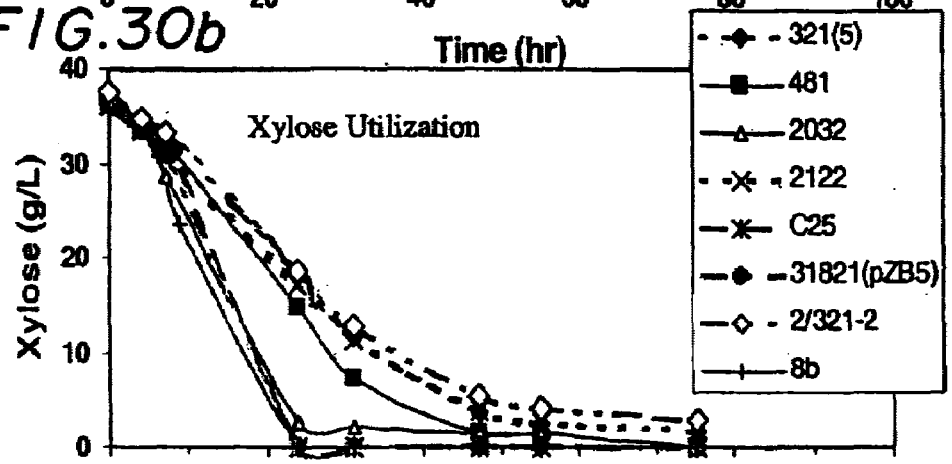
Figure 30C:
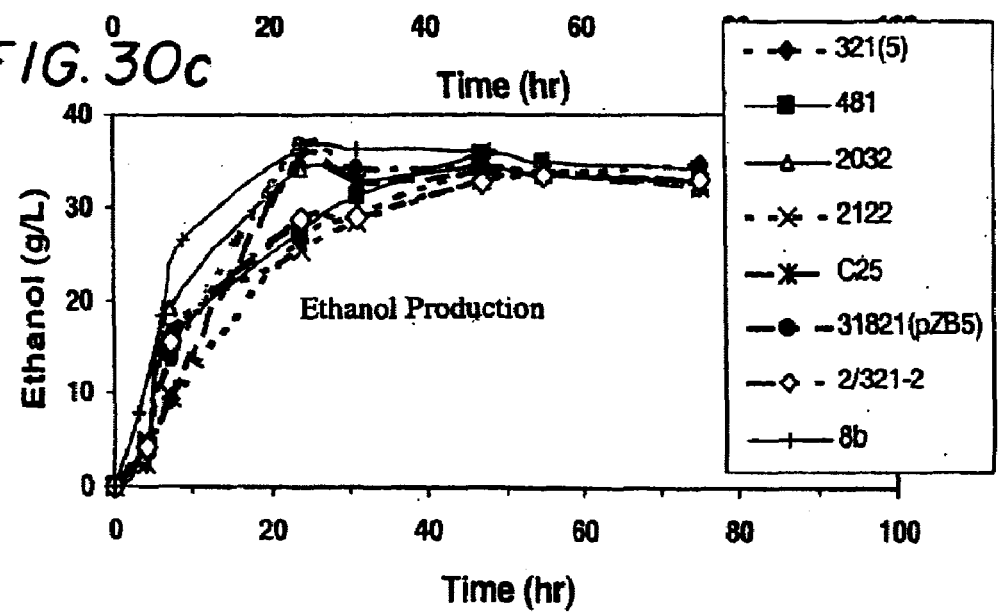

All the strains fermented glucose and xylose to ethanol with strains 8b and 2032 showing the best performance under pH controlled fermentations (FIGS. 29 and 30). The integrated strains 8b and 2032 showed similar performance as the plasmid-bearing strain 31821/pZB5 and the integrant C25, which is based on the 39676 host.

Example XIV

Figure 32A:
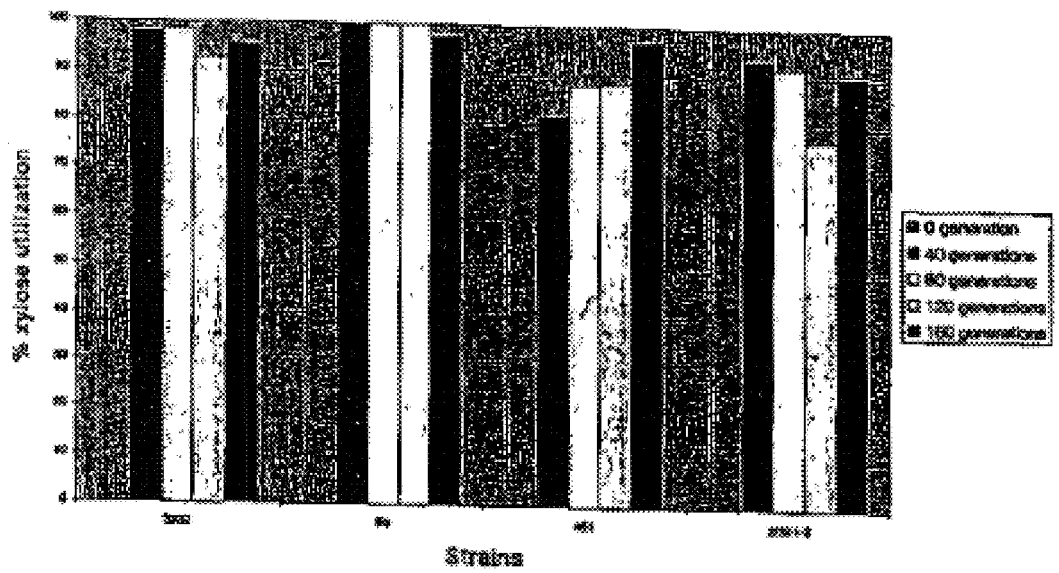
FIGS. 32 A and B are graphic representation which illustrates the stability of the stable xylose fermenting *Z. mobilis* strains, 2032, 8b, 481 and 2/321-2, according to the present invention. The graph shows the stability of genomic integrated xylose-fermenting strains, using the xylose utilization (32A) and ethanol process yield (32B). Strains 2032, 8b, 481 and 2/321-2, of the present invention remained stable for more than 80 generations. The fermentation medium comprised RM with 2% glucose and 2% xylose and the temperature was constant at 30° C.
Figure 32B:
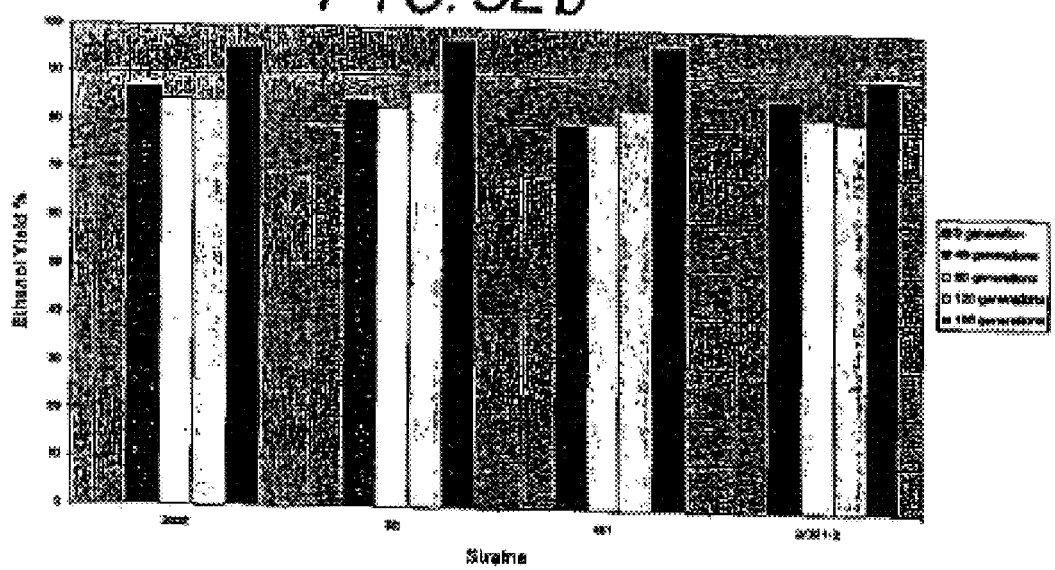
Figure 33:
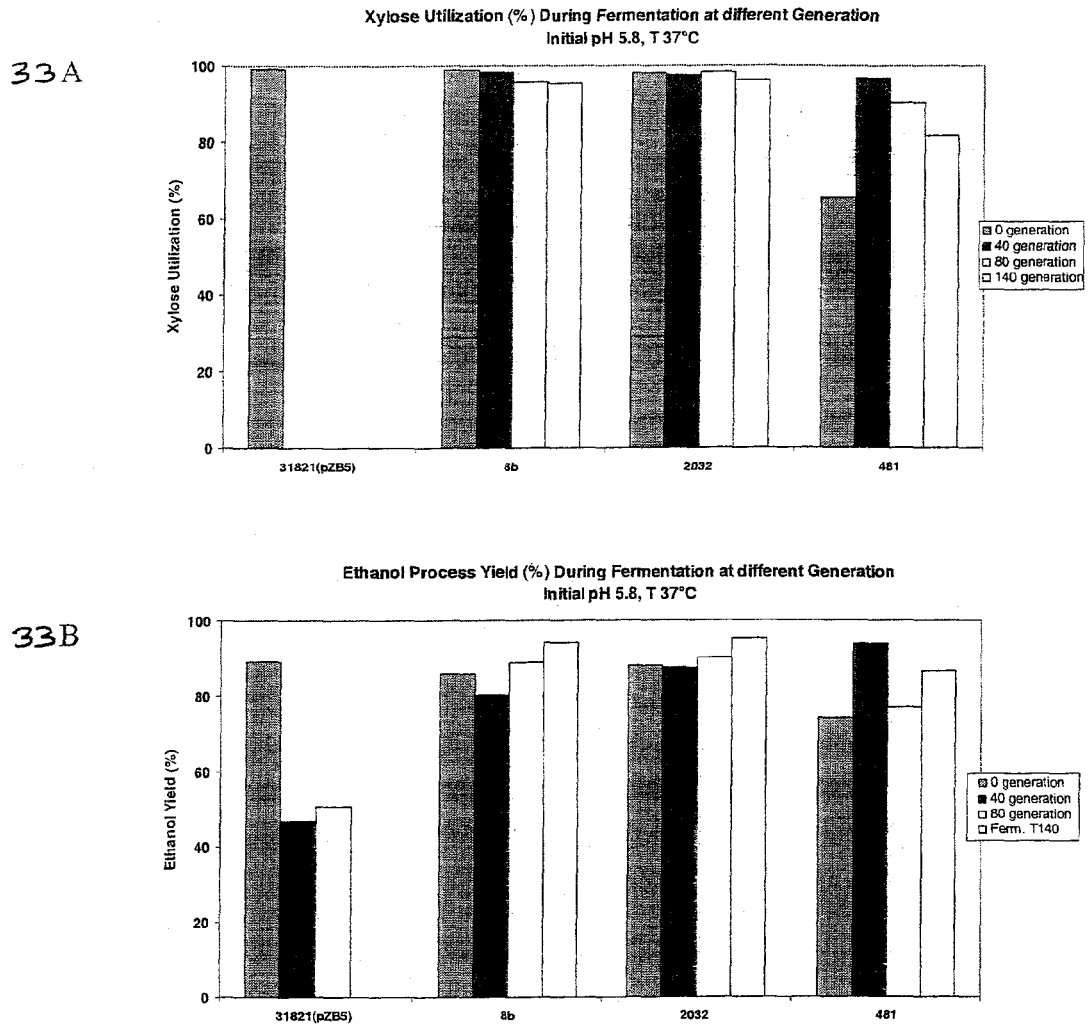
FIG. 33 A and B are graphic representation which illustrates the stability of the stable xylose fermenting *Z. mobilis* strains, 8b, 2032, 481 and plasmid-bearing strain (31821/pZB5), according to the present invention. The graph shows the stability of genomic integrated xylose-fermenting strains, using the xylose utilization (33A) and ethanol process yield (33B). Strains 2032, 8b and 481 of the present invention remained stable for more than 80 generations. The fermentation medium comprised RM with 2% glucose and 2% xylose and the temperature was constant at 37° C.

The following example illustrates the stability of the Zymomonas integrants. The test was done by a serial transfer of the culture in a non-selective medium (RMG), using 15 mL Falcon sterile tubes containing 10 mL medium as (see FIG. 31). These strains were cultured in RMG medium and serially transferred daily after about 10 generations. At every 40 generations, the cells were used to inoculate a flask containing 2% glucose and 2% xylose for examination of their ability to ferment glucose and xylose to ethanol. Ethanol process yields, and xylose utilization rates, were used as the the indication of stability trait. All the intgrants are shown to be stable at least for 140 to 160 generations without selection at both temperatures 30° C. and 37° C. (FIGS. 32 and 33). The plasmid-bearing strain 31821/pZB5 lost the xylose utilization capabilities within 40 generations at both 30° C. and 37° C. (data on 37° C. shown in FIG. 33).

Example XV

Figure 34D:
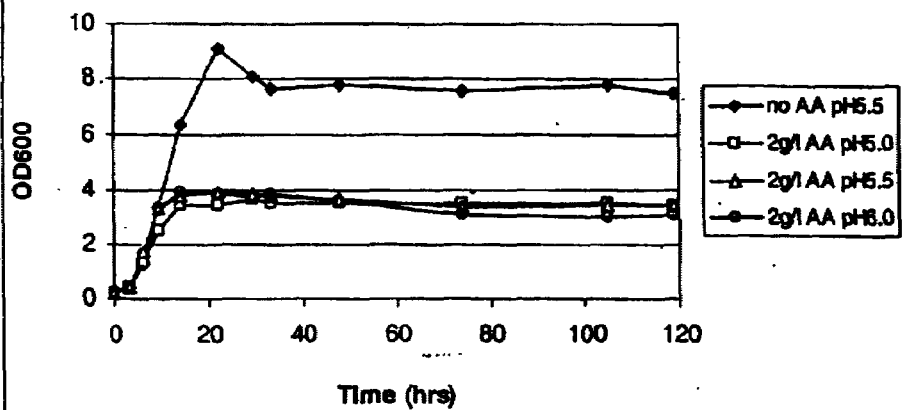
FIGS. 34 A through F are graphic representation which illustrates glucose utilization (34A), xylose utilization (34B), arabinose utilization (34C), growth (34D), ethanol production (34E) and ethanol process yield (34F) profiles in the presence of acetate at pH 5.0, 5.5 and 6.0.
Figure 34E:
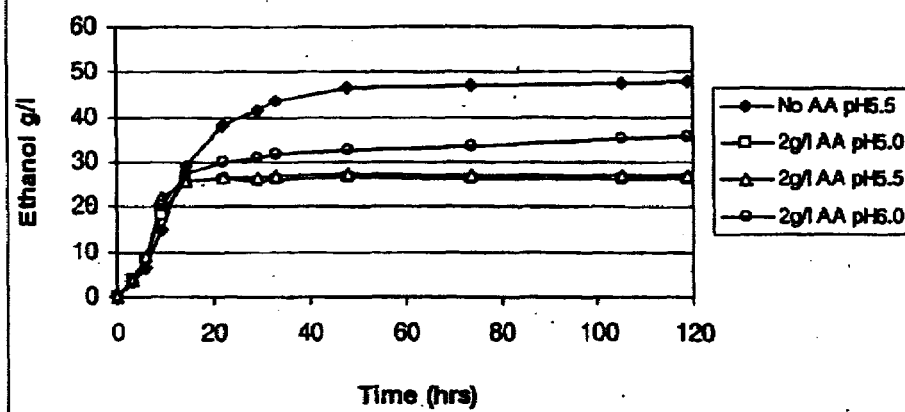
Figure 34F:
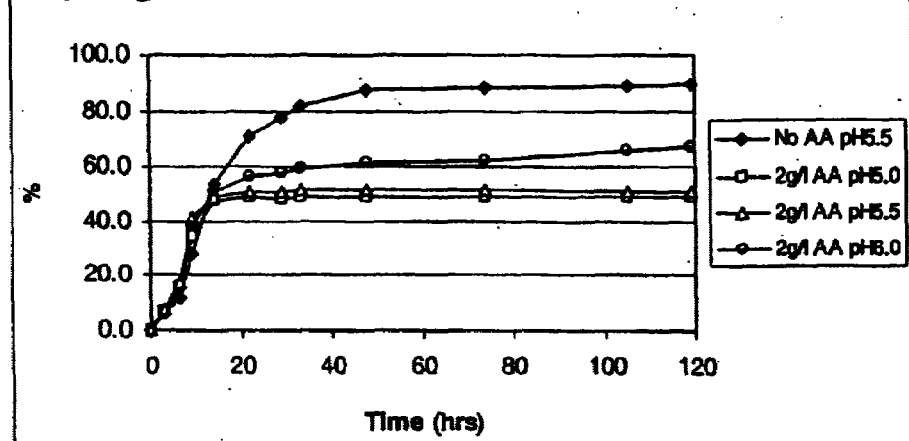

The following example illustrates the effect of the acetic acid concentration on the growth and xylose fermentation of AX101 as well as the effect of pH. Acetic acid is normally present in the hydrolysates of pretreated biomass feedstocks, and is inhibitory to the fermentation microorganism. Fermentation was run at pH 5, pH 5.5 and pH 6.0 with and without (pH 5.5) supplementing with 2 g/L acetate to evaluate the performance of strain AX101. The culture media used was RMGXA (4%:4%:2%) supplemented with the desired concentration of acetate. The result (FIG. 34) showed that 2 g/L acetate showed inhibitory effect on growth, xylose utilization and ethanol production of the strain. The inhibition was much stronger at lower pH (pH5.0) as compared at higher pH (pH6.0).

Example XVI

The following example illustrates the fill and draw process of fermentation of AX101. A study was designed to see if gradual adaptation of the strain AX101 to acetate would improve the performance of this strain in culture media with higher concentrations of acetic acid. First a set of batch fermentation on RMGXA (4%:4%:2%) at pH 5.5, T 30° C. with no acetate and 2 g/L acetate was compared. Since acetate effected sugar utilization at a low level of 2 g/L acetate, another study was designed in which 2 fermentors with RMGXA (4%:4%:2%) supplemented with 2 g/L acetate were inoculated from another fermentor at a similar sugar concentration except with lower acetate concentration of 0.5 g/L and 1 g/L respectively. The results showed no improvement on sugar utilization by strain AX101 in the presence of 2 g/L acetate.

Example XVII

Figure 35A:
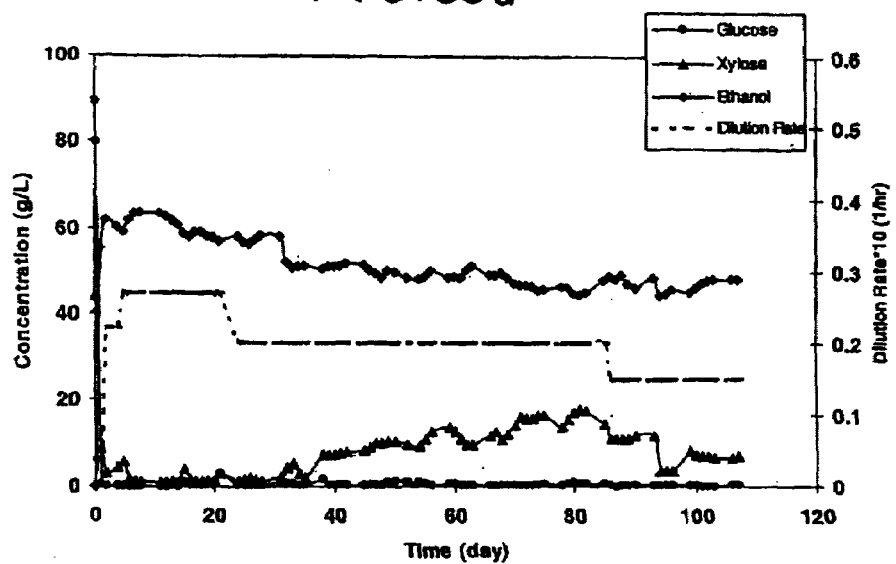
FIGS. 35 A and B are graphic representation which illustrates continuous and constant ethanol production from glucose and xylose (35A), and byproduct formation (35B) with increasing acetate concentration.
Figure 35B:
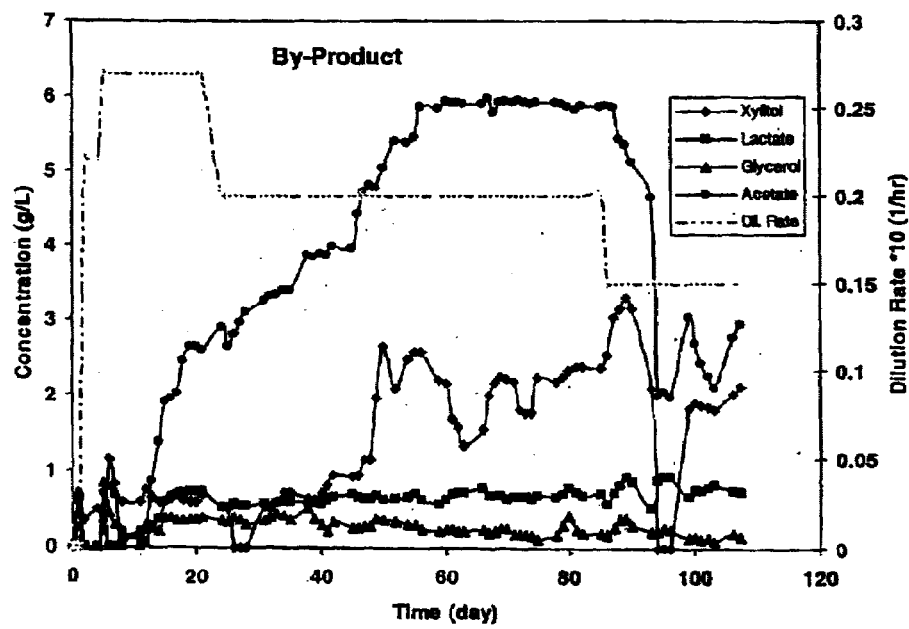

The following example illustrates the continuous fermentation of AX101. Continuous fermentations were carried out in MultiGen fermentors (New Bruswick Scientific, NJ, USA) with a 300 mL working volume and 300 rpm agitation. The pHs studied were 4.5, 5, and 5.5 controlled with KOH (2N). Temperature was kept at 30° C. for all the studies. Batch fermentation was started with an initial OD of 0.1 at 600 nm. Samples were taken periodically throughout the course of the fermentation and analyzed for sugars, ethanol, and byproducts by HPLC. After full glucose utilization and around 10 g/L xylose remaining in the fermentor the continuous fermentation was started by feeding a culture media with desired sugar composition at a low dilution rate (D) of 0.02 (1/hr). After 4 to 5 steady state cycles, where full glucose utilization and 80% xylose utilization was observed then the dilution rate was increased (FIG. 35). This process was continued until wash out stage was achieved which was indicated by a greater remaining xylose concentration and a reduced ethanol concentration. The ethanol process yield (Yp) was calculated based on the final concentration of ethanol produced per mass of initial total sugar added to the medium.

The strain AX101 was able to ferment a sugar mixture of 80 g/L glucose, 40 g/L xylose, and 15 g/L arabinose in corn steep liquor media supplemented only up to 6 g/L acetate after which wash out stage was observed.

Example XVIII

The following example illustrates the integrants are capable of fermenting glucose and xylose to ethanol in the presence of high concentration of acetate. Acetate is an inhibitiory compound normally found in the hydrolysates from pretreated biomass feedstocks.

Evaluation was done in 50 mL baffled shake flasks with 35 mL media containing RMGX (2%:2%) supplemented with different concentrations of acetate. Acetate was added as acetic acid to media RMGX and pH was adjusted by KOH pellets to 5.8. Inoculum was prepared in 125 mL flask containing 100 mL media RMGX (2%:2%), initial pH 5.8 at a desired temperature of 30° C. or 37° C.

Figure 36A:
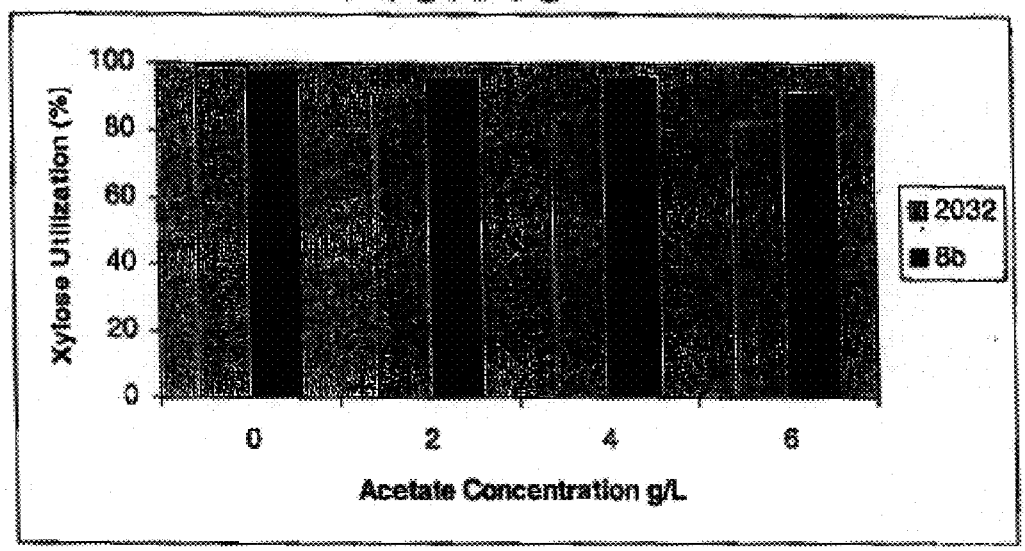
FIGS. 36 A and B are graphic representation which illustrates xylose utilization (36A) and ethanol yield (36B) in the presence of acetate concentration of 0, 2, 4 and 6 g/L.
Figure 36B:
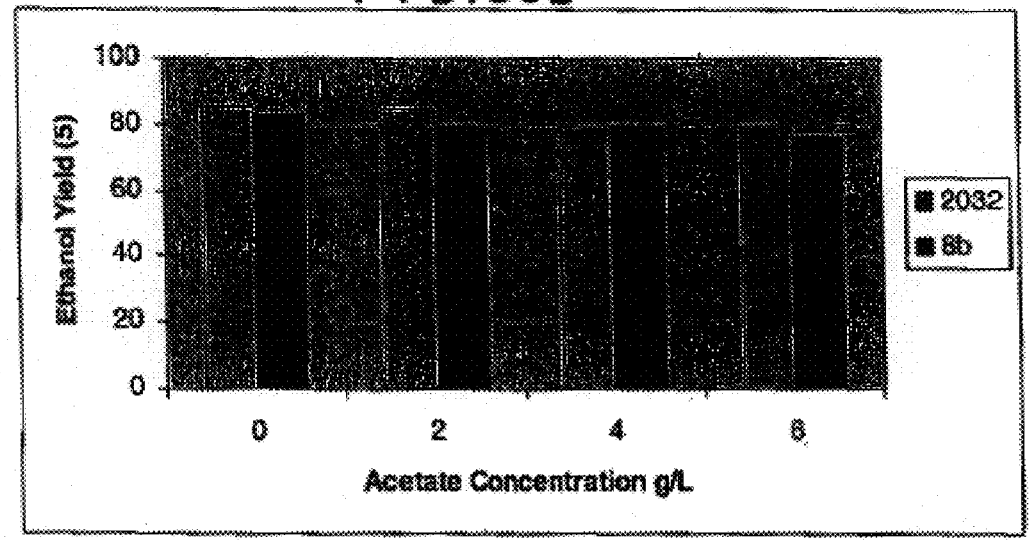

After overnight growth OD at 600 nm was measured and the each flask was inoculated with OD of 0.1 at 600 nm and incubated on a shaker at the desired temperatures. Samples were taken at different times and analyzed by HPLC for sugars, ethanol, and by products. As shown in FIG. 36, integrants 8b and 2032 are capable growth and ferment xylose to ethanol at acetate concentration of 2 g/l to 6 g/l in a medium without pH control. The inhibition by acetate at these concentrations on xylsoe utilization is minimal.

Figure 37A:
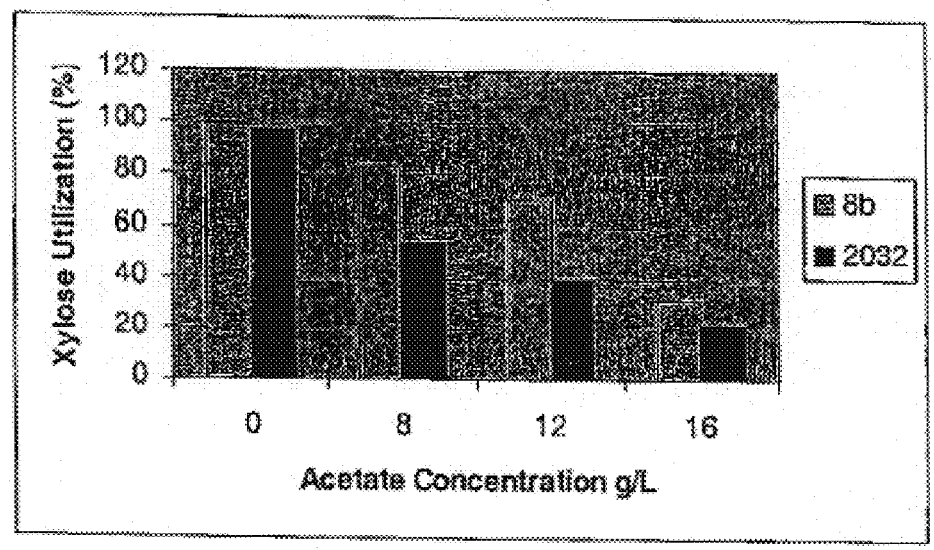
FIGS. 37 A and B are graphic representation which illustrates xylose utilization (37A) and ethanol yield (37B) in the presence of acetate concentration of 0, 8, 12 and 16 g/L.
Figure 37B:
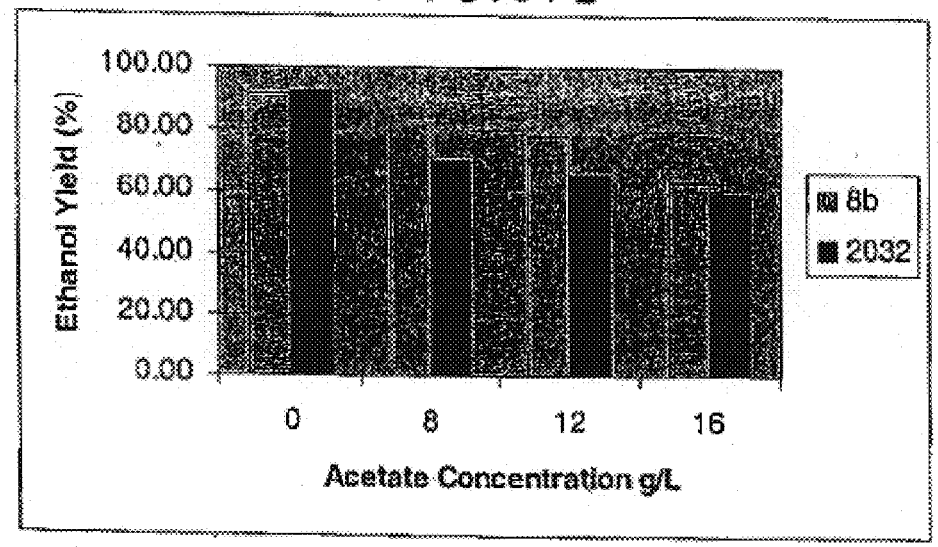

As shown in FIG. 37, all the integrants were capable of fermenting glucose and xylose to ethanol even in the presence of 16 g/l of acetate, and even in a medium without pH control. The final pHs of growth media were measure to be between 3.5–4.5. The previously constructed strains based on a 39676 host, such as AX101 and C25, were shown to be quite strongly inhibited by low acetic acid as low as 2 g/L.

Example XIV

Figure 38:
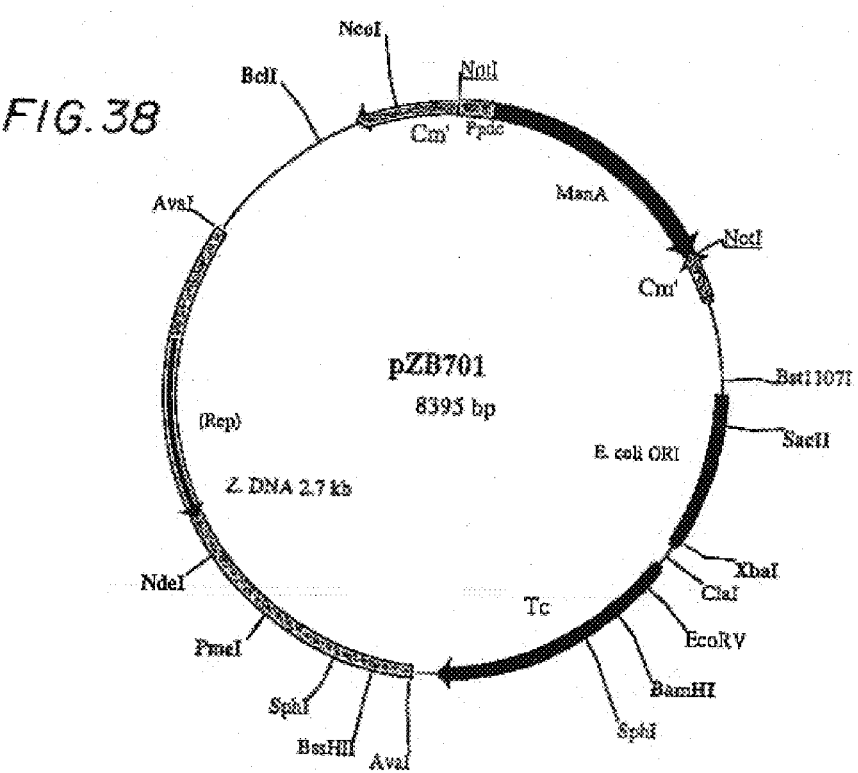
FIG. 38 is the plasmid map for pZB701 containing mannose utilization gene.

The following example illustrates that Z. mobilis strain 39676 and 31821 can be transformed with plasmid pZB701 (FIG. 38) containing a E. coli phosphomannose isomerase gene, ManA, under the control of the Zymomonas pyruvate decarboxylase (PDC) promoter, Ppdc.

Figure 39A:
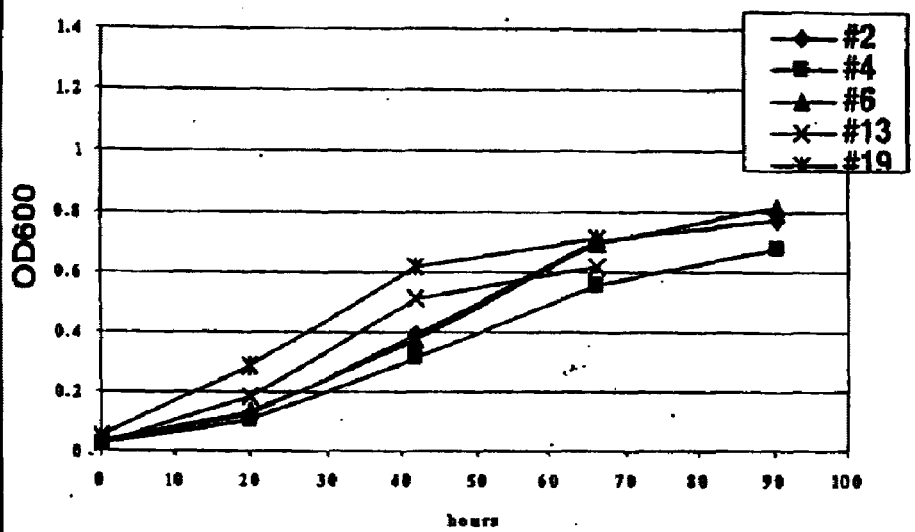
FIGS. 39 A and B are graphical representation of the growth adaptation of #2, 4, 6, 13, and 19 in RMM medium.
Figure 39B:
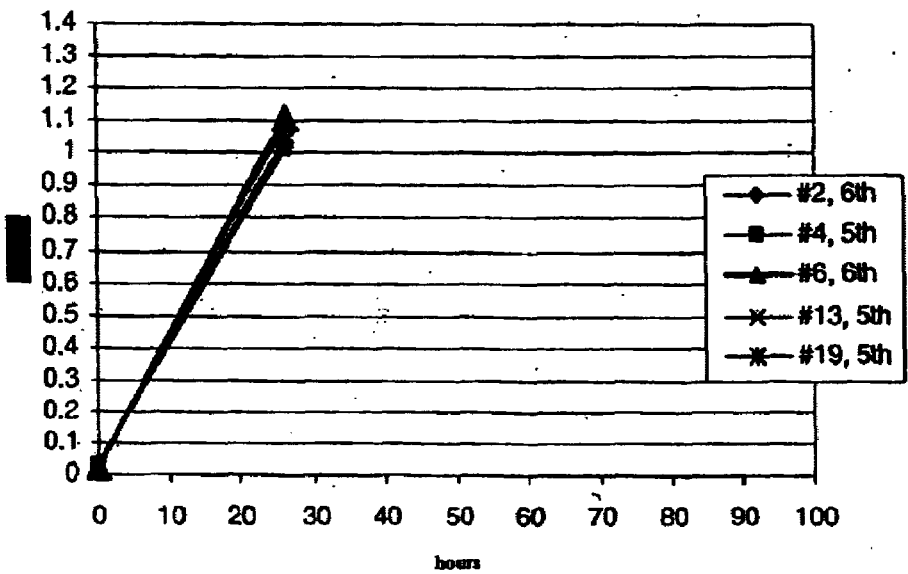

As shown in FIG. 39, transformants for both strains were able to utilize D-mannose as the sole carbon source. To confirm expression of ManA, all the intermediate and final constructs (including pZB801) generated were used to transform a manA(−) host, E. coli GMS407. Transformants were plated on McConkey agar containing mannose as the carbon source. Dark pink colonies indicated mannose utilization by the clones. Plasmid pZB701 extracted from a dark pink colony was used for the future transformation in Z. mobilis 206C or 31821. Z. mobilis transformants were selected on mating medium (MMG) containing tetracycline (Tc$^r$) followed by the testing in medium containing mannose (RMM). As shown in FIG. 39, all the transformants were able to grow in RMM initially and, after several serial transfers in RMM, showed improved growth rates.

For transformation of Z. mobilis 31821, pZB701 was prepared from E. coli JM110. These Tc$^r$ transformants were also able to grow in RMM. Analysis of the supernatants of RMM grown cultures indicated ethanol was produced by both 39676 and 31821 transformants.

The plasmid pZB701 containing mannose utilizing gene can be further transformed into the genomic-integrated xylose- and arabinose-fermenting strains that the applicants have constructed, such as C25, AX101, AX1, 321(5), 481, 8b, 2032, 2122 based on 39676 and 31821 host strains. The success of transformation in Z. mobilis 39676 and 31821 with pZB701 (containing ManA gene) and the fermentation of mannose to ethanol by the transformants has been demonstrated. The above Zymomonas integrants may also be transformed with the plasmid pZB701 to obtain Z. mobilis strains capable of fermenting xylose, arabinose, mannose and glucose to ethanol. The transformed Zymomonas strains are expected to be capable of utilizing xylose, arabinose, mannose and glucose in the biomass feedstock and ferment all the sugars to ethanol.

While the present invention has been described in connection with the illustrated embodiments. It will be appreciated and understood that modifications may be made without departing from the true spirit and scope of the invention.

The invention claimed is:

1. A process for using a genetically modified *Zymomonas* integrant to produce ethanol from a pentose sugar, comprising:
    providing a *Zymomonas* integrant comprising a sequence encoding more than one pentose-sugar fermenting enzymes incorporated by a first integration event of transposition and a second integration event of homologous recombination, wherein said pentose fermenting enzymes comprises xylose isomerase, xylulokinase, transketolase, and transaldolase;
    adding the integrant *Zymomonas* comprising said sequence encoding to a feedstock comprising pentose under fermentation conditions; and
    fermenting the pentose sugar to provide a composition comprising ethanol; said *Zymomonas* integrant being selected from the group consisting of ATCC 31821-5C Penotaltkt/Pgapxyl-AB and ATCC 31821-5C Pgaptaltkt/Pgapxyl AB.

2. The process of claim 1 wherein the first integration event comprises a transposition integration of a first operon comprising a sequence encoding more than one pentose-fermenting enzyme.

3. The process of claim 2 wherein the first operon includes a sequence encoding transaldolase and transketolase.

4. The process of claim 2 wherein the first operon is further defined as comprising Penotaltkt or Pgaptaltkt.

5. The process of claim 1 wherein the second integration event comprises a homologous recombination with a second operon comprising a sequence encoding more than one pentose-fermenting enzyme.

6. The process of claim 5 wherein the second operon is further defined as comprising PgapxylAB.

7. The process of claim 5 wherein the second operon includes a sequence encoding xylose isomerase and xylulokinase.

8. The process of claim 1 wherein the *Zymomonas* integrant is ATCC31821-5C Penotaltkt/PgapxylAB.

9. The process of claim 1 wherein the *Zymomonas* integrant is ATCC31821-5C Pgaptaltkt/PgapxylAB.

* * * * *

SEQUENCE LISTING

<160> NUMBER OF SEQ ID NOS: 33

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 1
ttgctaacgc agtcaggc                                           18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 2
gaatccgtta gcgaggtg                                           18

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
tatgggttca gcggcatgag                                         20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 4
atgggcatga gatccatagc c                                       21

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 5
tcctaacatg gtaacgttc                                                19

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 6
ccaaccttac cagagggc                                                 18

<210> SEQ ID NO 7
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 7
cgtctaaaag attttaagaa aggtttcgat atgacggaca aattgacc                48

<210> SEQ ID NO 8
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 8
cattttgact ccagatctag attacagcag atcgccgatc attttttcc               49

<210> SEQ ID NO 9
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 9
ccatcgattc tagaatctcg cgtaataaaa ctatcaggcg caatcg                  46

<210> SEQ ID NO 10
<211> LENGTH: 54
<212> TYPE: DNA
<213> ORGANISM: Artificial Sequence
<220> FEATURE:
<223> OTHER INFORMATION: Description of Artificial Sequence: Primer

<400> SEQUENCE: 10
cgcggatcca gatctggcct aggcggcctc ataatatggg caaagacact cccg         54

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Primer

```
<400> SEQUENCE: 11
gaagatctgc ggccgcgttt tggtgccaat gttatcgcc                                39

<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 12
gaagatctaa gcttggatag cggcttatag caacgagtgc                               40

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 13
aaaggccgcc taggcc                                                         16

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 14
aaaggcctag gcggcc                                                         16

<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 15
ccgaataaat acggccgcct gtgacggaag atcacttc                                 38

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 16
taacgaccct gccggccgcc tgaaccgacg accgggtcg                                39

<210> SEQ ID NO 17
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 17
tcgcggatcc tctatccctt tattttcta tccccatcac ctcgg                          45

<210> SEQ ID NO 18
<211> LENGTH: 40
```

```
<212> TYPE: DNA
<213> ORGANISM: Artificial Sequence
<220> FEATURE:
<223> OTHER INFORMATION: Description of Artificial Sequence: Primer

<400> SEQUENCE: 18
tcgcggatcc gcggctgaca tacatcttgc gaatataggg                                40

<210> SEQ ID NO 19
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
catgcgcggc cgcc                                                           14

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 20
tcgcggatcc gtctatgcgc gcgtcgcaat attcagttcc                               40

<210> SEQ ID NO 21
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 21
tcgcggatcc gtcgcttgtc tattaaacaa gcgcatccgg c                             41

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 22
ctaacatgtt gactccttct ctagacttag cg                                       32

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 23
gttgaaaccg ctgggcacca cgc                                                 23

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 24
```
cgcactacac ggtcgttctg ttac                                              24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 25
ggttgcagcc acgagtaagt cttc                                              24

<210> SEQ ID NO 26
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 26
cagtctagag gccgcctagg ccgttcgatc aacaacccga atcc                        44

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 27
caatttgtcc gtcatgttta ttctcctaac                                        30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 28
gttaggagaa taaacatgac ggacaaattg                                        30

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 29
ccagatcgtc tagattacag cagatcgcc                                         29

<210> SEQ ID NO 30
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 30
cagtctagag gccgcctagg ccgttcgatc aacaacccga atcc                        44

<210> SEQ ID NO 31
<211> LENGTH: 29
<212> TYPE: DNA

```
<213> ORGANISM: Artificial Sequence
<220> FEATURE:
<223> OTHER INFORMATION: Description of Artificial Sequence: Primer

<400> SEQUENCE: 31
ccagatcgtc tagattacag cagatcgcc                                        29

<210> SEQ ID NO 32
<211> LENGTH: 73
<212> TYPE: DNA
<213> ORGANISM: Artificial Sequence
<220> FEATURE:
<223> OTHER INFORMATION: Description of Artificial Sequence: Primer

<400> SEQUENCE: 32
cagggccgcc taggccataa cttcgtatag catacattat acgaagttat cctgtgacgg      60
aagatcactt cgc                                                         73

<210> SEQ ID NO 33
<211> LENGTH: 71
<212> TYPE: DNA
<213> ORGANISM: Artificial Sequence
<220> FEATURE:
<223> OTHER INFORMATION: Description of Artificial Sequence: Primer

<400> SEQUENCE: 33
cagggcctag gcggccataa cttcgtataa tgtatgctat acgaagttat cctgaaccga      60
cgaccgggtc g                                                           71
```